US006572865B1

(12) United States Patent
Nano

(10) Patent No.: US 6,572,865 B1
(45) Date of Patent: Jun. 3, 2003

(54) *MYCOBACTERIUM TUBERCULOSIS* DNA SEQUENCES ENCODING IMMUNOSTIMULATORY PEPTIDES AND METHODS FOR USING SAME

(75) Inventor: Francis E. Nano, Victoria (CA)

(73) Assignee: University of Victoria Innovation and Development Corporation, Victoria (CA)

(*) Notice: Subject to any disclaimer, the term of this patent is extended or adjusted under 35 U.S.C. 154(b) by 0 days.

(21) Appl. No.: 09/477,135

(22) Filed: Jan. 3, 2000

Related U.S. Application Data

(63) Continuation-in-part of application No. 08/990,823, filed on Dec. 15, 1997, now Pat. No. 6,228,371, which is a continuation of application No. PCT/US96/10375, filed on Jun. 14, 1996.
(60) Provisional application No. 60/000,254, filed on Jun. 15, 1995.

(51) Int. Cl.$^7$ .................. A61K 39/04; A61K 39/02; A61K 39/00
(52) U.S. Cl. ............... 424/248.1; 424/9.1; 424/9.2; 424/184.1; 424/185.1; 424/190.1; 424/234.1; 530/300; 530/350; 536/23.1; 536/23.7
(58) Field of Search .................. 424/9.1, 9.2, 184.1, 424/185.1, 190.1, 234.1, 248.1; 530/300, 350; 536/23.1, 23.7

(56) References Cited

PUBLICATIONS

Skamene, E. (1989). Genetic control of susceptibility of Mycobacterial Infections. *Ref. Infect. Dis.* 11:S394–S399.
Kaufmann, S.H.E. (1991). Role of T–Cell Subsets in Bacterial Infections. *Current Opinion in Immunology* 3:465–470.
Orme, I.M., et al. (1992). T Lymphocytes Mediating Protection and Cellular Cytolysis During the Course of Mycobacterium–Tuberculosis Infection—Evidence for Different Kinetics and Recognition of a Wide Spectrum of Protein Antigens. *Journal of Immunology* 148:189–196.
Daugelat, S., et al. (1992). Secreted Antigens of *Mycobacterium tuberculosis*: characterization with T Lymphocytes from Patients and Contacts after Two–Dimensional Separation. *J. Infect. Dis.* 166:186–190.
Barnes et al. (1989). Characterization of T–Cell Antigens Associated with the Cell Wall Protein–Peptidoglycan Complex of *Mycobacterium tuberculosis*. *J. Immunol.* 143:2656–2662.

Collins et al. (1988). Biological activity of protein antigens isolated from *Mycobacterium tuberculosis* culture filtrate. *Infect. Immun.* 56:1260–1266.
Lamb et al. (1989). Identification of Mycobacterial Antigens Recognized by T Lymphocytes. *Rev. Infect. Dis.* 11:S443–S447.
Pal P.G., et al. (1992). Immunization with Extracellular Proteins of *Mycobacterium tuberculosis* Induces Cell–Mediated Immune Responses and Substantial Protective Immunity in a Guinea Pig Model of Pulmonary Tuberculosis. *Infect. Immun.* 60:4781–4792.
Andersen (1994). Effective Vaccination of Mice against *Mycobacterium tuberculosis* Infection with a Soluble Mixture of Secreted Mycobacterial Proteins. *Infection & Immunity* 62:2536–2544.
Jardim et al. (1990). Immunoprotective *Leishmania major* Synthetic T Cell Epitopes. *J. Exp. Med.* 172:645–648.
Orme et al. (1993). Cytokine Secretion by CD4 T Lymphocytes Acquired in Response to *Mycobacterium tuberculosis* Infection. *J. Immunology* 151:518–525.
Boesen et al. (1995). Human T–Cell Responses to Secreted Antigen Fractions of *Mycobacterium tuberculosis*. *Infection and Immunity* 63:1491–1497.
Mougneau et al. (1995). Expression Cloning of a Protective Leishmania Antigen. *Science* 268:536–566.
Mdluli et al. (1995). New vectors for the in vitro generation of alkaline phosphatase fusions to proteins encoded by G+C–rich DNA. *Gene* 155:133–134.
Tommassen et al. (1993). Use of the enterobacterial outer membrane protein PhoE in the development of new vaccines and DNA probes. *Intl. J. Microbiol. Virol. Parasitol. infect. Dis.* 278: 396–406.
Janssen et al. (1994). Immunogenicity of a mycobacterial T–cell epitope expressed in outer membrane protein PhoE of *Escherichia coli*. *Vaccine* 12: 405–409.
Lim et al. (1995). Identification of *Mycobacterium tuberculosis* DNA sequences encoding exported proteins by using phoA gene fusions. *J. Bacteriol.* 177: 59–65.
Oettinger et al. (1994). Cloning and B–Cell Epitope Mapping of MPT64 from *Mycobacterium tuberculosis* H37Rv. *Infection and Immunity* 62: 2058–2064.
Young et al. (1988). Stress proteins are immune targets in leprosy and tuberculosis. *Proc. Natl. Acad. Sci. USA* 85: 4267–4270.

*Primary Examiner*—Rodney P Swartz
(74) *Attorney, Agent, or Firm*—Klarquist Sparkman, LLP

(57) ABSTRACT

Nucleotide sequences isolated from *Mycobacterium tuberculosis* are disclosed. These sequences encode immunostimulatory peptides. Also disclosed are vaccine preparations formulated using these peptides.

28 Claims, 4 Drawing Sheets

```
GTGATACAGGAGGCGCCAACAGTGACACCCTCGCGGGCCAGGTCGTTTGCAACGCTTTGTCGCAGTGCAGGC
     ----+----+----+----+----+----+----+----+----+----+----+----+----+----+    70
CACTATGTCCTCCGCGGTTGTCACTGTGGAGCGCCCGGTCCAGCAAACGTTGCGAACAGCGTCACGTCCG
                                    M  T  P  R  G  P  R  L  Q  R  L  S  Q  C  R

CTCAGCGCGGCGGCTCCGGAGGGCCCTGCCCGTGGTCTCTTCGACACAGTCTGGCCTCGCAGCAATGCTGGGGCATT
     ----+----+----+----+----+----+----+----+----+----+----+----+----+----+   140
GAGTCGCGCCGCCGAGGCCTCCCGGGACGGGCACCAGAAGCTGTGTCAGACCGGAGCGTCGTTACGACCCCGTAA
 P  Q  R  G  S  G  G  P  A  R  G  L  R  Q  L  A  L  A  A  M  L  G  A  L

GGCCGTCACCGTCAGTGGATGCAGCTGGTCGGAAGCCCTGGGCCATCGGTTGGCCGAGGGCATTACCCCG
     ----+----+----+----+----+----+----+----+----+----+----+----+----+----+   210
CCGGCAGTGGCAGTCACCTACGTCGACCAGCCTTCGGGACCCGGTAGCCAACCGGCTCCCGTAATGGGGC
 A  V  T  V  S  G  C  S  W  S  E  A  L  G  I  G  W  P  E  G  I  T  P

GAGGCACACCTCAATCGAGAACTGTGGATCGGCGGTGATCGCCTCCCTGGCCGGTTGGGGTAATCGTGT
     ----+----+----+----+----+----+----+----+----+----+----+----+----+----+   280
CTCCGTGTGGAGTTAGCTCTTGACACCTAGCCGCCACTAGCGGAGGGACCGGCCAACCCCATTAGCACA
 E  A  H  L  N  R  E  L  W  I  G  A  V  I  A  S  L  A  V  G  V  I  V
```

FIG. 1(A)

```
GGGGTCTCATCTTCTGGTCCGGTATTTCACCGGAAGAAGAACACCGACACTGAGTTGCCCGCCAGTT
                                                                        350
CCCCAGAGTAGAAGACCAGGCGCCATAAAGTGGCCTTCTTCTTGTGGCTGTGACTCAACGGGCGGTCAA
 W  G  L  I  F  W  S  A  V  F  H  R  K  K  N  T  D  T  E  L  P  R  Q  F

CGGCTACAACATGCCGCTAGAGCTGGTTCTCACCGTTCCTCATCATCTCGGTGTGCTGTTTTAT
                                                                        420
GCCGATGTTGTACGGCGATCTCGACCAAGAGTGGCAGTATGCCAAGGAGTAGTAGAGCCACGACAAAATA
 G  Y  N  M  P  L  E  L  V  L  T  V  I  P  F  L  I  I  S  V  L  F  Y

TTCACCGTCGTGGTGCAGGAGAAGATGCTGCAGATAGCCAAGGATCCCGAGGTCGTGATTGATATCACGT
                                                                        490
AAGTGGCAGCACCACGTCCTCTTCTACGACGTCTATCGGTTCCTAGGGCTCCAGCACTAACTATAGTGCA
 F  T  V  V  V  Q  E  K  M  L  Q  I  A  K  D  P  E  V  V  I  D  I  T

CTTTCCAGTGGAATTGGAAGTTTGGCTATCAAAGGGTGAACTTCAAAGACGGCACACTGACCTATGATGG
                                                                        560
GAAAGGTCACCTTAACCTTCAAACCGATAGTTTCCCACTTGAAGTTTCTGCCGTGTGACTGGATACTACC
 S  F  Q  W  N  W  K  F  G  Y  Q  R  V  N  F  K  D  G  T  L  T  Y  D  G
```

FIG. 1(B)

```
TGCCGATCCGGGAGGCGCAAGGCGCCATGGTTTCCAAGCCAGAGGGCAAGGACAAGTACGGGGAAGAGCTG
                                                                        630
ACGGCTAGGCCCTCGCGTTCCGCGGTACCAAAAGGTTCGGTCTCCCGTTCCTTCATGCCGCTTCTCGAC
 A  D  P  E  R  K  R  A  M  V  S  K  P  E  G  K  D  K  Y  G  E  E  L

GTCGGGCCGGTGCGCGGGCTCAACACCGAGGACCGGACCTACCTGAATTTCGACAAGGTCGAGACGTTGG
                                                                        700
CAGCCCGGCCACGCGCCCGAGTTGTGGCTCCTGGCCTGGATGGACTTAAAGCTGTTCCAGTCTGCAACC
 V  G  P  V  R  G  L  N  T  E  D  R  T  Y  L  N  F  D  K  V  E  T  L

GCACCAGCACCGAAATTCCGGTGCTGGTCCCGCAAGCGTATCGAATTCCAAATGGCCTCAGC
                                                                        770
CGTGGTCGTGGCTTTAAGGCCACGACCAGGCCGTTCGCATAGCTTAAGGTTTACCGGAGTCG
 G  T  S  T  E  I  P  V  L  L  P  S  G  K  R  I  E  F  Q  M  A  S  A

CGATGTGATACACGCATTCTGGGTGCCGGAGTTCTTGTTCAAGCGTGATGCCTAACCCGGTGGCA
                                                                        840
GCTACACTATGTGCGTAAGACCCACGGCCTCAAGAACAAGTTCGCACTGCACTACGGATTGGGCCACCGT
 D  V  I  H  A  F  W  V  P  E  F  L  F  K  R  D  V  M  P  N  P  V  A
```

FIG. 1(C)

FIG. 1(D)

```
     AACAACTCGGTCAACGTCTTCCAGATCGAAGAAATCACCAAGACCGGAGCATTCGTGGGCCACTGCCCG   910
     TTGTTGAGCCAGTTGCAGAAGGTCTAGCTTCTTTAGTGGTTCTGGCCTCGTAAGCACCCGTGACGCGGC
      N  N  S  V  N  V  F  Q  I  E  E  I  T  K  T  G  A  F  V  G  H  C  A

AGATGTGTGGCACGTATCACTCGATGATGAACTTCGAGGTCCGCGTCGTGACCCCCAACGATTTCAAGGC   980
     TCTACACACCGTGCATAGTGAGCTACTACTTGAAGCTCCAGGCGCAGCACTGGGGGTTGCTAAAGTTCCG
      E  M  C  G  T  Y  H  S  M  M  N  F  E  V  R  V  V  T  P  N  D  F  K  A

CTACCTGCAGCAACGCATCGACGGGAATACAAACGCCCTGCGGGCGATCAACCAGCCGCCCTT        1050
     GATGGACGTCGTTGCGTAGCTGCCCTTATGTTTGCGGGACGCCCGCTAGTTGGTCGGCGGGGAA
      Y  L  Q  Q  R  I  D  G  N  T  N  A  E  A  L  R  A  I  N  Q  P  P  L

GCGGTGACCACCCACCCGTTTGATACTCGCCGGTGAATTGGCCCGTAGGTTAGGACGCTC          1120
     CGCCACTGGTGGGTGGGCAAACTATGAGCGGCCACTTAACCGGGCATCCAATCCTGCGAG
      A  V  T  T  H  P  F  D  T  R  R  G  E  L  A  P  Q  P  V  G
```

MYCOBACTERIUM TUBERCULOSIS DNA SEQUENCES ENCODING IMMUNOSTIMULATORY PEPTIDES AND METHODS FOR USING SAME

CROSS REFERENCE TO RELATED CASES

This is a continuation-in-part of application Ser. No. 08/990,823, filed Dec. 15, 1997, now U.S. Pat. No. 6,228,371, issued May 8, 2001, which is a continuation-in-part of International Application No. PCT/US96/10375, filed Jun. 14, 1996, and claims priority from U.S. Provisional Application No. 60/000,254, filed Jun. 15, 1995, all of which are incorporated herein by reference.

I. BACKGROUND

A. The Rise of Tuberculosis

Over the past few years the editors of the Morbidity and Mortality Weekly Report have chronicled the unexpected rise in tuberculosis cases. It has been estimated that one billion people are infected with M. tuberculosis worldwide, with 7.5 million active cases of tuberculosis. Even in the United States, tuberculosis continues to be a major problem especially among the homeless, Native Americans, African-Americans, immigrants, and the elderly. HIV-infected individuals represent the newest group to be affected by tuberculosis. Of the 88 million new cases of tuberculosis expected in this decade, approximately 10% will be attributable to HIV infection.

The emergence of multi-drug resistant strains of M. tuberculosis has complicated matters further and even raises the possibility of a new tuberculosis epidemic. In the U.S. about 14% of M. tuberculosis isolates are resistant to at least one drug, and approximately 3% are resistant to at least two drugs. M. tuberculosis strains have even been isolated that are resistant to all seven drugs in the repertoire of drugs commonly used to combat tuberculosis. Resistant strains make treatment of tuberculosis extremely difficult: for example, infection with M. tuberculosis strains resistant to isoniazid and rifampin leads to mortality rates of approximately 90% among HIV-infected individuals. The mean time to death after diagnosis in this population is 4–16 weeks. One study reported that, of nine immunocompetent health care workers and prison guards infected with drug-resistant M. tuberculosis, five died. The expected mortality rate for infection with drug-sensitive M. tuberculosis is 0%.

The unrelenting persistence of mycobacterial disease worldwide, the emergence of a new, highly susceptible population, and the recent appearance of drug-resistant strains point to the need for new and better prophylactic and therapeutic treatments of mycobacterial diseases.

B. Tuberculosis and the Immune System

Infection with M. tuberculosis can take on many manifestations. The growth in the body of M. tuberculosis and the pathology that it induces is largely dependent on the type and vigor of the immune response. From mouse genetic studies it is known that innate properties of the macrophage play a large role in containing disease, Skamene, Ref Infect. Dis. 11:S394–S399, 1989. Initial control of M. tuberculosis may also be influenced by reactive T γδ cells. However, the major immune response responsible for containment of M. tuberculosis is via helper T cells (Th1) and to a lesser extent cytotoxic T cells, Kaufmann, Current Opinion in Immunology 3:465–470, 1991. Evidence suggests that there is very little role for the humoral response. The ratio of responding Th1 to Th2 cells has been proposed to be involved in the phenomenon of suppression.

Th1 cells are thought to convey protection by responding to M. tuberculosis T cell epitopes and secreting cytokines, particularly INF-γ, that stimulate macrophages to kill M. tuberculosis. While such an immune response normally clears infections by many facultative intracellular pathogens, such as Salmonella, Listeria, or Francisella, it is only able to contain the growth of other pathogens such as M. tuberculosis and Toxoplasma. Hence, it is likely that M. tuberculosis has the ability to suppress a clearing immune response, and mycobacterial components such as lipoarabinomannan are thought to be potential agents of this suppression. Dormant M. tuberculosis can remain in the body for long periods of time and can emerge to cause disease when the immune system wanes due to age or other effects such as infection with HIV-1.

Historically it has been thought that one needs replicating mycobacteria in order to effect a protective immunization. An hypothesis explaining the molecular basis for the effectiveness of replicating mycobacteria in inducing protective immunity has been proposed by Orme and co-workers, Orme et al., Journal of Immunology 148:189–196, 1992. These scientists suggest that antigens are pinocytosed from the mycobacterial-laden phagosome and used in antigen presentation. This hypothesis also explains the basis for secreted proteins effecting a protective immune response.

Antigens that stimulate T cells from mice infected with M. tuberculosis or from PPD-positive humans are found in both the whole mycobacterial cells and also in the culture supernatants, Orme et al., Journal of Immunology 148:189–196, 1992; Daugelat et al., J. Infect. Dis. 166:186–190, 1992; Barnes et al., J. Immunol. 143:2656–2662, 1989; Collins et al., Infect. Immun. 56:1260–1266, 1988; Lamb et al., Rev. Infect. Dis. 11:S443–S447, 1989; and Hubbard et al., Clin. exp. Immunol. 87: 94–98, 1992. Recently Pal and Horwitz, Infect. Immun. 60:4781–4792, 1992, induced partial protection in guinea pigs by vaccinating with M. tuberculosis supernatant fluids. Similar results were found by Andersen using a murine model of tuberculosis, Andersen, Infection & Immunity 62:2536, 1994. Other studies include Hubbard et al., Clin. exp. Immunol. 87: 94–98, 1992, and Boesen et al., Infection and Immunity 63:1491–1497, 1995. Although these works are far from definitive, they do strengthen the notion that protective epitopes can be found among secreted proteins and that a non-living vaccine can protect against tuberculosis.

II. SUMMARY OF THE INVENTION

For the purposes of vaccine development one needs to find epitopes that confer protection but do not contribute to pathology. An ideal vaccine would contain a cocktail of T-cell epitopes that preferentially stimulate Th1 cells and are bound by different MHC haplotypes. Although such vaccines have never been made, there is at least one example of a synthetic T-cell epitope inducing protection against an intracellular pathogen, Jardim et al., J. Exp. Med. 172:645–648, 1990.

It is an object of this invention to provide M. tuberculosis DNA sequences that encode bacterial peptides having an immunostimulatory activity. Such immunostimulatory peptides will be useful in the treatment, diagnosis, and prevention of tuberculosis.

The present invention provides inter alia, DNA sequences isolated from Mycobacterium tuberculosis. Peptides encoded by these DNA sequences stimulate the production of the macrophage-stimulating cytokine, gamma interferon ("INF-γ"), in mice. Critically, the production of INF-γ by CD4 cells in mice correlates with maximum expression of protective immunity against tuberculosis, Orme et al., *J. Immunology* 151:518–525, 1993. Furthermore, in human patients with active "minimal" or "contained" tuberculosis, it appears that the containment of the disease may be attributable, at least in part, to the production of CD4 Th-1-like lymphocytes that release INF-γ, Boesen et al., *Infection and Immunity* 63:1491–1497, 1995.

Hence, the DNA sequences provided by this invention encode peptides that can of stimulate T-cells to produce INF-γ. That is, these peptides act as epitopes for CD4 T-cells in the immune system. Studies have demonstrated that peptides isolated from an infectious agent and which are shown to be T-cell epitopes can protect against the disease caused by that agent when administered as a vaccine, Mougneau et al., *Science* 268:536–566, 1995 and Jardim et al., *J. Exp. Med* 172:645–648, 1990. For example, T-cell epitopes from the parasite *Leishmania major* have been shown to be effective when administered as a vaccine, Jardim et al., *J. Exp. Med.* 172:645–648, 1990; Mougneau et al., *Science* 268:536–566, 1995; and Yang et al., *J. Immunology* 145:2281–2285, 1990. Therefore, the immunostimulatory peptides (T-cell epitopes) encoded by the DNA sequences according to the invention may be used, in purified form, as a vaccine against tuberculosis.

As noted, the nucleotide sequences of the present invention encode immunostimulatory peptides. In a number of instances, these nucleotide sequences are only a part of a larger open reading frame (ORF) of an *M. tuberculosis* operon. The present invention enables the cloning of the complete ORF using standard molecular biology techniques, based on the nucleotide sequences provided herein. Thus, the present invention encompasses both the nucleotide sequences disclosed herein and the complete *M. tuberculosis* ORFs to which they correspond. However, it is noted that since each of the nucleotide sequences disclosed herein encodes an immunostimulatory peptide, the use of larger peptides encoded by the complete ORFs is not necessary for the practice of the invention. Indeed, it is anticipated that, in some instances, proteins encoded by the corresponding ORFs may be less immunostimulatory than the peptides encoded by the nucleotide sequences provided herein.

According to one aspect of the present invention, immunostimulatory preparations are provided comprising at least one peptide encoded by the DNA sequences presented herein. Such a preparation may include the purified peptide or peptides and one or more pharmaceutically acceptable adjuvants, diluents, and/or excipients.

According to another aspect of the invention, vaccines are provided comprising one or more peptides encoded by nucleotide sequences provided herein. Such a vaccine may include one or more pharmaceutically acceptable excipients, adjuvants, and/or diluents.

According to another aspect of the present invention, antibodies are provided that are specific for immunostimulatory peptides encoded by a nucleotide sequence according to the present invention. Such antibodies may be used to detect the presence of *M. tuberculosis* antigens in medical specimens, such as blood or sputum. Thus, these antigens may be used to diagnose tuberculosis infections.

The present invention also encompasses the diagnostic use of purified peptides encoded by nucleotide sequences according to the present invention. Thus, the peptides may be used in a diagnostic assay to detect the presence of antibodies in a medical specimen, which antibodies bind to the *M. tuberculosis* peptide and indicate that the subject from which the specimen was removed was previously exposed to *M. tuberculosis*.

The present invention also provides improved methods of performing the tuberculin skin test to diagnose exposure of an individual to *M. tuberculosis*. In this improved skin test, purified immunostimulatory peptides encoded by the nucleotide sequences of this invention are employed. Preferably, this skin test is performed with one set of the immunostimulatory peptides, while another set of the immunostimulatory peptides is used to formulate vaccine preparations. In this way, the tuberculin skin test will be useful in distinguishing between subjects infected with tuberculosis and subjects who have simply been vaccinated. In this manner, the present invention may overcome a serious limitation inherent in the present BCG vaccine/tuberculin skin test combination.

Other aspects of the present invention include the use of probes and primers derived from the nucleotide sequences disclosed herein to detect the presence of *M. tuberculosis* nucleic acids in medical specimens.

A further aspect of the present invention is the discovery that a significant proportion of the immunostimulatory peptides is homologous to proteins known to be located in bacterial cell-surface membranes. This discovery suggests that membrane-bound peptides, particularly those from *M. tuberculosis*, may be a new source of antigens for use in vaccine preparations.

III. BRIEF DESCRIPTION OF THE DRAWINGS

FIG. 1 shows the deduced amino acid sequence of the full-length MTB2-92 protein. The nucleic acid sequence is contained within SEQ ID NO: 67, the amino acid sequence is shown in SEQ ID NO: 113.

IV. DESCRIPTION OF THE INVENTION

A. Definitions

Particular terms and phrases used herein have the meanings set forth below.

"Specific binding agent." An agent that binds substantially only to a defined target. Thus, a *Mycobacterium tuberculosis* specific binding agent binds substantially only cellular components derived from *Mycobacterium tuberculosis*. These cellular components include both extracellular and intracellular, proteins, glycoproteins, sugars, and lipids, that are found in *Mycobacterium tuberculosis* isolates. As used herein, the term "*Mycobacterium tuberculosis* specific binding agent" can be an anti-*Mycobacterium tuberculosis* antibody or other agent that binds substantially only to *Mycobacterium tuberculosis*.

The term "anti-*Mycobacterium tuberculosis* antibodies" encompasses monoclonal and polyclonal antibodies that are specific for *Mycobacterium tuberculosis*, i.e., which bind substantially only to *Mycobacterium tuberculosis* when assessed using the methods described below, as well as immunologically effective portions ("fragments") of such antibodies. Immunologically effective portions of the antibodies include Fab, Fab', F(ab')$_2$, Fabc, and Fv portions (for a review, see Better and Horowitz, *Methods Enzymol.*, 178:476–496, 1989). Anti-*Mycobacterium tuberculosis* antibodies may also be produced using standard procedures described in a number of texts, including Harlow and Lane, *Antibodies, A Laboratory Manual*, Cold Spring Harbor Laboratory, 1988.

"Sequence Identity." The similarity between two nucleic acid sequences, or two amino acid sequences is expressed in terms of the level of sequence identity shared between the sequences. Sequence identity is typically expressed in terms of percentage identity; the higher the percentage, the more similar the two sequences are.

Methods of alignment of sequences for comparison are well known in the art. Various programs and alignment algorithms are described in: Smith & Waterman, *Adv. Appl. Math.,* 2:482, 1981; Needleman & Wunsch, *J. Mol. Biol.,* 48:443, 1970; Pearson & Lipman, *Proc. Natl. Acad. Sci. USA,* 85:2444, 1988; Higgins & Sharp, *Gene,* 73:237–244, 1988; Higgins & Sharp, *CABIOS,* 5:151–153, 1989; Corpet et al., *Nucleic Acids Research,* 16:10881–10890, 1988; Huang, et al., *Computer Applications in the Biosciences,* 8:155–165, 1992; and Pearson et al., *Methods in Molecular Biology,* 24:307–331, 1994. Altschul et al., *J. Mol. Biol.,* 215:403–410, 1990, presents a detailed consideration of sequence alignment methods and homology calculations.

The NCBI Basic Local Alignment Search Tool (BLAST™ Altschul et al. *J. Mol. Biol.,* 215:403–410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at http//www.ncbi.nlm.nih.gov/BLAST/. A description of how to determine sequence identity using this program is available at http://www.ncbi.nlm.nih.gov/BLAST/blast_help.html.

For comparisons of amino acid sequences of greater than about 30 amino acids, the "Blast 2 sequences" function in the BLAST program is employed using the default BLOSUM62 matrix set to default parameters, (gap existence cost of 11, and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 45%, at least 50%, at least 60%, at least 80%, at least 85%, at least 90%, or at least 95% sequence identity.

"Isolated." An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

The nucleic acids of the present invention comprise at least a minimum length able to hybridize specifically with a target nucleic acid (or a sequence complementary thereto) under stringent conditions as defined below. The length of a nucleic acid of the present invention is preferably 15 nucleotides or greater in length, although a shorter nucleic acid may be employed as a probe or primer if it is shown to specifically hybridize under stringent conditions with a target nucleic acid by methods well known in the art. The phrase a "peptide of the present invention" means a peptide encoded by a nucleic acid molecule as defined in this paragraph.

"Probes" and "primers." Nucleic acid probes and primers may be readily prepared based on the nucleic acid sequences provided by this invention. A "probe" comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in, Sambrook et al. (ed.), *Molecular Cloning: A Laboratory Manual* 2nd ed., vol. 1–3, Cold Spring Harbor Laboratory Press, Cold Spring Harbor, N.Y., 1989, and Ausubel et al. (ed.); *Current Protocols in Molecular Biology,* Greene Publishing and Wiley-Interscience, New York (with periodic updates), 1987.

"Primers." Primers are short nucleic acids, preferably DNA oligonucleotides 15 nucleotides or more in length, that are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

As noted, probes and primers are preferably 15 nucleotides or more in length, but, to enhance specificity, probes and primers of 20 or more nucleotides may be preferred.

Methods for preparing and using probes and primers are described, for example, in Sambrook et al. (ed.), *Molecular Cloning: A Laboratory Manual* 2nd ed., vol. 1–3, Cold Spring Harbor Laboratory Press, Cold Spring Harbor, N.Y., 1989; Ausubel et al. (ed.), *Current Protocols in Molecular Biology,* Greene Publishing and Wiley-Interscience, New York (with periodic updates), 1987; and Innis et al., *PCR Protocols: A Guide to Methods and Applications,* Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.).

"Substantial similarity." A first nucleic acid is "substantially similar" to a second nucleic acid if, when optimally aligned (with appropriate nucleotide insertions or deletions) with the second nucleic acid (or its complementary strand), there is nucleotide sequence identity in at least about 75%–90% of the nucleotide bases, and preferably greater than 90% of the nucleotide bases. ("Substantial sequence complementarity" requires a similar degree of sequence complementarity.) Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

"Operably linked." A first nucleic acid sequence is "operably" linked with a second nucleic acid sequence whenever the first nucleic acid sequence is placed in a functional relationship with the nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

"Recombinant." A "recombinant" nucleic acid has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

"Stringent Conditions" and "Specific." The nucleic acid probes and primers of the present invention hybridize under stringent conditions to a target DNA sequence, e.g., to a full length *Mycobacterium tuberculosis* gene that encodes an immunostimulatory peptide.

The term "stringent conditions" is functionally defined with regard to the hybridization of a nucleic-acid probe to a target nucleic acid (i.e., to a particular nucleic acid sequence of interest) by the hybridization procedure discussed in Sambrook et al. (ed.), *Molecular Cloning: A Laboratory Manual* 2nd ed., vol. 1–3, Cold Spring Harbor Laboratory Press, Cold Spring Harbor, N.Y., 1989, at pages 9.52–9.55, 9.47–9.52 and 9.56–9.58; Kanehisa, *Nuc. Acids Res.* 12:203–213, 1984; and Wetmur et al., *J. Mol. Biol.* 31:349–370, 1968.

Nucleic-acid hybridization is affected by such conditions as salt concentration, temperature, or organic solvents, in addition to the base composition, length of the complementary strands, and the number of nucleotide-base mismatches between the hybridizing nucleic acids, as will be appreciated readily by those skilled in the art.

In preferred embodiments of the present invention, stringent conditions are those under which DNA molecules with more than 25% sequence variation (also termed "mismatch") will not hybridize. Such conditions are also referred to as conditions of 75% stringency (since hybridization will occur only between molecules with 75% sequence identity or greater). In more preferred embodiments, stringent conditions are those under which DNA molecules with more than 15% mismatch will not hybridize (conditions of 85% stringency). In most preferred embodiments, stringent conditions are those under which DNA molecules with more that 10% mismatch will not hybridize (i.e., conditions of 90% stringency).

When referring to a probe or primer, the term "specific for (a target sequence)" indicates that the probe or primer hybridizes under stringent conditions substantially only to the target sequence in a given sample comprising the target sequence.

"Purified." A "purified" peptide is a peptide that has been extracted from the cellular environment and separated from substantially all other cellular peptides. As used herein, the term "peptide" includes peptides, polypeptides and proteins. In preferred embodiments, a "purified" peptide is a preparation in which the subject peptide comprises 80% or more of the protein content of the preparation. For certain uses, such as vaccine preparations, even greater purity may be necessary. "Immunostimulatory." The phrase "immunostimulatory peptide" as used herein refers to a peptide that is capable of stimulating INF-γ production in the assay described in section B.5. below. In preferred embodiments, an immunostimulatory peptide is capable of inducing greater than twice the background level of this assay determined using T-cells stimulated with no antigens or negative control antigens. Preferably, the immunostimulatory peptides are capable of inducing more than 0.01 ng/mL of INF-γ in this assay system. In more preferred embodiments, an immunostimulatory peptide is one capable of inducing greater than 10 ng/mL of INF-γ in this assay system.

B. Materials and Methods

1. Standard Methodologies

The present invention utilizes standard laboratory practices for the cloning, manipulation, and sequencing of nucleic acids, purification and analysis of proteins, and other molecular biological and biochemical techniques, unless otherwise stipulated. Such techniques are explained in detail in standard laboratory manuals such as Sambrook et al. (ed.), *Molecular Cloning: A Laboratory Manual* 2nd ed., vol. 1–3, Cold Spring Harbor Laboratory Press, Cold Spring Harbor, N.Y., 1989, and Ausubel et al. (ed.), *Current Protocols in Molecular Biology*, Greene Publishing and Wiley-Interscience, New York (with periodic updates), 1987.

Methods for chemical synthesis of nucleic acids are discussed, for example, in Beaucage et al., *Tetra. Letts.* 22:1859–1862, 1981, and Matteucci et al., *J. Am. Chem. Soc.* 103:3185, 1981. Chemical synthesis of nucleic acids can be performed, for example, on commercial automated oligonucleotide synthesizers.

2. Isolation of *Mycobacterium tuberculosis* DNA Sequences Encoding Immunostimulatory Proteins

*Mycobacterium tuberculosis* DNA was obtained by the method of Jacobs et al., *Methods In Enzymology* 204:537–555, 1991. Samples of the isolated DNA were partially digested with one of the following restriction enzymes HinPI, HpaII, AciI, TaqI, BsaHI, and NarI. Digested fragments of 2–5 kb were purified from agarose gels and then ligated into the BstBI site in front of the truncated phoA gene in one or more of the three phagemid vectors pJDT1, pJDT2, and pJDT3.

A schematic representation of the phagemid vector pJDT2 is provided in Mdluli et al., *Gene* 155:133–134, 1995. The pJDT vectors were specifically designed for cloning and selecting genes encoding cell wall-associated, cytoplasmic membrane associated, periplasmic, or secreted proteins (and especially for cloning such genes from GC-rich genomes, such as the Mycobacterium tuberculosis genome). The vectors have a BstBI cloning site in frame with the bacterial alkaline phosphatase gene (phoA) such that cloning of an in-frame sequence into the cloning site will result in the production of a fusion protein. The phoA gene encodes a version of the alkaline phosphatase that lacks a signal sequence; hence, only if the DNA cloned into the BstBI site includes a signal sequence or a transmembrane sequence can the fusion protein be secreted to the medium or inserted into cytoplasmic membrane, periplasm, or cell wall. Those clones encoding such fusion proteins may be detected by plating clones on agar plates containing the indicator 5-bromo-4-chloro-3-indolyl phosphate (XP). Alkaline phosphatase cleaves XP to release a blue-colored product. Hence, those clones containing alkaline phosphatase fusion proteins with the enzymatic portion lying outside the cytoplasmic membrane will produce the blue color.

The three vectors in this series (pJDT1, pJDT2, and pJDT3) have the BstBI restriction sites located in different reading frames with respect to the phoA gene. This increases the likelihood of cloning any particular gene in the correct orientation and reading frame for expression by a factor of three. Mdluli et al., *Gene* 155:133–134, 1995, describes pJDT vectors in detail.

3. Selection of Secreted Fusion Proteins

The recombinant clones described above were transformed into *E. coli* and plated on agar plates containing the indicator 5-bromo-4-chloro-3-indolyl phosphate. Production of blue pigmentation, produced as a result of the action of alkaline phosphatase on the indicator, indicated the presence of secreted cytoplasmic membrane periplasmic, cell wall-associated, or outer membrane fusion proteins (because the bacterial alkaline phosphatase gene in the vector lacks a signal sequence and could not otherwise escape the bacterial cell). A similar technique has been used to identify *M. tuberculosis* genes encoding exported proteins by Lim et al., *J. Bact.* 177:59–65, 1995.

Those clones producing blue pigmentation were picked and grown in liquid culture to facilitate the purification of the alkaline phosphatase fusion proteins. These recombinant clones were designated according to the restriction enzyme used to digest the *Mycobacterium tuberculosis* DNA (thus, clones designated A#2-1, A#2-2, etc., were produced using *Mycobacterium tuberculosis* DNA digested with AciI).

4. Purification of Secreted Fusion Proteins

PhoA fusion proteins were extracted from the selected *E. coli* clones by cell lysis and purified by SDS polyacrylamide gel electrophoresis. Essentially, individual *E. coli* clones were grown overnight at 30° C. with shaking in 2 mL LB broth containing ampicillin, kanamycin, and IPTG. The cells were precipitated by centrifugation and resuspended in 100 µL Tris-EDTA buffer. To this mixture was added 100 µL lysis buffer (1% SDS, 1 mMEDTA, 25 mM DTT, 10% glycerol and 50 mM tris-HCl, pH 7.5). DNA released from the cells was sheared by passing the mixture through a small-gauge syringe needle. The sample was then heated for 5 minutes at 100° C. and loaded onto an SDS PAGE gel (12 cm×14 cm×1.5 mm, made with 4% (w/v) acrylamide in the stacking section and 10% (w/v) acrylamide in the separating section). Several samples from each clone were loaded onto each gel.

The samples were electrophoresed by application of 200 volts to the gel for 4 hours. Subsequently, the proteins were transferred to a nitrocellulose membrane by Western blotting. A strip of nitrocellulose was cut off to be processed with antibody, and the remainder of the nitrocellulose was set aside for eventual elution of the protein. The strip was incubated with blocking buffer and then with anti-alkaline phosphatase primary antibody, followed by incubation with anti-mouse antibody conjugated with horseradish peroxidase. Finally, the strip was developed with the NEN DuPont Renaissance™ kit to generate a luminescent signal. The migratory position of the PhoA fusion protein, as indicated by the luminescent label, was measured with a ruler, and the corresponding region of the undeveloped nitrocellulose blot was excised.

This region of nitrocellulose containing the PhoA fusion protein was then incubated in 1 mL 20% acetonitrile at 37° C. for 3 hours. Subsequently, the mixture was centrifuged to remove the nitrocellulose, and the liquid was transferred to a new test tube and lyophilized. The resulting protein pellet was dissolved in 100 µL of endotoxin-free, sterile water and precipitated with acetone at −20° C. After centrifugation the bulk of the acetone was removed and the residual acetone was allowed to evaporate. The protein pellet was re-dissolved in 100 µL of sterile phosphate buffered saline.

This procedure can be scaled up by modification to include IPTG induction 2 hours prior to cell harvesting, washing nitrocellulose membranes with PBS prior to acetonitrile extraction, and lyophilization of acetonitrile-extracted and acetone-precipitated protein samples.

5. Determination of Immunostimulatory Capacity in Mice

The purified alkaline phosphatase—*Mycobacterium tuberculosis* fusion peptides encoded by the recombinant clones were then tested for their ability to stimulate INF-γ production in mice. The test used to determine INF-γ stimulation was essentially as described by Orme et al., *J. Immunology* 151:518–525, 1993.

Essentially, the assay method is as follows: The virulent strain *M. tuberculosis* Erdman is grown in Proskauer Beck medium to mid-log phase, then aliquoted and frozen at −70° C. for use as an inoculant. Cultures of this bacterium are grown and harvested, and mice are inoculated with $1\times10^5$ viable bacteria suspended in 200 μL sterile saline via a lateral tail vein on the first day of the test.

Bone marrow-derived macrophages are used in the test to present the bacterial alkaline phosphatase-*Mycobacterium tuberculosis* fusion protein antigens. These macrophages are obtained by harvesting cells from mouse femurs and culturing the cells in Dulbecco's modified Eagle medium as described by Orme et al., *J. Immunology* 151:518–525, 1993. Eight to ten days later, up to ten μg of the fusion peptide to be tested is added to the macrophages, and the cells are incubated for 24 hours.

The CD4 cells are obtained by harvesting spleen cells from the infected mice and then pooling and enriching for CD4 cells by removal of adherent cells by incubation on plastic Petri dishes, followed by incubation for 60 minutes at 37° C. with a mixture of J11d.2, Lyt-2.43, and GL4 monoclonal antibody (mAb) in the presence of rabbit complement to deplete B cells and immature T cells, CD8 cells, and γδ cells, respectively. The macrophages are overlaid with $10^6$ of these CD4 cells, and the medium is supplemented with 5 U interleukin-2 (IL-2) to promote continued T cell proliferation and cytokine secretion. After 72 hours, cell supernatants are harvested from sets of triplicate wells and assayed for cytokine content.

Cytokine levels in harvested supernatants are assayed by sandwich ELISA as described by Orme et al., *J. Immunology* 151:518–525, 1993.

6. Determination of Immunostimulatory Capacity in Humans

The purified alkaline phosphatase—*Mycobacterium tuberculosis* fusion peptides encoded by the recombinant clones or by synthetic peptides are tested for their ability to induce INF-γ production by human T cells in the following manner.

Blood from tuberculin-positive people (producing a tuberculin-positive skin test) is collected in EDTA-coated tubes to prevent clotting. Mononuclear cells are isolated using a modified version of the separation procedure provided with the NycoPrep™ 1.077 solution (Nycomed Pharma AS, Oslo, Norway). Briefly, the blood is diluted in an equal volume of a physiologic solution, such as Hanks Balanced Salt solution (HBSS), and then gently layered atop the Nycoprep solution in a 2-to-1 ratio in 50 mL tubes. The tubes are centrifuged at 800×g for 20 minutes, and the mononuclear cells are then removed from the interface between the Nycoprep solution and the sample layer. The plasma is removed from the top of the tube and filtered through a 0.2-micron filter. The plasma is then added to the tissue culture media. The mononuclear cells are washed twice by a procedure in which the cells are diluted in a physiologic solution, such as HBSS or RPMI 1640, and centrifuged at 400×g for 10 minutes. The mononuclear cells are then resuspended to the desired concentration in tissue culture media (RPMI 1640 containing 10% autologous serum, HEPES, non-essential amino acids, antibiotics and polymixin B). The mononuclear cells are then cultured in 96-well microtitre plates.

Peptides or PhoA fusion proteins are then added to individual wells in the 96-well plate, and cells are then placed in an incubator (37° C., 5% $CO_2$). Samples of the supernatants (tissue culture media from the wells containing the cells) are collected at various time points (from 3 to 8 days) after the addition of the peptides or PhoA fusion proteins. The immune responsiveness of T cells to the peptides and PhoA fusion proteins is assessed by measuring the production of cytokines (including INF-γ).

Cytokines are measured using an Enzyme Linked Immunosorbent Assay (ELISA), the details of which are described in the Cytokine ELISA Protocol in the PharMingen catalog (PharMingen, San Diego, Calif.). To measure the presence of human INF-γ, wells of a 96-well microtitre plate are coated with a "capture antibody" (e.g., anti-human INF-γ antibody). The sample supernatants are then added to individual wells. Any INF-γ present in the sample binds to the capture antibody. The wells are then washed. A "detection antibody" (e.g., anti-human INF-γ antibody), conjugated to biotin, is added to each well, and binds to any INF-γ bound to the capture antibody. Any unbound detection antibody is washed away. An avidin-linked horseradish peroxidase enzyme is added to each well (avidin binds tightly to the biotin on the detection antibody). Any excess unbound enzyme is washed away. Finally, a chromogenic substrate for the enzyme is added and the intensity of the colour reaction that occurs is quantified using an ELISA plate reader. The amount of the INF-γ in the sample supernatants is determined by comparison with a standard curve using known amounts of humans INF-γ.

Measurement of other cytokines, such as IL-2 and interleukin-4 (IL-4), can be determined using the same protocol, with the appropriate substitution of reagents (monoclonal antibodies and standards).

7. DNA Sequencing

The sequencing of the alkaline phosphatase fusion clones was undertaken using the AmpliCycle™ thermal sequencing kit (Perkin Elmer, Applied Biosystems Division, 850 Lincoln Centre Drive, Foster City, Calif. 94404, U.S.A.), using a primer designed to read out of the alkaline phosphatase gene into the *Mycobacterium tuberculosis* DNA insert, or primers specific to the cloned sequences.

C. Results

1. Immunostimulatory Capacity

More than 300 fusion clones were tested for their ability to stimulate INF-γ production. Of these, 80 clones initially were designated to have some ability to stimulate INF-γ production. Tables 1 and 2 show the data obtained for these 80 clones. Clones listed in Table 1 showed the greatest ability to stimulate INF-γ production (greater than 10 ng/mL of INF-γ), while clones listed in Table 2 stimulated the production of between 2 ng/mL and 10 ng/mL of INF-γ. Background levels of INF-γ production (i.e., levels produced without any added *M. tuberculosis* antigen) were subtracted from the levels produced by the fusions to obtain the figures shown in these tables.

TABLE 1

Immunustimulatory AP-fusion clones

| SEQ ID NO: | Name | INF | Sanger ID of Mtb gene | Functional Identification |
|---|---|---|---|---|
| 2 | AciI#1-152 | >40,000 | MTCY16By.09 | glycerol-3-phosphate binding periplasmic protein precursor |
| 4 | AciI#1-247 | >40,000 | MTCI364.18 | fatty acid transport protein |
| 65, 66 | AciI#1-264 | >40,000 | MTCY78.03c | unknown |
| 62 | AciI#1-435 | >40,000 | MTCY13D12.28 | EmbA |
| 75 | HinP#1-27 | >20,000 | MTV023.04c | |
| 67 | HinP#2-92 | >20,000 | MTCY190.11c | cytochrome c oxidase subunit II |
| 110 | HinP#2-145 | >20,000 | MTV018.38c | |
| 52 | HinP#2-150 | >20,000 | MTCY190.11c | COXII (same as 2-92) |
| 48 | HinP#1-200 | >20,000 | MTV003.08 | |
| 54 | HinP#3-30 | >20,000 | MTCY19H5.30c | |
| 6 | AciI#2-2 | >20,000 | MTV003.10c | lipoprotein, penicillin binding protein |

TABLE 1-continued

Immunustimulatory AP-fusion clones

| SEQ ID NO: | Name | INF | Sanger ID of Mtb gene | Functional Identification |
|---|---|---|---|---|
| 7 | AciI#2-23 | >20,000 | MTCY13E10.15c | |
| 11 | AciI#2-506 | >20,000 | MTCY253.27c | -glutamyl transpeptidase precursor |
| 13 | AciI#2-511 | >20,000 | MTCY50.08c | unknown |
| 15 | AciI#2-639 | >20,000 | MTCY02B12.02 | unknown |
| 16 | AciI#2-822 | >20,000 | MTV004.48 | unknown |
| 68 | AciI#2-823 | >20,000 | MTCY77.20 | unknown membrane protein |
| 61 | AciI#2-825 | >20,000 | MTCY31.03c | |
| 71 | AciI#2-827 | >20,000 | MTCY01B2.15c | cytochrome d (ubiquinol) oxidase (appC) |
| 22 | AciI#2-898 | >20,000 | MTV005.02 | |
| 27 | AciI#2-1084 | >20,000 | MTV023.03c | |
| 34 | AciI#3-47 | >20,000 | MTCY50.02 | oppA-like |
| 36 | AciI#3-133 | >20,000 | MTCY22G8 | complement of ORF designated |
| 38 | AciI#3-166 | >20,000 | MTCY20H10.03 | unknown/contains potential membrane spanning region |
| 39 | AciI#3-167 | >20,000 | MTC128.14 | unknown |
| 41 | AciI#3-206 | >20,000 | MTCY270.17 | ftsQ |
| 69 | HinP#1-31 | 14,638 | MTV025.111 | 19kDa Antigen |
| 47 | HinP#1-144 | 13,546 | MTC128.11 | unknown |
| 70 | HinP#1-3 | 11,550 | MTV023.04c | same as HinP1-27 |
| 111 | AciI#1-486 | 11,416 | MTCY13D12.26 | embC (LysR family) |
| 5 | AciI#1-426 | 11,135 | MTV025.013c | dppB (peptide transport permease) |
| 23 | AciI#2-916 | 10,865 | MTCY21D4.03c | unknown (signal peptide) |

Abbreviations:
INF: pg/mL of INF-γ produced using fusion to stimulate immune T-cells. Sanger/TGIR ID of *M. tuberculosis* gene: matches produced from BLAST search of TIGR and Sanger Center databases. For Sanger matches, the information prior to the decimal point (e.g., MTCY21D4) identifies the cosmid clone and the numbers after the decimal point (e.g., .03) indicate the matching ORF within that cosmid; "c": indicates that the clone matched with the complement of that cosmid ORF sequence.

TABLE 2

Immunostimulatory AP-fusion clones

| SEQ ID NO: | Clone Name | INF | Sanger/ TIGR ID of Mtb gene | Functional Identification |
|---|---|---|---|---|
| 1 | AciI#1-62 | 3,126 | MTCY190.11c | COXII (same as 2-92) |
| 8 | AciI#2-26 | 3,089 | MTV023.02c | |
| 9 | AciI#2-35 | 3,907 | MTV023.05c | |
| 76 | AciI#2-147 | 5,464 | | same as H2-147 or H1-200 |
| 12 | AciI#2-508 | 7,052 | MTCY20G9.23 | |
| 14 | AciI#2-523 | 2,479 | MTCY427.10c | unknown |
| 72 | AciI#2-834 | 5,942 | MTV016.33c | |
| 17 | AciI#2-854 | 5,560 | MTCY339.08c | unknown |
| 18 | AciI#2-872 | 2,361 | MTCY22D7.18c | cstA-like |
| 73 | AciI#2-874 | 2,171 | MTCY190.20 | membrane protein |
| 19 | AciI#2-884D | 2,729 | MTCY21D4.03c | |
| 21 | AciI#2-894 | 3,396 | MTV002.33c | PPE family |
| 24 | AciI#2-1014 | 6,302 | MTCY21D4.03C | same as 2-916 |
| 74 | AciI#2-1018 | 4,642 | MTCY270.11 | MURF |
| 25 | AciI#2-1025 | 3,582 | MTCY359.10 | unknown membrane protein |
| 26 | AciI#2-1035 | 3,454 | MTCY04D9.11c | similar to penicillin binding proteins |

TABLE 2-continued

Immunostimulatory AP-fusion clones

| SEQ ID NO: | Clone Name | INF | Sanger/ TIGR ID of Mtb gene | Functional Identification |
|---|---|---|---|---|
| 28 | AciI#2-1089 | 8,974 | MTCY39.39 | mpt 64 |
| 29 | AciI#2-1090 | 7,449 | MTCY04C12.18c | unknown membrane protein |
| 30 | AciI#2-1104 | 5,148 | MTCY359.13 | Precursor of Apa wag43 locus |
| 31 | AciI#3-9 | 3,160 | MTCY164.01 | Unknown |
| 32 | AciI#3-12 | 3,891 | MTV003.10c | penicillin binding protein |
| 33 | AciI#3-15 | 4,019 | MTCY20H10.03 | |
| 35 | AciI#3-78 | 2,905 | MTC128.14 | same as A3-167 |
| 37 | AciI#3-134 | 3,895 | MTCY22G8.04 | same as A3-133 |
| 40 | AciI#3-204 | 4,774 | MTCY50.02 | same as A3-47 |
| 42 | AciI#3-214 | 7,333 | MTCY33.38 | unknown |
| 112 | AciI#3-243 | 2,857 | MTCY50.02 | |
| 43 | AciI#3-281 | 2,943 | MTCY19H5.32c | |
| 44 | Bsa HI#1-21 | 8,122 | *M. bovis* clone | |
| 45 | HinP#1-12 | 2,905 | MTCY49.31c | unknown |
| 49 | HinP#2-23 | 2,339 | MTCY0033.38 | same as A30214 |
| 46 | HinP#1-142 | 6,258 | MTCY02B10.27c | unknown |
| 50 | HinP#2-143 | 3,689 | MTCY274.09c | unknown, thioredoxin-like |
| 51 | HinP# 2-145A | 2,314 | | |
| 53 | HinP#3-28 | 2,980 | MTV009.03c | LppS |
| 55 | HinP#3-34 | 2,564 | MTCY25D10.07 | unknown |
| 56 | HinP#3-41 | 3,296 | P31953 P31952 P17944 | Antigen 85c, 85b & 85a precursor |
| 57 | HpaII#1-3 | 2,360 | MTCY190.11c | COXII |
| 58 | HpaII#1-8 | 2,048 | MTCY432 | unknown |
| 59 | HpaII#1-10 | 4,178 | MTCY39.39 | same as A2-1089 |
| 60 | HpaII#1-13 | 3,714 | MTCY16B7.47 | unknown partial ORF |

Abbreviations:
INF: pg/mL of INF-γ produced using fusion to stimulate immune T-cells.
Sanger/TGIR ID of *M. tuberculosis* gene: matches produced from BLAST search of TIGR and Sanger Center databases. For Sanger matches, the information prior to the decimal point (e.g., MTCY21D4) identifies the cosmid clone and the numbers after the decimal point (e.g., .03) indicate the matching ORF within that cosmid; "c" indicates that the clone matched with the complement of that cosmid ORF sequence.

2. DNA Sequencing and Determination of Open Reading Frames

DNA sequence data for the sequences of the *Mycobacterium tuberculosis* DNA present in the clones shown in Tables 1 and 2 are shown in the accompanying Sequence Listing. The sequences are believed to represent the respective coding strands of the Mycobacterium DNA. In most instances, these sequences represent only partial sequences of the respective immunostimulatory peptides and, in turn, only partial sequences of respective *Mycobacterium tuberculosis* genes. However, each of the clones from which these sequences were derived encodes, by itself, at least one immunostimulatory T-cell epitope. As discussed in part V, below, one of ordinary skill in the art, given the information provided herein, readily can obtain the immunostimulatory peptides and corresponding full-length *M. tuberculosis* genes using standard techniques. Accordingly, the nucleotide sequences of the present invention encompass not only those respective sequences presented in the sequence listings, but also the respective complete nucleotide sequence encoding the respective immunostimulatory peptides as well as the corresponding *M. tuberculosis* genes. The nucleotide abbreviations employed in the sequence listings are as follows in Table 3:

TABLE 3

| Symbol | Meaning |
|---|---|
| A | A; adenine |
| C | C; cytosine |
| G | G; guanine |
| T | T; thymine |
| U | U; uracil |
| M | A or C |
| R | A or G |
| W | A or T/U |
| S | C or G |
| Y | C or T/U |
| K | G or T/U |
| V | A or C or G; not T/U |
| H | A or C or T/U; not G |
| D | A or g or T/U; not C |
| B | C or g or T/U; not A |
| N | (A or C or g or T/U) or (unknown or other or no base) |
| — | indeterminate (indicates an unreadable sequence compression) |

The DNA sequences obtained were then analyzed with respect to the G+C content as a function of codon position over a window of 120 codons using the 'FRAME' computer program, Bibb et al., *Gene* 30: 157–166, 1984. This program uses the bias of these nucleotides for each of the codon positions to identify the correct reading frame. As shown in Tables 1 and 2, the sequences were also analyzed using the BLAST™ program on the TIGR™ database at the NCBI website (http://www.ncbi.gov/cgi-bin/BLAST/nph-tigrb1) and the Sanger Center website database (http://www/sanger.ac.uk/Projects/M_tuberculosis/blast_server.shtml). These sequence comparisons permitted identification of matches with reported sequences to be identified and, for matches on the Sanger database, the identification of the open reading frame.

The sequence information revealed that a number of the clones contained an number of potentially overlapping sequences or sequences from the same gene, as noted below:

| Clone | Overlapping Sequence(s) |
|---|---|
| HinP#1-27 | HinP#1-3 |
| HinP#2-92 | HinP#2-150, Aci#1-62, HpaII#1-3 |
| HinP#1-200 | AciI#2-147, H#2-147 |
| AciI#2-639 | AciI#2-676 |
| AciI#3-47 | AciI#3-204, AciI#3-243 |
| AciI#3-133 | AciI#3-134 |
| AciI#3-166 | AciI#3-15 |
| AciI#3-167 | AciI#3-78 |
| AciI#2-916 | AciI#2-1014 |
| AciI#2-1089 | HpaII#1-10 |
| AciI#3-243 | AciI#3-47, AciI#3-204 |
| Hinp#2-23 | AciI#3-214 |

3. Identification of T Cell Epitopes in the Immunostimulatory Peptides

The "T-Site" program, by Feller, D. C. and de la Cruz, V. F., MedImmune Inc., 19 Firstfield Rd., Gaithersburg, Md. 20878, U.S.A., was used to predict T-cell epitopes from the determined coding sequences. The program uses a series of four predictive algorithms. In particular, peptides were designed against regions indicated by the algorithm "A" motif which predicts alpha-helical periodicity, Margalit et al., *J. Immunol.* 138:2213, 1987, and amphipathicity. Peptides were also designed against regions indicated by the algorithm "R" motif which identifies segments that display a similarity to motifs known to be recognized by MHC class I and class II molecules, Rothbard and Taylor, *EMBO J.* 7:93, 1988. The other two algorithms identify classes of T-cell epitopes recognized in mice.

4. Synthesis of Synthetic Peptides Containing T Cell Epitopes in Identified Immunostimulatory Peptides A series of staggered peptides were designed to overlap regions indicated by the T-site analysis. These were synthesized by Chiron Mimotopes Pty. Ltd. (11055 Roselle St., San Diego, Calif. 92121, U.S.A.).

Peptides designed from sequences described in this application include:

| Peptide Sequence | Peptide Name | SEQ ID NO: |
|---|---|---|
| HinP#1-200 (6 peptides) | | |
| VHLATGMAETVASFSPS | HPI1-200/2 | 77 |
| REVVHLATGMAETVASF | HPI1-200/3 | 78 |
| RDSREVVHLATGMAETV | HPI1-200/4 | 79 |
| DFNRDSREVVHLATGMA | HPI1-200/5 | 80 |
| ISAAVVTGYLRWTTPDR | HPI1-200/6 | 81 |
| AVVFLCAAAISAAVVTG | HPI1-200/7 | 82 |
| AciI#2-827 (14 peptides) | | |
| VTDNPAWYRLTKFFGKL | CD-2/1/96/1 | 83 |
| AWYRLTKFFGKLFLINF | CD-2/1/96/2 | 84 |
| KFFGKLFLINFAIGVAT | CD-2/1/96/3 | 85 |
| FLINFAIGVATGIVQEF | CD-2/1/96/4 | 86 |
| AIGVATGIVQEFQFGMN | CD-2/1/96/5 | 87 |
| TGIVQEFEFGMNWSEYS | CD-2/1/96/6 | 88 |
| EFQFGMNWSEYSRFVGD | CD-2/1/96/7 | 89 |
| MNWSEYSRFVGDVFGAP | CD-2/1/96/8 | 90 |
| WSEYSRFVGDVFGAPLA | CD-2/1/96/9 | 91 |
| EYSRFVGDVFGAPLAME | CD-2/1/96/10 | 92 |
| SRFVGDVFGAPLAMESL | CD-2/1/96/11 | 93 |
| WIFGWNRLPRLVHLACI | CD-2/1/96/12 | 94 |
| WNRLPRLVHLACIWIVA | CD-2/1/96/13 | 95 |
| GRAELSSIVVLLTNNTA | CD-2/1/96/14 | 96 |
| HinP#1-3 (2 peptides) | | |
| GKTYDAYFTDAGGITPG | HPI1-3/2 | 97 |
| YDAYFTDAGGITPGNSV | HPI1-3/3 | 98 |
| HinP#1-3/HinP#1-200 combined peptides | | |
| WPQGKTYDAYFTDAGGI (HinP#1-3) | HPI1-3/1 (combined) | 99 |
| ATGMAETVASFSPSEGS (HinP#1-200) | | 100 |
| AciI#2-823 (1 peptide) | | |
| GWERRLRHAVSPKDPAQ | AI2-823/1 | 101 |
| HinP#1-31 (4 peptides) | | |
| TGSGETTTAAGTTASPG | HPI1-31/1 | 102 |
| GAAILVAGLSGCSSNKS | HPI1-31/2 | 103 |
| AVAGAAILVAGLSGCSS | HPI1-31/3 | 104 |
| LTVAVAGAAILVAGLSG | HPI1-31/4 | 105 |

These synthetic peptides were resuspended in phosphate-buffered saline to be tested to confirm their ability to function as T cell epitopes using the procedure described in part IV(B)(6), above.

5. Confirmation of Immunostimulatory Capacity Using T Cells from Tuberculosis Patients The synthetic peptides described above, along with a number of the PhoA fusion proteins shown to be immunostimulatory in mice, were tested for their ability to stimulate production of INF-γ in T-cells from tuberculin-positive people using the methods described in part IV(B)(6), above. For each assay, $5\times10^5$ mononuclear cells were stimulated with up to 1 μg/mL *M. tuberculosis* peptide or up to 50 ng/mL PhoA fusion protein. *M. tuberculosis* filtrate proteins, Con A and PHA, were employed as positive controls. An assay was run with medium alone to determine background levels, and PhoA protein was employed as a negative control.

The results, shown in Table 4 below, indicate that all of the peptides tested stimulated INF-γ production from T-cells of a particular subject.

TABLE 4

| Peptide or PhoA Fusion Protein Name | Concentration of INF-γ (pg/mL) | Concentration of INF-γ minus background (pg/mL) |
|---|---|---|
| CD-2/1/96/1 | 256.6 | 153.3 |
| CD-2/1/96/9 | 187.6 | 84.3 |
| CD-2/1/96/10 | 134.0 | 30.7 |
| CD-2/1/96/11 | 141.6 | 38.3 |
| CD-2/1/96/14 | 310.2 | 206.9 |
| HPI1-3/2 | 136.3 | 23.0 |
| HPI1-3/3 | 264.2 | 160.9 |
| AciI 2-898 | 134.0 | 30.7 |
| AciI 3-47 | 386.8 | 283.5 |
| *M. tuberculosis* filtrate proteins (10 μg/mL) | 256.6 | 153.3 |
| *M. tuberculosis* filtrate proteins (5 μg/mL) | 134.0 | 30.7 |
| Con A (10 μg/mL) | 2839 | 2735.7 |
| PHA (1%) | 10378 | 10274.7 |
| PhoA control (10 μg/mL) | 26.7 | 0 |
| Background | 103.3 | 0 |

V. CLONING OF FULL-LENGTH *MYCOBACTERIUM TUBERCULOSIS* ORFs CONTAINING T-CELL EPITOPES

Most the sequences presented represent only part of a larger *M. tuberculosis* ORF. If desired, the full-length *M. tuberculosis* ORFs that include these provided nucleotide sequences can be readily obtained by one of ordinary skill in the art, based on the sequence data provided herein.

A. General Methodologies

Methods for obtaining full-length genes based on partial sequence information are standard in the art and are particularly simple for prokaryotic genomes. By way of example, the full-length ORFs corresponding to the DNA sequences presented herein may be obtained by creating a library of *Mycobacterium tuberculosis* DNA in a plasmid, bacteriophage, or phagemid vector and screening this library with a hybridization probe using standard colony hybridization techniques. The hybridization probe consists of an oligonucleotide derived from a DNA sequence according to the present invention labeled with a suitable marker to enable detection of hybridizing clones. Suitable markers include radio nucleotides, such as $^{32}P$ and non-radioactive markers such as biotin-avidin enzyme linked systems. Methods for constructing suitable libraries, production and labeling of oligonucleotide probes, and colony hybridization are standard laboratory procedures and are described in standard laboratory manuals such as in Sambrook et al. (ed.), *Molecular Cloning: A Laboratory Manual*, 2nd ed., vol. 1–3, Cold Spring Harbor Laboratory Press, Cold Spring Harbor, N.Y., 1989, and Ausubel et al. (ed.), *Current Protocols in Molecular Biology*, Greene Publishing and Wiley-Interscience, New York (with periodic updates), 1987.

Having identified a clone that hybridizes with the oligonucleotide, the clone is identified and sequenced using standard methods such as described in Chapter 13 of reference Sambrook et al. (ed.), *Molecular Cloning: A Laboratory Manual*, 2nd ed., vol. 1–3, Cold Spring Harbor Laboratory Press, Cold Spring Harbor, N.Y., 1989. Determination of the translation-initiation point of the DNA sequence enables the ORF to be located.

An alternative approach to cloning the full-length ORFs corresponding to the DNA sequences provided herein is the use of the polymerase chain reaction (PCR). In particular, the inverse polymerase chain reaction (IPCR) is useful to isolate DNA sequences flanking a known sequence. Methods for amplifying of flanking sequences by IPCR are described in Chapter 27 of Innis et al., *PCR Protocols: A Guide to Methods and Applications*, Academic Press, San Diego, 1990, and in Earp et al., *Nucleic Acids Research* 18:3721–3729, 1990.

Accordingly, the present invention encompasses small oligonucleotides included in the DNA sequences presented in the respective Sequence Listings. These small oligonucleotides are useful as hybridization probes and PCR primers that can be employed to clone the corresponding full-length *Mycobacterium tuberculosis* ORFs. In preferred embodiments, these oligonucleotides will comprise at least 15 contiguous nucleotides of a DNA sequence set forth in the Sequence Listing, and in more preferred embodiments, such oligonucleotides will comprise at least 20 contiguous nucleotides of a DNA sequence as set forth in the respective Sequence Listing.

One skilled in the art will appreciate that hybridization probes and PCR primers are not required to exactly match the target gene sequence to which they anneal. Therefore, in another embodiment, the oligonucleotides can comprise a sequence of at least 15 nucleotides and preferably at least 20 nucleotides, the oligonucleotide sequence being substantially similar to a respective DNA sequence set forth in the respective Sequence Listing. Preferably, such oligonucleotides will share at least about 75%–90% sequence identity with a respective DNA sequence set forth in the respective Sequence Listing and more preferably the shared sequence identity will be greater than 90%.

B. Example—Cloning of the Full-Length ORF Corresponding to Clone HinP #2-92

Using the techniques described below, the full-length gene corresponding to the clone HinP #2-92 was obtained. This gene, herein termed mtb2-92, includes an open-reading frame of 1089 bp (identified based on the G+C content relating to codon position). The alternative ‘GTG’ start codon was used, and this was preceded (8 base pairs upstream) by a Shine-Dalgarno motif. The gene mtb2-92 encodes a protein (termed MTB2-92) containing 363 amino acid residues with a predicted molecular weight of 40,436 Da.

Sequence homology comparisons of the predicted amino acid sequence of MTB2-92 with known proteins in the database indicated similarity to the cytochrome c oxidase subunit II of many different organisms. Cytochrome c oxidase is part of the electron transport chain, in which the subunits I and II form the functional core of the enzyme complex.

1. Cloning the Full-Length Gene Corresponding to HinP #2-92

The plasmid pHin2-92 was restricted with either BamH1 or EcoRI and then subcloned into the vector M13. The inserted DNA fragments were sequenced under the direction of M13 universal sequencing primers, Yanisch-Perron et al., *Gene* 33:103–119, 1985, using the AmpliCycle™ thermal sequencing kit (Perkin Elmer, Applied Biosystems Division, 850 Lincoln Centre Drive, Foster City, Calif. 94404, U.S.A.). The 5'-partial MTB2-92 DNA sequence was aligned using a GeneWorks™ (Intelligenetics, Mountain View, Calif., U.S.A.) program. Based on the sequence data obtained, two oligomers were synthesized. These oligonucleotides (5' CCCAGCTTGTGATACAGGAGG 3' (SEQ ID NO: 106) and 5' GGCCTCAGCGCGGCTCCGGAGG 3' (SEQ ID NO: 107)) represented sequences upstream and downstream, over an 0.8-kb distance, of the sequence encoding the partial MTB2-92 protein in the alkaline phosphatase fusion.

A *Mycobacterium tuberculosis* genomic cosmid DNA library was screened using PCR, Sambrook et al. (ed.), *Molecular Cloning: A Laboratory Manual,* 2nd ed., vol. 1–3, ed. Cold Spring Harbor Laboratory Press, Cold Spring Harbor, N.Y., 1989, in order to obtain the full-length gene encoding the MTB2-92 protein. Two hundred and ninety-four bacterial colonies containing the cosmid library were pooled into 10 groups in 100-$\mu$L aliqots of distilled water and boiled for 5 min. The samples were spun in a microfuge at maximal speed for 5 min. The supernatants were decanted and stored on ice prior to PCR analysis. The 100-$\mu$L PCR reaction contained: 10 $\mu$L supernatant containing cosmid DNA, 10 $\mu$L of 10×PCR buffer, 250 $\mu$M dNTPs, 300 nM downstream and upstream primers, and 1 unit Taq DNA polymerase.

The reactions were heated at 95° C. for 2 min, and 40 cycles of DNA synthesis were performed (95° C. for 30 s, 65° C. for 1 min, 72° C. for 2 min). The PCR products were loaded into a 1% agarose gel in TAE buffer, Sambrook et al. (ed.), *Molecular Cloning: A Laboratory Manual,* 2nd ed., vol. 1–3, Cold Spring Harbor Laboratory Press, Cold Spring Harbor, N.Y., 1989, for analysis.

The supernatant, which produced 800-bp PCR products, was then further divided into 10 samples and the PCR reactions were performed again. The colony that resulted in the correctly sized PCR product was then picked. The cosmid DNA from the positive clone (pG3) was prepared using the Wizard™ Mini-Prep Kit (Promega Corp, Madison, Wis., U.S.A.). The cosmid DNA was further sequenced using specific oligonucleotide primers. The deduced amino acid sequence encoded by the MTB2-92 protein is shown in FIG. 1.

2. Expression of the Full-Length Gene

To conveniently purify the recombinant protein, a histidine-tag coding sequence was engineered immediately upstream of the start codon of mtb2-92 using PCR. Two unique restriction enzyme sites for XbaI and HindIII were added to both ends of the PCR product for convenient subcloning. Two oligomers were used to direct the PCR reaction: (5' TCTAGACACCACCACCACCACCACGTGACACCT CGCGGGCCAGGTC 3' (SEQ ID NO: 108) and 5' AAGCTTCGCCATGC CGCCGGTAAGCGCC 3' (SEQ ID NO: 109)).

The 100-$\mu$L PCR reaction contained: 1 $\mu$g pG3 template DNA, 250 nM dNTP's, 300 nM of each primer, 10 $\mu$L of 10×PCR buffer, and 1 unit Taq DNA polymerase. The PCR DNA synthesis cycle was performed as described above.

The 1.4-kb PCR products were purified and ligated into the cloning vector pGEM-T (Promega). Inserts were removed by digestion using both Xba I and HindIII and the 1.4-kb fragment was directionally subcloned into the Xba I and Hind III sites of pMAL-c2 vector (New England BioLabs Ltd., 3397 American Drive, Unit 12, Mississauga, Ontario, L4V 1T8, Canada). The gene encoding MTB2-92 was fused, in frame, downstream of the maltose binding protein (MBP). This expression vector was named pMAL-MTB2-92.

3. Purification of the Encoded Protein

The plasmid pMAL-MTB2-92 was transformed into competent *E. coli* JM109 cells and a 1-litre culture was grown up in LB broth at 37° C. to an OD$_{550}$ of 0.5 to 0.6. The expression of the gene was induced by the addition of IPTG (0.5 mM) to the culture medium, after which the culture was grown for another 3 hours at 37° C. with vigorous shaking. Cultures were spun in the centrifuge at 10,000×g for 30 min and the cell pellet was harvested. The cell pellet was re-suspended in 50 mL of 20 mM Tris-HCl, pH 7.2, 200 mM NaCl, 1 mM EDTA supplemented with 10 mM β-mercaptoethanol and stored at −20° C.

The frozen bacterial suspension was thawed in cold water (0° C.), placed in an ice bath, and sonicated. The resulting cell lysate was then centrifuged at 10,000×g and 4° C. for 30 min, the supernatant retained, diluted with 5 volumes of buffer A (20 mM Tris-HCl, pH 7.2, 200 mM NaCl, and 1 mM EDTA) and applied to an amylose-resin column (New England Bio-Labs Ltd., 3397 American Drive, Unit 12, Mississauga, Ontario, L4V 1T8, Canada) that had been pre-equilibrated with buffer A. The column was then washed with buffer A until the eluate reached an A$_{280}$ of 0.001, at which point the bound MBP-MTB2-92 fusion protein was eluted with buffer A containing 10 mM maltose. The protein purified by the amylose-resin affinity column was about 84 kDa which corresponded to the expected size of the fusion protein (MBP: 42 kDa, MTB2-92 plus the histidine tag: 42 kDa).

The eluted MBP-MTB2-92 fusion protein was then cleaved with factor Xa to remove the MBP from the MTB2-92 protein. One mL of fusion protein (1 mg/mL) was mixed with 100 μL of Factor Xa (200 μg/mL) and kept at room temperature overnight. The mixture was diluted with 10 mL of buffer B (5 mM imidazole, 0.5 M NaCl, 20 mM Tris-HCl, pH 7.9, 6 M urea) and urea was added to the sample to a final concentration of 6 M urea. The sample was loaded onto the Ni-NTA column (QIAGEN, 9600 De Soto Ave., Chatsworth, Calif. 91311, U.S.A.) pre-equilibrated with buffer B. The column was washed with 10 volumes of buffer B and 6 volumes of buffer C (60 mM imidazole, 0.5 M NaCl, 20 mM Tris-HCl, pH 7.9, 6 M urea). The bound protein was eluted with 6 volumes of buffer D (1 M imidazole, 0.5 M NaCl, 20 mM Tris-HCl, pH 7.9, 6 M urea).

At each stage of the protein purification, a sample was analyzed by SDS polyacylamide gel electrophoresis, Laemmli, *Nature* (London) 227:680–685, 1970.

C. Correction of Sequence Errors

Some of the sequences presented in the Sequence Listing may contain sequence ambiguities. Sequence ambiguities occur when the results from the sequencing reaction do not clearly distinguish between the individual base pairs. Therefore, substitute abbreviations denoting multiple base pairs are provided in Table 3, supra. These abbreviations denote which of the four bases could possibly be at a position that was found not to give a clear experimental result. Naturally, in order to ensure that the immunostimulatory function is maintained, one would utilize a sequence without such ambiguities. For those sequences containing ambiguities, one would therefore utilize the sequence data provided in the Sequence Listing to design primers corresponding to each terminal of the provided sequence and, using these primers in conjunction with the polymerase chain reaction, synthesize the desired DNA molecule using *M. tuberculosis* genomic DNA as a template. Standard PCR methodologies, such as those described above, may be used to accomplish this.

D. Additional Examples of Cloning of Full-Length Mtb-PhoA Fusion Proteins

Selected mtb-phoA fusions were sequenced using the Taq-Track™ sequencing system (Promega Corp.), and sequencing was directed from a primer located 48 bp upstream of the junction between the *M. tuberculosis* and phoA DNA. Sequences were compared to the databases of the *M. tuberculosis* genome projects, Cole et al., *Nature* 393:537–544, 1998, and the National Centre of Biotechnology Information at the National Library of Medicine (Bethesda, Md.) using the "BLASTX", "BLASTN", and "TBLAST" programs, Atschul et al., *Nucleic Acids* 25:3389–3402, 1997. A determination of signal peptide determination was made using the SignalP neural network trained on Gram-positive data, Neilson et al., *Protein Eng.* 10:1–6, 1997.

Whenever the upstream DNA sequence matched the raw sequence from the database of the *M. tuberculosis* genome projects, the extent of the reading frame and direction of translation were ascertained using a G+C analysis package, Bibb et al., *Gene* 30:157–166, 1984. A verification was made of whether the mtb-phoA fusion was in the same reading frame as the predicted ORF. In some cases, the extent of the ORF had already been assigned, and the assessment of the genome project was used for the fusion construction.

PCR was used to amplify the complete predicted ORFs encoding the proteins identified in the immunogenicity study. Oligodeoxynucleotide primers were designed with restriction sites in order to clone the amplified fragments into expression vectors. Table 5 provides a description the primer sequences used. All PCR reactions were conducted in 20 μL using a 6:1 Taq polymerase: Pfu polymerase enzyme combination. The reaction mixes contained either 1 μL DMSO or 4 μL of Q solution (proprietary solution available from Qiagen, Dusseldorf, Germany, for denaturation in PCR) as a denaturant. A manual hot start was used for all PCR reactions which consisted of an initial denaturization (95° C., 4 min.) followed by a final extension (72° C., 4 min.). Standard protocols were followed for cloning, Sambrook et al. (ed.), *Molecular Cloning: A Laboratory Manual*, 2nd ed., vol. 1–3, Cold Spring Harbor Laboratory Press, Cold Spring Harbor, N.Y., 1989, and expression of the *Mycobacterium tuberculosis* proteins as fusions in commercial expression vectors. The different expression vectors used included pMAL-c2 (New England Biolabs, Beverly, Mass.), pGEX-4T3 (Pharmacia, Piscataway, N.J.), and pET-17xb (Novagen, Madison, Wis.). Respectively, these expression vectors enabled the N-terminal fusion of the maltose binding protein (MBP), glutathione S-transferase (GST) or the 260 amino acid T7 gene 10 product (PET) containing the T7.Tag® (Novagen, Madison, Wis.) to the products of the cloned DNA.

TABLE 5

Oligonucleotide Primers Used for PCR Amplification

| Clone | Primer | Sequence 5' to 3' | SEQ ID NO: |
|---|---|---|---|
| GST-152 | 1-152F | GTCAAGGATCCGGCATGGACCCGCTGAACCGCCGAC | 142 |
|  | 1-152R | ATGTCGGGATCCAAGCTTTCGACGGTCGGCGCGTCGGCGCCGGG | 143 |

TABLE 5-continued

Oligonucleotide Primers Used for PCR Amplification

| Clone | Primer | Sequence 5' to 3' | SEQ ID NO: |
|---|---|---|---|
| MBP- 264 | 1-264F | GCAGATGCATCTAATGGGATCCGCGGAGTATATCTCC | 144 |
| | 1-264R | GGCGCCGTGGGTGTCAGCGAAGCTTACCTGGTTGTTG | 145 |
| PET- 23 | 2-23F | GGTGCCGAATTCGCGCCGATGCTGGACGCGG | 146 |
| | 2-23R | ACCCGAATTCCCAAGCTTGCTGCTCAAACCACTGTTCC | 147 |
| MBP- 506 | 2-506F | GCGCCCAAGGGATCCCCGGCTACCATGCCTTCG | 148 |
| | 2-506R | CTCGAAGGGATCCGCGTTCGTTTGGCCGCCCGC | 149 |
| GST- 511 | 2-511F | GGCAGTGGGATCCGTAGCGGTGCGGCGTAAGGTGCGG | 150 |
| | 2-511R | GACTTCGTGGATCCGGTCAAGACAAGCTTTGCGGTGATCAAGGCGGC | 151 |
| PET- 639 | 2-639F | CATGAATGAATTCATCTCACAAGCGTGCGGCTCCCACCGACCC | 152 |
| | 2-639R | CCTTGGCGAATTCTCAAAGGAAAGCTTCGAAGGCGG | 153 |
| GST- 822 | 2-822F | GGAGTTCGGATCCATCGCCATGCAACTCTCCTCCCGG | 154 |
| | 2-822R | GGGCAGTGGATCCGTGGTCAGCAAGCTTTCCCTAGAGTTTCGTGCG | 155 |
| MBP- 825 | 2-825F | GTGGCGCCGAATTCAAGCGCGGTGTCGCAACGCTG | 156 |
| | 2-825R | CGCTTAAGCGCGAAGCTTCGTCGAGCCGCG | 157 |
| PET- 916 | 2-916F | GACCGGAATTCATGATCCAGATCGCGCGCACCTGGCGG | 158 |
| | 2-916R | AACATGAATTCAAGCTTCGAGGCCGCCGACGAATCCGCTCACCG | 159 |
| PET- 1084 | 2-1084F | CGGGTCGCCGAATTCACGCGGAGCCGGGATTGCGC | 160 |
| | 2-1084R | GGCGGAATTCAAGCTTCGGTTCATCCGCCGCCCCATGC | 161 |
| GST- 206 | 3-206F | CCCCGGGGATCCGGGGTGCTGGGATGACGG | 162 |
| | 3-206R | ACGACGGATCCTAAGCTTGCAGGCGCGCCGATACGCGGC | 163 |
| GST- 827 | 2-827F | TCTCCGGGGATCCCAGATGAATGTCGTCGACATTTC | 164 |
| | 2-827R | GGGTCTCCGGATCCCCCATACCGACATG | 165 |
| GST- 247 | 1-247F | CCGACTCGAGCGGCGGCGCACACACAACGGTC | 166 |
| | 1-247R | AATCCTCGAGCCCTGCGGTCGCCTTCCGAGCG | 167 |
| PET- 47 | 3-47F | ATCCGGCCCGAATTCGCTGACCGTGGCCAGCGACGA | 168 |
| | 3-47R | GATCGGGAGAATTCCGCCGACTTAAGCTTCAGCTGAGCTGG | 169 |

The different expression vectors used included pMAL-c2 (New England Biolabs), pGEX-4T3 (Pharmacia, Piscataway, N.J.), and pET-17xb (Novagen, Madison, Wis.). These expression vectors enabled the N-terminal fusion of the maltose binding protein (MBP), glutathione S-transferase (GST), or the 260 amino acid T7 gene 10 product (PET) containing the T7.Tag® (Novagen, Madison, Wis.) to be added to the products of the cloned DNA. Table 6 provides a summary of the results from cloning the PCR products into the various vectors described above.

TABLE 6

Recombinant Plasmids for Cloning and Expression of the Full-length Proteins

| Plasmid Construct | Expression Vector | Cloning Sites | Sanger ID | Fusion Product | Predicted Mr (kDa) |
|---|---|---|---|---|---|
| pAM23E | pET-17xb | E | MTCY13E10.15c | PET-23 | 124 |
| pAM47E | pET-17xb | E | MTCY50.02 | PET-47 | 94 |
| pAM152E | pGEX-4T3 | B | MTCY16B7.09 | GST-152 | 70 |
| pAM206E | pGEX-4T3 | B | MTCY270.17 | GST-206 | 60 |
| pAM247E | pGEX-4T3 | E | MTCI364.18 | GST-247 | 78 |
| pAM264E | pMAL-c2 | B, H | MTCY78.03c | MBP-264 | 68 |
| pAM506E | pMAL-c2 | B | MTCY253.27c | MBP-506 | 105 |
| pAM511E | pGEX-4T3 | B | MTCY50.08c | GST-511 | 46 |
| pAM639E | pET-17xb | E | MTCY02B12.02 | PET-639 | 56 |
| pAM822E | pGEX-4T3 | B | MTV004.48 | GST-822 | 50 |
| pAM825E | pMAL-c2 | E, H | MTCY31.03c | MBP-825 | 60 |
| pAM827E | pGEX-4T3 | B | MTCY01B2.15c | GST-827 | 80 |
| pAM916E | pET-17xb | E | MTCY21D4.03c | PET-916 | 61 |
| pAM1084E | pET-17xb | E | MTV023.03c | PET-1084 | 76 |

Abbreviations: E: EcoRI; B: BamHI; H: HindIII; X: XhoI; c: complementary direction SDS-PAGE and Western Blotting were used to identify the novel antigens expressed by the clones. Sodium dodecyl sulphate polyacrylamide gel electrophoresis (SDS-PAGE) was carried out using 10% slab gels in a continuous buffer system, Laemmli, *Nature* (London) 227:680–685, 1970. Proteins were electrophoretically transferred from the gel to a nitrocellulose membrane using standard protocols, Sambrook et al. (ed.), *Molecular Cloning: A Laboratory Manual*, 2nd ed., vol. 1–3, Cold Spring Harbor Laboratory Press, Cold Spring Harbor, N.Y., 1989. Western blots for the GST (Pharmacia), T7 gene 10 (Invitrogen), and MBP (NEB) tagged fusion proteins were conducted as per the suppliers' instructions. The chemiluminescent Renaissance™ system (DuPont NEN Renaissance, NEL-201) was used to image bound antibody.

Subsequently, the following nucleic acid sequences were over-expressed in *E. coli* BL21 plysS to produce fusion proteins: MBP-264 (SEQ ID NO: 114), PET-23 (SEQ ID NO: 117), MBP-506 (SEQ ID NO: 115), MPB-825 (SEQ ID NO: 116), PET-639 (SEQ ID NO: 119), PET-916 (SEQ ID NO: 120), PET-1084 (SEQ ID NO: 121), PET-47 (SEQ ID NO: 118); in *E. coli* BL21: GST-152 (SEQ ID NO: 122), GST-822 (SEQ ID NO: 124); and in *E. coli* SURE: GST-206 (SEQ ID NO: 125). The recombinant fusion proteins MBP-506 (SEQ ID NO: 115), MBP-825 (SEQ ID NO: 116), GST-152 (SEQ ID NO: 122), GST-822 (SEQ ID NO: 124) GST-827 (SEQ ID NO: 126), PET-639 (SEQ ID NO: 119), PET-1084 (SEQ ID NO: 121) formed inclusion bodies that were harvested from the pellet following centrifugation of the bacterial sonicate. The fusion proteins PET-916 and GST-206 were found primarily in the supernatant and underwent considerable breakdown in culture. Protein fractions were checked by SDS-PAGE using Coomassie Blue staining and approximate concentrations were determined by Western blotting.

An additional fusion protein, GST-247 (SEQ ID NO: 141), was constructed using a different cloning strategy. The PCR product resulting from a reaction using the primers described in Table 5 and the entire MTCI364.18 cds was digested with EcoR1. The resulting fragment was then cloned into pGEX-4T3, with the C-terminus adjacent to the GST sequence. The resulting protein fragment included amino acid 43 to amino acid 514 of the 597 amino acid protein predicted by the genome project.

The amino acid sequences encoded by nucleic acid sequences described above are also shown in the sequence listing. These amino acid sequences are SEQ ID NOS: 128–141, which correspond to the nucleic acid sequences shown in SEQ ID NOS: 114–127, respectively.

VI. EXPRESSION AND PURIFICATION OF THE CLONED PEPTIDES

The DNA sequences disclosed herein that encode *Mycobacterium tuberculosis* peptides having an immunostimulatory activity, as well as the corresponding full-length *Mycobacterium tuberculosis* genes, enable one of ordinary skill in the art to express and purify the peptides encoded by these sequences. Methods for expressing proteins by recombinant means in compatible prokaryotic or eukaryotic host cells are well known in the art and are discussed, for example, in Sambrook et al. (ed.), *Molecular Cloning: A Laboratory Manual,* 2nd ed., vol. 1–3, Cold Spring Harbor Laboratory Press, Cold Spring Harbor, N.Y., 1989, and Ausubel et al. (ed.), *Current Protocols in Molecular Biology*, Greene Publishing and Wiley-Interscience, New York (with periodic updates), 1987. Peptides expressed by the nucleotide sequences disclosed herein are useful for preparing vaccines effective against *M. tuberculosis* infection, for use in diagnostic assays, and for raising antibodies that specifically recognize *M. tuberculosis* proteins. One method of purifying the peptides is that presented in part V(B) above.

The most commonly used prokaryotic host cells for expressing prokaryotic peptides are strains of *Escherichia coli*, although other prokaryotes, such as *Bacillus subtilis*, Streptomyces, or Pseudomonas may also be used, as is well known in the art. Partial or full-length DNA sequences, encoding an immunostimulatory peptide according to the present invention, may be ligated into bacterial expression vectors. One aspect of the present invention is thus a recombinant DNA vector including a nucleic acid molecule provided by the present invention. Another aspect is a transformed cell containing such a vector.

Methods for expressing large amounts of protein from a cloned gene introduced into *Escherichia coli* (*E. coli*) may be utilized for the purification of the *Mycobacterium tuberculosis* peptides. Methods and plasmid vectors for producing fusion proteins and intact native proteins in bacteria are described in Sambrook et al. (ed.), *Molecular Cloning: A Laboratory Manual,* 2nd ed., vol. 1–3, Cold Spring Harbor Laboratory Press, Cold Spring Harbor, N.Y., 1989. Such fusion proteins may be made in large amounts, are relatively simple to purify, and can be used to produce antibodies. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy.

Often, proteins expressed at high levels are found in insoluble inclusion bodies. Methods for extracting proteins from these aggregates are described in Sambrook et al. (ed.), *Molecular Cloning: A Laboratory Manual,* 2nd ed., vol. 1–3, Cold Spring Harbor Laboratory Press, Cold Spring Harbor, N.Y., 1989. Vector systems suitable for the expression of lacZ fusion genes include the pUR series of vectors, Ruther et al., *EMBO J.* 2:1791, 1983; pEX1-3, Stanley and Luzio, *EMBO J.* 3:1429, 1984; and pMR100, Gray et al., *Proc. Natl. Acad Sci. USA* 79:6598, 1982. Vectors suitable for the production of intact native proteins include pKC30, Shimatake and Rosenberg, *Nature* 292:128, 1981; pKK177-3, Amann and Brosius, *Gene* 40:183, 1985; and pET-3, Studiar and Moffatt, *J. Mol. Biol.* 189:113, 1986. Fusion proteins may be isolated from protein gels, lyophilized, ground into a powder, and used as antigen preparations.

Mammalian or other eukaryotic host cells, such as those of yeast, filamentous fungi, plant, insect, amphibian, or avian species, may also be used for protein expression, as is well known in the art. Examples of commonly used mammalian host cell lines are VERO and HeLa cells, Chinese hamster ovary (CHO) cells, and WI38, BHK, and COS cell lines, although it will be appreciated by the skilled practitioner that other prokaryotic and eukaryotic cells and cell lines may be appropriate for a variety of purposes, e.g., to provide higher expression, desirable glycosylation patterns, or other features.

Additionally, peptides, particularly shorter peptides, may be chemically synthesized, avoiding the need for purification from cells or culture media. It is known that peptides as short as 5 amino acids can act as an antigenic determinant for stimulating an immune response. Such peptides may be administered as vaccines in ISCOMs (Immune Stimulatory Complexes) as described by Janeway & Travers, *Immunobiology: The Immune System In Health and Disease* 13.21, Garland Publishing, Inc., New York, 1997. Accordingly, one aspect of the present invention includes small peptides encoded by the nucleic acid molecules disclosed herein. Such peptides include at least 5, and preferably 10 or more, contiguous amino acids of the peptides encoded by the disclosed nucleic acid molecules.

VII. SEQUENCE VARIANTS

It will be apparent to one skilled in the art that the immunostimulatory activity of the peptides encoded by the DNA sequences disclosed herein lies not in the precise nucleotide sequence of the DNA sequences, but rather in the epitopes inherent in the amino acid sequences encoded by the DNA sequences. It will therefore also be apparent that it is possible to recreate the immunostimulatory activity of one of these peptides by recreating the epitope without necessarily recreating the exact DNA sequence. This can be achieved either by directly synthesizing the peptide (thereby circumventing the need to use the DNA sequences) or, alternatively, by designing a nucleic acid sequence that encodes the epitope, but which differs, by reason of the redundancy of the genetic code, from the sequences disclosed herein.

Accordingly, the degeneracy of the genetic code further widens the scope of the present invention as it enables major variations in the nucleotide sequence of a DNA molecule while maintaining the amino acid sequence of the encoded protein. The genetic code and variations in nucleotide codons for particular amino acids are presented in Tables 7 and 8, respectively. Based upon the degeneracy of the genetic code, variant DNA molecules may be derived from the DNA sequences disclosed herein using standard DNA mutagenesis techniques, or by synthesis of DNA sequences.

TABLE 7

The Genetic Code

| First Pos'n | Second Pos'n | | | | Third Pos'n |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ochre termination triplet, and "Stop (amb)" for the amber. ATG is the most common initiator codon; GTG usually codes for valine, but it can also code for methionine to initiate an mRNA chain.

TABLE 8

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

Additionally, standard mutagenesis techniques may be used to produce peptides that vary in amino acid sequence from the peptides encoded by the DNA molecules disclosed herein. However, such peptides will retain the essential characteristic of the peptides encoded by the DNA molecules disclosed herein, i.e., the ability to stimulate INF-γ production. This characteristic can be readily determined by the assay technique described above. Such variant peptides include those with variations in amino acid sequence including minor deletions, additions, and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

In order to maintain the functional epitope, preferred peptide variants will differ by only a small number of amino acids from the peptides encoded by the DNA sequences disclosed herein. Preferably, such variants will be amino acid substitutions of single residues. Substitutional variants are those in which at least one residue in the amino acid sequence has been removed and a different residue inserted in its place. Such substitutions generally are made in accordance with the following Table 9 when it is desired to finely modulate the characteristics of the protein. Table 9 shows amino acids that may be substituted for an original amino acid in a protein and that are regarded as conservative substitutions. As noted, all such peptide variants are tested to confirm that they retain the ability to stimulate INF-γ production.

TABLE 9

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in immunological identity are made by selecting substitutions that are less conservative than those in Table 9, i.e., selecting residues that differ more significantly in their effect on maintaining: (a) the structure of the polypeptide backbone in the area of the substitution, for example, as a sheet or helical conformation, (b) the charge or hydrophobicity of the molecule at the target site, or (c) the bulk of the side chain. The substitutions that, in general, are expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. However, such variants must retain the ability to stimulate INF-γ production.

VIII. USE OF CLONED MYCOBACTERIUM SEQUENCES TO PRODUCE VACCINES

A. Overview

The purified peptides encoded by the nucleotide sequences of the present invention may be used directly as immunogens for vaccination. The conventional tuberculosis vaccine is the BCG (Bacillus Calmette-Guerin) vaccine, which is a live vaccine comprising attenuated *Mycobacterium bovis* bacteria. However, the use of this vaccine in a number of countries, including the U.S., has been limited because administration of the vaccine interferes with the use of the tuberculin skin test to detect infected individuals, Wyngaarden et al. (eds.), *Cecil Textbook of Medicine, 19th ed.*, W. B. Saunders, Philadelphia, Pa., pages 1733–1742, 1992, and section VIII (2) below.

The present invention provides a possible solution to the problems inherent in the use of the BCG vaccine in conjunction with the tuberculin skin test. The solution is based upon the use of one or more of the immunostimulatory *M. tuberculosis* peptides disclosed herein as a vaccine and one or more different immunostimulatory *M. tuberculosis* peptides disclosed herein in the tuberculosis skin test (see section IX (2) below). If the immune system is primed with such a vaccine, the system will be able to resist an infection by *M. tuberculosis*. However, exposure to the vaccine peptides alone will not induce an immune response to those peptides that are reserved for use in the tuberculin skin test. Thus, the present invention would allow the clinician to distinguish between a vaccinated individual and an infected individual.

Methods for using purified peptides as vaccines are well known in the art and are described in the following publications: Pal et al., *Infect. Immun.* 60:4781–4792, 1992 (describing immunization with extra-cellular proteins of *Mycobacterium tuberculosis*); Yang et al., *Immunology* 72:3–9, 1991 (vaccination with synthetic peptides corresponding to the amino acid sequence of a surface glycoprotein from Leishmania major); Andersen, *Infection & Immunity* 62:2536, 1994 (vaccination using short-term culture filtrate containing proteins secreted by *Mycobacterium tuberculosis*); and Jardim et al., *J. Exp. Med.* 172:645–648, 1990 (vaccination with synthetic T-cell epitopes derived from Leishmania parasite). Methods for preparing vaccines that contain immunogenic peptide sequences are also disclosed in U.S. Pat. Nos. 4,608,251, 4,601,903, 4,599,231, 4,5995230, 4,596,792 and 4,578,770. The formulation of peptide-based vaccines employing *M. tuberculosis* peptides is also discussed extensively in International Patent Application No. WO 95/01441.

As is well known in the art, adjuvants such as Complete Freund's Adjuvant (CFA) and Incomplete Freund's Adjuvant (IFA) may be used in formulations of purified peptides as vaccines. Accordingly, one embodiment of the present invention is a vaccine comprising one or more immunostimulatory *M. tuberculosis* peptides encoded by genes including a sequence shown in the attached sequence listing, together with a pharmaceutically acceptable adjuvant.

Additionally, the vaccines may be formulated using a peptide according to the present invention together with a pharmaceutically acceptable excipient such as water, saline, dextrose, or glycerol. The vaccines may also include auxiliary substances such as emulsifying agents and pH buffers.

It will be appreciated by one of ordinary skill in the art that vaccines formulated as described above may be administered in a number of ways including subcutaneously, intramuscularly, and by intra-venous injection. Doses of the vaccine administered will vary depending on the antigenicity of the particular peptide or peptide combination employed in the vaccine, and characteristics of the animal or human patient to be vaccinated. While the determination of individual doses will be within the skill of the administering physician, it is anticipated that doses of between 1 microgram and 1 milligram will be employed.

As with many vaccines, the vaccines of the present invention may routinely be administered several times over the course of a number of weeks to ensure that an effective immune response is triggered. As described in International Patent Application No. WO 95/01441, up to six doses of the vaccine may be administered over a course of several weeks, but more typically between one and four doses are administered. Where such multiple doses are administered, they will normally be administered at from two to twelve-week intervals, more usually from three to five-week intervals. Periodic boosters at intervals of 1–5 years, usually three years, will be desirable to maintain the desired levels of protective immunity.

As described in WO 95/01441, the course of the immunization may be followed by in vitro proliferation assays of PBL (peripheral blood lymphocytes) co-cultured with ESAT6 or ST-CF, and especially by measuring the levels of IFN-released from the primed lymphocytes. The assays are well known and are widely described in the literature, including in U.S. Pat. Nos. 3,791,932; 4,174,384 and 3,949,064.

To ensure an effective immune response against tuberculosis infection, vaccines according to the present invention may be formulated with more than one immunostimulatory peptide encoded by the nucleotide sequences disclosed herein. In such cases, the amount of each purified peptide incorporated into the vaccine will be adjusted accordingly.

Alternatively, multiple immunostimulatory peptides may also be administered by expressing the nucleic acids encoding the peptides in a nonpathogenic microorganism, and using the transformed nonpathogenic microorganism as a vaccine. As described in International Patent Application No. WO 95/01441*, Mycobacterium bovis* BCG may be employed for this purpose although this approach would destroy the advantage outlined above to be gained from using separate classes of the peptides as vaccines and in the skin test. As disclosed in WO 95/01441, an immunostimulatory peptide of *M. tuberculosis* can be expressed in the BCG bacterium by transforming the BCG bacterium with a nucleotide sequence encoding the *M. tuberculosis* peptide. Thereafter, the BCG bacteria can be administered in the same manner as a conventional BCG vaccine. In particular embodiments, multiple copies of the *M. tuberculosis* sequence are transformed into the BCG bacteria to enhance the amount of *M. tuberculosis* peptide produced in the vaccine strain.

Finally, a recent development in the field of vaccines is the direct injection of nucleic acid molecules encoding peptide antigens, as described in Janeway & Travers, *Immunobiology: The Immune System In Health and Disease*, page 13.25, Garland Publishing, Inc., New York, 1997; and McDonnell & Askari, *N. Engl. J. Med* 334:42–45, 1996. Thus, plasmids that include nucleic acid molecules described herein, or that include nucleic acid sequences encoding peptides according to the present invention, may be utilized in such DNA vaccination methods.

B. Pool of 12 *M. tuberculosis* Proteins Confers Immunity

A guinea pig protection study was undertaken to compare three candidate vaccine preparations with BCG. These included the Antigen 85 complex with IL-2 (Ag 85), a fusion-protein pool of twelve *M. tuberculosis* proteins in combination with IL-2 (FPP), and a control containing the adjuvant monophosphoryl lipid A (MPL).

1. Materials and Methods

The following nucleic acid sequences were identified and cloned into expression vectors as described supra and then were over-expressed in *E. coli* BL21 (DE3) plysS (Novagen, Madison, Wis.) to produce fusion proteins: MBP-264 (SEQ ID NO: 114), MBP-506 (SEQ ID NO: 115), MBP-825 (SEQ ID NO: 116), PET-23 (SEQ ID NO: 117), PET-47 (SEQ ID NO: 118), PET-639 (SEQ ID NO: 119), PET-916 (SEQ ID NO: 120), PET-1084 (SEQ ID NO: 121); in *E. coli* BL21: GST-152 (SEQ ID NO: 122), GST-511 (SEQ ID NO: 123), GST-822 (SEQ ID NO: 124); and in *E. coli* SURE (Stratagene, La Jolla, Calif.): GST-206 (SEQ ID NO: 125).

The Antigen 85 complex was kindly provided by Dr. John Belisle (Colorado State University, Fort Collins, Colo.) through the TB research materials and vaccine testing contract (NIH, NIAID NOI AI-75320)(Belisle *Science* 276:1420–1422, 1997).

Animals. Outbred female Hartley guinea pigs, that were specifically pathogen-free (Charles River Laboratories, North Willmington, Mass.) were held under barrier conditions in an ANL-3 biohazard laboratory. Owing to expense, experimental groups were limited to between three and five animals. They were housed one to a cage and given free access to water and guinea pig chow. Following aerogenic infection with M. tuberculosis H37Rv, the guinea pigs were monitored over a period of 27 weeks. After the first four weeks, the animals were weighed weekly, with the exception of a two-week period, and any animals demonstrating sudden significant weight loss were euthanised.

Bacterial infection. Guinea pigs were aerogenically infected with between 20 and 50 bacilli of M. tuberculosis H37Rv using a calibrated aerosol generation device (Glas-Col, Terre Haute, Ind.) that delivered the inoculum to each lung.

Vaccinations. Guinea pigs were immunized subcutaneously two times at a three-week interval using 100 μg of AG85 complex with 20 μg Proleukin-PEG IL-2 (Chiron, Emeryville, Calif.) and emulsified in 100 μg Monophosphoryl Lipid A (MPL; Ribi ImmunoChem Research, Inc., Hamilton, Mont.) adjuvant that had been solubilized in 0.02% triethanolamine and 0.4% dextrose by sonication (MPL-TeoA); and 100 μg of fusion proteins that had been pooled in equivalent concentrations with 20 μg PEG IL-2 (Chiron) in 100 μg MPL-TeoA adjuvant. The positive control, BCG Copenhagen, was injected once intradermally ($10^3$ bacilli/guinea pig), corresponding to the second set of injections.

Necropsy. Guinea pigs were euthanized by the intraperitoneal injection of 1–3 mL of sodium pentobarbital (Sleepaway, Ft. Dodge, Iowa). The abdominal and thoracic cavities were opened aseptically and the spleen and right lower lung lobe were homogenised separately in sterile Teflon-glass homogenisers in 4.5 mL of sterile physiological saline. The number of viable M. tuberculosis organisms was determined by inoculating appropriate dilutions onto Middlebrook™ 7H10 agar plates (Hardy Diagnostics, Santa Maria, Calif.). The colonies were counted after three weeks' incubation at 37° C. Data were expressed as mean logo number of viable organisms per portion of tissue.

Histological analysis. Sagital tissue sections were made through the middle of the left lower lobe. The tissue sections were fixed in 10% neutral buffered formalin and stained with hematoxylin and eosin. Prepared tissues were coded prior to evaluation by a board-certified pathologist.

2. Results

Long-term survival assay. The survival of test groups after aerosol infection and their respective weight gain or loss are summarized in Table 10.

TABLE 10

Total Weight Change, Survival Length and Bacterial Loads in The Lung and Spleen For Individual Guinea Pigs within Different Vaccination Groups, After Aerogenic Infection with M. tuberculosis.

| Group | No | Survival (wks) | Wt. Change (g) | Bacterial Load $Log_{10}$ Lung | Bacterial Load $Log_{10}$ Spleen |
|---|---|---|---|---|---|
| BCG | 117 | 27 | 159 | 3.65 | 4.93 |
|  | 121 | 27 | 99 | 4.13 | 3.95 |
|  | 130 | 27 | 151 | 4.13 | 3.65 |
| mean |  | 27.0 ± 0.0136 | 136 ± 33 | 3.97 ± 0.16 | 4.18 ± 0.39 |
| Ag85 | 155 | 25 | −25 |  |  |
|  | 156 | 20 | −48 |  |  |
|  | 158 | 27 | 86 | 5.91 | 3.65 |
|  | 162 | 27 | 75 | 5.19 | 4.19 |
|  | 167 | 27 | 86 | 5.94 | 3.83 |
| mean |  | 25.2 ± 1.4 | 35 ± 66 | 5.68 ± 0.24 | 3.89 ± 0.16 |
| MPL | 170 | 27 | 81 | 5.31 | 4.95 |
|  | 171 | 12 | −205 | >7.0 | >7.0 |
|  | 172 | 9 | −231 | 6.51 | 6.49 |
| mean |  | 16.0 ± 5.6 | −118 ± 173 | 6.27 ± 0.87 | 6.15 ± 1.07 |
| FPP | 157 | 15 | 17 | 6.58 | 5.23 |
|  | 166 | 27 | 82 | 5.48 | 2.65 |
|  | 169 | 27 | 133 | 5.26 | 0.0* |
| mean |  | 23.0 ± 4.0 | 77 ± 58 | 5.77 ± 0.41 | 2.63 ± 1.51 |

*minimal number of detectable organisms = 225

All positive-control animals vaccinated with BCG exhibited consistent weight gain and were healthy when the experiment was curtailed after 27 weeks.

Three out of five guinea pigs immunized with Ag85 survived to 27 weeks, as did 2 out of 3 guinea pigs vaccinated with the fusion protein mixture. All of these surviving animals showed reasonable weight gain. In contrast, 2 of 3 negative controls exhibited precipitous weight loss and died within the first 17 weeks of the experiment. That animal experienced dramatic weight loss throughout the latter few weeks of the experiment.

Bacterial Loads. Table 9 shows the individual bacterial loads found in the lung and spleen. Subsequent assessment of bacterial loads indicated that only BCG dramatically reduced bacterial numbers in the lungs. Approximately one-half log reduction in counts were observed in mice administered Ag85 of the fusion protein mixture.

Dissemination of bacteria to the spleen was reduced in all groups relative to the negative control and the fusion protein pool effected the greatest control on dissemination.

Comparative Histology. Guinea pigs immunized with BCG exhibited a few discrete granulomas in the lungs with a diffuse interstitial mononuclear cell infiltrate affecting approximately 70% of the lung parenchyma, with no evidence of necrosis, caseation or mineralization. In contrast, guinea pigs in the negative control group had a moderate to severe, multi-focal granulomatous pneumonia with extensive caseation and necrosis throughout the lung parenchyma.

A mixed response was seen in guinea pigs administered Ag85. In two animals that died before 27 weeks (at 20 and 25 weeks, respectively) a moderate, multi-focal, necrosuppurative granulomatous pneumonia was seen, with scattered aggregates of lymphocytes and areas of mineralization and fibrosis. In the three surviving animals the pathology was less severe, with increased numbers of aggregations of lymphocytes being evident and the granulomatous pneumonia scored as mild to moderate. A similar histological appearance was seen in the lungs of two guinea pigs immunized with fusion proteins that were still alive at 27 weeks.

IX. USE OF CLONED MYCOBACTERIUM SEQUENCES IN DIAGNOSTIC ASSAYS

Another aspect of the present invention is a composition for diagnosing tuberculosis infection. The composition includes peptides encoded by one or more of the nucleotide sequences of the present invention. The invention also encompasses methods and compositions for detecting the presence of anti-tuberculosis antibodies, tuberculosis peptides, and tuberculosis nucleic acid sequences in body samples. Three examples typify the various techniques that may be used to diagnose tuberculosis infection using the present invention: an in vitro ELISA assay, an in vivo skin test assay, and a nucleic acid amplification assay.

A. In Vitro ELISA Assay

One aspect of the invention is an ELISA that detects anti-tuberculosis mycobacterial antibodies in a medical specimen. An immunostimulatory peptide encoded by a nucleotide sequence of the present invention is employed as an antigen and is preferably bound to a solid matrix such as a crosslinked dextran such as SEPHADEX® (Pharmacia, Piscataway, N.J.), agarose, polystyrene, or the wells of a microtiter plate. The polypeptide is admixed with the specimen, such as human sputum, and the admixture is incubated for a sufficient time to allow antimycobacterial antibodies present in the sample to immunoreact with the polypeptide. The presence of the immunopositive immunoreaction is then determined using ELISA.

In a preferred embodiment, the solid support to which the polypeptide is attached is the wall of a microtiter assay plate. After attachment of the polypeptide, any nonspecific binding sites on the microtiter well walls are blocked with a protein such as bovine serum albumin (BSA). Excess BSA is removed by rinsing and the medical specimen is admixed with the polypeptide in the microtiter wells. After a sufficient incubation time, the microtiter wells are rinsed to remove excess sample and then a solution of a second antibody, capable of detecting human antibodies, is added to the wells. This second antibody is typically linked to an enzyme such as peroxidase, alkaline phosphatase, or glucose oxidase. For example, the second antibody may be a peroxidase-labeled goat anti-human antibody. After further incubation, excess amounts of the second antibody are removed by rinsing and a solution containing a substrate for the enzyme label (such as hydrogen peroxide for the peroxidase enzyme) and a color-forming dye precursor, such as o-phenylenediamine, is added. The combination of mycobacterium peptide (bound to the wall of the well), the human anti-mycobacterial antibodies (from the specimen), the enzyme-conjugated anti-human antibody, and the color substrate produces a color than can be read using an instrument that determines optical density, such as a spectrophotometer. These readings can be compared to a control incubated with water in place of the human body sample, or, preferably, a human body sample known to be free of antimycobacterial antibodies. Positive readings indicate the presence of anti-mycobacterial antibodies in the specimen, which in turn indicate a prior exposure of the patient to tuberculosis.

B. Example of ELISA Using Eight Full-Length Clones

The following nucleic acid sequences were overexpressed in E. coli BL21 plysS to produce fusion proteins: MBP-506 (SEQ ID NO: 115), MPB-825 (SEQ ID NO: 116), PET-639 (SEQ ID NO: 119), PET-916 (SEQ ID NO: 120), PET-1084 (SEQ ID NO: 121); in E. coli BL21: GST-152 (SEQ ID NO: 122), GST-822 (SEQ ID NO: 124); and in E. coli SURE: GST-206 (SEQ ID NO: 125). The recombinant fusion proteins MBP-506 (SEQ ID NO: 115), MBP-825 (SEQ ID NO: 116), GST-152 (SEQ ID NO: 122), GST-822 (SEQ ID NO: 124), PET-639 (SEQ ID NO: 119), PET-1084 (SEQ ID NO: 121) formed inclusion bodies that were harvested from the pellet following centrifugation of the bacterial sonicate. The fusion proteins PET-916 and GST-206 were found primarily in the supernatant and underwent considerable breakdown in culture. Protein fractions were checked by SDS-PAGE using Coomassie Blue staining and approximate concentrations determined by Western blotting.

ELISA sera were obtained from 38 Brazilian individuals with pulmonary tuberculosis and that were HIV positive (TBH), from 20 individuals with extrapulmonary tuberculosis and that were HIV negative (EP-TB), and from 17 healthy volunteers. Wells were coated with 200 ng of antigen in 50 μL of coating buffer (15 mM $Na_2CO_3$, 35 mM $NaHCO_3$ adjusted to pH 9.6) and incubated for 1 hour. Plates were then aspirated, 250 μL of blocking buffer (0.5% BSA and 0.1% Thimerosal (Aldrich, Milwaukee, Wis.) in phosphate-buffered saline at pH 7.4) were added to each well, and the plates were incubated for a further 2 hours. Plates were washed six times with 350 μL/well of washing solution (2 mL/L Tween 20 in PBS at pH 7.4) and serum was added at a 1:100 dilution in serum diluting buffer (blocking buffer with 2 mL/L Tween 20). Plates were incubated for 30 minutes and washed as before. 50 μL of a 1:50,000 dilution of HRP-Protein A (ZYMED, VWR) were added to each well. The plates were then incubated for 30 minutes and washed as before. 100 μL/well of TMB Microwell Peroxidase Substrate (Kirkegaard & Perry Laboratories) was added and the plates were incubated for 15 minutes in the dark. The reaction was stopped with 100 μL of 0.5 M $H_2SO_4$ and the plates were read immediately at 450 nm. The mean and standard deviations (SD) were calculated from the sera of uninfected control subjects (n=17) and the cut-off for positive results was calculated as greater than the mean plus 3 SD, and for high level responses, as the mean plus 6 SD.

Table 11 shows the overall seropositivity results for the nine full-length fusion proteins. When individual sera were considered, in the EP-TB group, 71% of sera contained antibodies against at least one antigen (or 82% if the TB lysate individuals are included) and in the TBH group, 66% of sera contained antibodies against at least one antigen (or 84% if the TB lysate individuals are included). Thus, specific antibody responses can be identified in the majority of the individual sera.

Measurement of the serum antibodies provides a way to determine the antigen reactivity. For the two groups, the number of serum samples that reacted positively to each antigen, and those which reacted at a high level, are presented in Table 11. For patients with EP-TB, antibodies against GST-822 were found in 60% of individual sera and a third of these were high-level responses. Specific antibody responses to three other antigens (PET-639, MBP-825, and MBP-506) of between 35% and 45% were also found in the EP-TB group. The other five antigens, as well as the M. tuberculosis lysate, elicited responses in fewer sera from EP-TB patients (35% or less).

For patients with TBH, antibodies against MBP-506 were found in 61% of individual sera and over two thirds of these were high-level responses. GST-822 was recognized in 42% of sera and almost two-thirds of the specific antibody responses were at a high level. The other six antigens, as well as the M. tuberculosis lysate, elicited responses in fewer sera from EP-TB patients (35% or less).

This study demonstrated that most of the patients infected with M. tuberculosis produced serum antibodies to a variety of antigens. As has been seen for individuals with pulmonary TB, Lyashchenko et al., Infect. Immun. 66:3936–3940, 1998, sera responses confirm that antigen recognition and strength of response were heterogeneous in both EP-TB and TBH groups. Encouragingly, the majority of sera contained specific antibodies to the small set of antigens tested. This finding suggests that, for these two groups previously considered refractory to serodiagnosis, the combination of only a few well-recognized antigens might greatly improve diagnostic success. MBP-506 and GST-822, the two highly reactive and most frequently recognized antigens identified in this study, are potentially valuable candidates for inclusion in a serodiagnostic test.

TABLE 11

Antigen Recognition by Serum Antibodies in TB Patients

| | Number (%) of responders | | | |
|---|---|---|---|---|
| | EP-TB | | HIV +, TB+ | |
| Antigen | Total[a] | High level[b] | Total[a] | High level[b] |
| TB lysate | 5 (25%) | 4 20%) | 13 34%) | 6 (30%) |
| PET-1084 | 0 (0%) | 0 (0%) | 4 11%) | 1 (3%) |
| PET-47 | 5 (25%) | 1 (5%) | 8 21%) | 3 (8%) |
| PET-916 | 3 (15%) | 3 15%) | 11 29%) | 4 (11%) |
| PET-639 | 8 (40%) | 2 10%) | 5 13%) | 4 (11%) |
| MBP-825 | 7 (35%) | 1 (5%) | 10 26%) | 5 (13%) |
| MBP-506 | 9 (45%) | 3 15%) | 23 61%) | 16 (42%) |
| GST-822 | 12 (60%) | 4 20%) | 16 42%) | 10 (26%) |
| GST-206 | 3 (15%) | 2 10%) | 5 13%) | 3 (8%) |
| GST-152 | 2 (10%) | 1 (5%) | 2 (5%) | 0 (0%) |

[a]TB patients having antibody levels greater or equal to cut-off, determined from negative control sera.
[b]TB patients having antibody levels greater or equal to cut-off plus 3 SD, determined from negative control sera.

C. Skin Test Assay

Alternatively, the presence of tuberculosis antibodies in a patient's body may be detected using an improved form of the tuberculin skin test, employing immunostimulatory peptides of the present invention. Conventionally, this test produces a positive result in one of the following conditions: the current presence of M. tuberculosis in the patient's body after exposure of the patient to M. tuberculosis and prior BCG vaccination. As noted above, if one group of immunostimulatory peptides is reserved for use in vaccine preparations, and another group reserved for use in the improved skin test, then the skin test will not produce a positive response in individuals whose only exposure to tuberculosis antigens was via the vaccine. Accordingly, the improved skin test would be able to properly distinguish between infected individuals and vaccinated individuals.

The tuberculin skin test consists of an injection of proteins from *M. tuberculosis* that are injected intradermally. The test is described in detail in Wyngaarden et al. (eds.), *Cecil Textbook of Medicine*, W. B. Saunders, Philadelphia, Pa., 1992. If the subject has reactive T-cells to the injected protein, then the cells will migrate to the site of injection and cause a local inflammation. This inflammation, which is generally known as delayed type hypersensitivity (DTH) is indicative of circulating *M. tuberculosis* antibodies in the patient. Purified immunostimulatory peptides according to the present invention may be employed in the tuberculin skin test using the methods described in Wyngaarden et al. (eds.), *Cecil Textbook of Medicine*, W. B. Saunders, Philadelphia, Pa., 1992.

D. Nucleic Acid Amplification

One aspect of the invention includes nucleic acid primers and probes derived from the sequences set forth in the attached sequence listing, as well as primers and probes derived from the full-length genes that can be obtained using these sequences. These primers and probes can be used to detect the presence of *M. tuberculosis* nucleic acids in body samples and thus to diagnose infection. Methods for making primers and probes based on these sequences are described in section V, above.

The detection of specific nucleic acid sequences of a pathogen in human body samples by polymerase chain reaction (PCR) amplification is discussed in detail in Innis et al., *PCR Protocols: A Guide to Methods and Applications*, Academic Press: San Diego, 1990, in particular, part four of that reference. To detect *M. tuberculosis* sequences, primers based on the sequences disclosed herein would be synthesized, such that PCR amplification of a sample containing *M. tuberculosis* DNA would result in an amplified fragment of a predicted size. If necessary, the presence of this fragment following amplification of the sample nucleic acid can be detected by dot blot analysis (see chapter 48 of Innis et al., *PCR Protocols: A Guide to Methods and Applications*, Academic Press: San Diego, 1990). PCR amplification employing primers based on the sequences disclosed herein may also be employed to quantify the amount of *M. tuberculosis* nucleic acid present in a particular sample (see chapters 8 and 9 of Innis et al., *PCR Protocols: A Guide to Methods and Applications*, Academic Press: San Diego, 1990). Reverse-transcription PCR using these primers may also be utilized to detect the presence of *M. tuberculosis* RNA, indicative of an active infection.

Alternatively, probes based on the nucleic acid sequences described herein may be labeled with suitable labels (such as $^{32}P$ or biotin-avidin enzyme linked systems) and used in hybridization assays to detect the presence of *M. tuberculosis* nucleic acid in provided samples.

X. USE OF CLONED MYCOBACTERIUM SEQUENCES TO RAISE ANTIBODIES

Monoclonal antibodies may be produced to the purified *M. tuberculosis* peptides for diagnostic purposes. Substantially pure *M. tuberculosis* peptide suitable for use as an immunogen is isolated from transfected or transformed cells as described above. The concentration of protein in the final preparation is adjusted, for example, by concentration on an Amicon filter device, to the level of a few milligrams per milliliter. Monoclonal antibody to the protein can then be prepared as described below.

A. Monoclonal Antibody Production by Hubridoma Fusion

Monoclonal antibody to epitopes of the *M. tuberculosis* peptides identified and isolated as described herein can be prepared from murine hybridomas according to the classical method of Kohler and Milstein, *Nature,* 256:495, 1975, or derivative methods thereof. Briefly, a mouse is repetitively inoculated with a few micrograms of the selected purified protein over a period of a few weeks. The mouse is then sacrificed, and the antibody-producing cells of the spleen isolated. The spleen cells are fused with mouse myeloma cells by means of polyethylene glycol, and the excess unfused cells are destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, *Enzymol,* 70:419, 1980, and derivative methods thereof. Selected positive clones can be expanded and their monoclonal antibody product harvested for use. Detailed procedures for monoclonal antibody production are described in Harlow and Lane, *Antibodies, A Laboratory Manual*, Cold Spring Harbor Laboratory, New York, 1988.

B. Antibodies Raised Against Synthetic Peptides

An alternative approach to raising antibodies against the *M. tuberculosis* peptides is to use synthetic peptides synthesized on a commercially available peptide synthesizer based upon the amino acid sequence of the peptides predicted from nucleotide sequence data.

In a preferred embodiment of the present invention, monoclonal antibodies that recognize a specific M. tuberculosis peptide are produced. Optimally, monoclonal antibodies will be specific to each peptide, i.e., such antibodies recognize and bind one M. tuberculosis peptide and do not substantially recognize or bind to other proteins, including those found in healthy human cells.

The determination that an antibody specifically detects a particular M. tuberculosis peptide is made by any one of a number of standard immunoassay methods; for instance, the Western blotting technique, Sambrook et al. (ed.), *Molecular Cloning: A Laboratory Manual*, 2nd ed., vol. 1–3, Cold Spring Harbor Laboratory Press, Cold Spring Harbor, N.Y., 1989. To determine that a given antibody preparation (such as one produced in a mouse) specifically detects one M. tuberculosis peptide by Western blotting, total cellular protein is extracted from a sample of human sputum from a healthy patient and from sputum from a patient suffering from tuberculosis. As a positive control, total cellular protein is also extracted from M. tuberculosis cells grown in vitro. These protein preparations are then electrophoresed on a sodium dodecyl sulfate polyacrylamide gel. Thereafter, the proteins are transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of the substrate 5-bromo-4-chloro-3-indolyl phosphate/nitro blue tetrazolium results in the production of a dense blue compound by immuno-localized alkaline phosphatase. Antibodies that specifically detect the M. tuberculosis protein will, by this technique, be shown to bind to the M. tuberculosis-extracted sample at a particular protein band (which will be localized at a given position on the gel determined by its molecular weight) and to the proteins extracted from the sputum from the tuberculosis patient. No significant binding will be detected to proteins from the healthy patient sputum. Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-tuberculosis protein binding. Preferably, no antibody would be found to bind to proteins extracted from healthy donor sputum.

Antibodies that specifically recognize a M. tuberculosis peptide encoded by the nucleotide sequences disclosed herein are useful in diagnosing the presence of tuberculosis antigens in patients.

All publications and published patent documents cited in this specification are incorporated herein by reference to the same extent as if each individual publication or patent application was specifically and individually indicated to be incorporated by reference.

Having illustrated and described the principles of the invention in multiple embodiments and examples, it should be apparent to those skilled in the art that the invention can be modified in arrangement and detail without departing from such principles. Therefore, the invention encompasses all modifications coming within the spirit and scope of the following claims.

What is claimed is:

1. A method of stimulating an immune response, comprising contacting a polypeptide capable of stimulating INF-γ production by T cells with a mononuclear cell obtained from a subject, wherein the polypeptide comprises an amino acid sequence selected from the group consisting of:

(a) an amino acid sequence encoded by a nucleic acid sequence shown in SEQ ID NO: 16;

(b) an amino acid comprising 10 or more contiguous amino acid residues of (a); and (c) an amino acid sequence that shares at least 80% sequence identity to the amino acid sequence of (a).

2. The method recited in claim 1, wherein the amino acid sequence is encoded by a nucleic acid sequence shown in SEQ ID NO: 124.

3. The method recited in claim 1, wherein the amino acid sequence comprises the amino acid sequence shown in SEQ ID NO: 138.

4. The method recited in claim 1, wherein the amino acid sequence consists of the amino acid sequence shown in SEQ ID NO: 138.

5. The method of claim 1, wherein the polypeptide capable of stimulating INF-γ production by T cells produces greater than 10 ng/ml of INF-γ.

6. A method of stimulating an immune response, comprising contacting a polypeptide capable of stimulating the production of INF-γ by T cells with a mononuclear cell obtained from a subject, wherein the polypeptide comprises an amino acid sequence that shares at least 80% sequence identity to an amino acid sequence encoded by a nucleic acid sequence shown in SEQ ID NO: 16.

7. The method of claim 6, wherein the polypeptide comprises an amino acid sequence that shares at least 85% sequence identity to an amino acid sequence encoded by the nucleic acid sequence shown in SEQ ID NO: 16.

8. The method of claim 7, wherein the polypeptide comprises an amino acid sequence that shares at least 90% sequence identity to amino acid sequence encoded by the nucleic acid sequence shown in SEQ ID NO: 16.

9. The method of claim 8, wherein the polypeptide comprises an amino acid sequence that shares at least 95% sequence identity to an amino acid sequence encoded by a nucleic acid sequence shown in SEQ ID NO: 16.

10. A method of stimulating an immune response, comprising contacting a polypeptide capable of stimulating the production of INF-γ by T cells with a mononuclear cell obtained from a subject, wherein the polypeptide comprises an amino acid sequence encoded by a nucleic acid sequence shown in SEQ ID NO: 16.

11. A method of stimulating an immune response, comprising contacting a polypeptide capable of stimulating the production of INF-γ by T cells with a mononuclear cell obtained from a subject, wherein the polypeptide comprises an amino acid sequence that shares at least 60% sequence identity to an amino acid sequence encoded by a nucleic acid sequence shown in SEQ ID NO: 124.

12. The method of claim 11, wherein the polypeptide comprises an amino acid sequence that shares at least 80% sequence identity to an amino acid sequence encoded by a nucleic acid sequence shown in SEQ ID NO: 124.

13. The method of claim 12, wherein the polypeptide comprises an amino acid sequence that shares at least 85% sequence identity to an amino acid sequence encoded by a nucleic acid sequence shown in SEQ ID NO: 124.

14. The method of claim 13, wherein the polypeptide comprises an amino acid sequence that shares at least 90% sequence identity to an amino acid sequence encoded by a nucleic acid sequence shown in SEQ ID NO: 124.

15. The method of claim 14, wherein the polypeptide comprises an amino acid sequence that shares at least 95% sequence identity to an amino acid sequence encoded by a nucleic acid sequence shown in SEQ ID NO: 124.

16. The method of claim 11, wherein the polypeptide is encoded by a nucleic acid sequence comprising a nucleic acid sequence shown in SEQ ID NO: 124.

17. The method of claim 11, wherein the polypeptide capable of stimulating INF-γ production by T cells produces greater than 10 ng/ml of INF-γ.

18. A method of stimulating an immune response, comprising contacting a polypeptide capable of stimulating the production of INF-γ by T cells with a mononuclear cell obtained from a subject, wherein the polypeptide comprises an amino acid sequence that shares at least 80% sequence identity to an amino acid sequence shown in SEQ ID NO: 138.

19. The method of claim 18, wherein the polypeptide comprises an amino acid sequence that shares at least 85% sequence identity to an amino acid sequence shown in SEQ ID NO: 138.

20. The method of claim 19, wherein the polypeptide comprises an amino acid sequence that shares at least 90% sequence identity to an amino acid sequence shown in SEQ ID NO: 138.

21. The method of claim 20, wherein the polypeptide comprises an amino acid sequence that shares at least 95% sequence identity to an amino acid sequence shown in SEQ ID NO: 138.

22. A method of stimulating an immune response, comprising contacting a polypeptide capable of stimulating INF-γ production by T cells with a mononuclear cell obtained from a subject, wherein the polypeptide comprises an amino acid sequence that has 10 or more contiguous amino acids encoded by a nucleic acid sequence shown in SEQ ID NO: 16.

23. A method of stimulating an immune response, comprising contacting a polypeptide capable of stimulating INF-γ production by T cells with a mononuclear cell obtained from a subject, wherein the polypeptide comprises an amino acid sequence encoded by a nucleic acid sequence that shares at least 75% sequence identity to a nucleic acid sequence shown in SEQ ID NO: 16.

24. The method of claim 23, wherein the polypeptide comprises an amino acid sequence encoded by a nucleic acid sequence that shares at least 90% sequence identity to the nucleic acid sequence shown in SEQ ID NO: 16.

25. The method of claim 24, wherein the polypeptide comprises an amino acid sequence encoded by the nucleic acid sequence shown in SEQ ID NO: 16.

26. A method of stimulating an immune response, comprising contacting a polypeptide capable of stimulating INF-γ production by T cells with a mononuclear cell obtained from a subject, wherein the polypeptide comprises an amino acid sequence encoded by a nucleic acid sequence that shares at least 75% sequence identity to a nucleic acid sequence shown in SEQ ID NO: 124.

27. The method of claim 26, wherein the polypeptide comprises an amino acid sequence encoded by a nucleic acid sequence that shares at least 90% sequence identity to a nucleic acid sequence shown in SEQ ID NO: 124.

28. The method of claim 27, wherein the polypeptide comprises an amino acid sequence encoded by a nucleic acid sequence shown in SEQ ID NO: 124.

* * * * *

UNITED STATES PATENT AND TRADEMARK OFFICE
CERTIFICATE OF CORRECTION

PATENT NO. : 6,572,865 B1
DATED : June 3, 2003
INVENTOR(S) : Francis E. Nano

It is certified that error appears in the above-identified patent and that said Letters Patent is hereby corrected as shown below:

<u>Title page,</u>
Item [56], References Cited, OTHER PUBLICATIONS, reference "Janssen et al.," "*Vaccine 12*:405-409" should be -- *Vaccine 12*:406-409 --.

<u>Column 29,</u>
Line 41, "logo" should be -- $\log_{10}$ --.

Signed and Sealed this

Twenty-third Day of December, 2003

JAMES E. ROGAN
*Director of the United States Patent and Trademark Office*

SEQUENCE LISTING

<160> NUMBER OF SEQ ID NOS: 169

<210> SEQ ID NO 1
<211> LENGTH: 267
<212> TYPE: DNA
<213> ORGANISM: Mycobacterium tuberculosis

<400> SEQUENCE: 1

```
acgcggacct cgaagttcat catcgagtga tacgtgccac acatctcggc gcagtggccc      60
acgaatgctc cggtcttggt gatttcttcg atctggaaga cgttgaccga gttgtttgcc     120
accgggttag gcatcacgtc acgcttgaac aagaactccg gcacccagaa tgcgtgtatc     180
acatcggctg aggccatttg gaattcgata cgcttgccgg acggcagcac cagcaccgga     240
atttcggtgc tggtgcccaa cgtctcg                                         267
```

<210> SEQ ID NO 2
<211> LENGTH: 487
<212> TYPE: DNA
<213> ORGANISM: Mycobacterium tuberculosis
<220> FEATURE:
<221> NAME/KEY: variation
<222> LOCATION: (1)..(487)
<223> OTHER INFORMATION: n = A, C, G, or T

<400> SEQUENCE: 2

```
ctgatacgac gccggcaagg actacgacga ggtggcacag aattcaatgc ggcgctcatc      60
ggaaccgacg tgcccgacgt cgttttgctc gacgacngat ggtggttcca tttcgccntc     120
```

```
agcggtgttc tgactgccct tgacgacctg ttcggccaag ttggggtgga cacaacggat      180
tacgtcgatt cgctgctggc cgactatgag ttcaacggcc gccattacgc tgtgccgtat      240
gctcgctcga cgccgctgtt ctactacaac aaggcggcgt ggcaacaggc cggcctaccc      300
gaccgcggac cgcaatcctg gtcagagttc gacgagtggg gtccggagtt acagcgcgtg      360
gtcggcgccg tcgatcggc gcacggctgc gntaacgccc acctcatctc gtggacgttt      420
cagggaccga actgggcatt cggcggtgcc tactccgaca gtggacatt gacattgacc       480 gagcccg                                                                487

<210> SEQ ID NO 3
<211> LENGTH: 511
<212> TYPE: DNA
<213> ORGANISM: Mycobacterium tuberculosis
<220> FEATURE:
<221> NAME/KEY: variation
<222> LOCATION: (1)..(511)
<223> OTHER INFORMATION: n = A, C, G, or T

<400> SEQUENCE: 3
ggcggccaga cngtcnggaa ctcgcnggcc attggtgtgg tgggaaccgc gatcctcgac      60
gcaccgcttc gcggtcttgc agtgttcgat gccaatctgc cggccgggac gctgccggat     120
ggcggcccgt tcaccgaggc tggtgacaag acctggcgtg tcgttccggg cactactccc     180
caggtcggtc aaggcaccgt caaagtgttc aggtataccg tcgagatcga aacggtctt     240 gatcccacaa tgtacggcgg tgacaacgca ttcgcccaga tggtcgacca gacgttgacc     300
aatcccaagg gctggaccca caatccgcaa ttcgcgttcg tgcggatcga cagcggaaaa     360
cccgacttcc ggatttcgct ggtgtcgccg acgacagtgc gcgggggtg tggctacgaa      420 ttccggctcg agacgtcctg ctacaacccc tcgttcggcg gcatggatcg ccaatcgcgg     480
gtgttcatca acgaggcgcg ctgggtacgc g                                    511

<210> SEQ ID NO 4
<211> LENGTH: 512
<212> TYPE: DNA
<213> ORGANISM: Mycobacterium tuberculosis
<220> FEATURE:
<221> NAME/KEY: variation
<222> LOCATION: (1)..(512)
<223> OTHER INFORMATION: n = A, C, G, or T

<400> SEQUENCE: 4
gtgtgcaacc agtgtgtgtn cgtgtgcgaa ccagtgtgta gtggtaacca ggacacgtt       60 gcaaaccagt gttggagtgc agtgttgcgt gcnagtgttg cncgttgcag tgtgncga      120 gccgagattg gaagttnccg acattaccgt tgccgacgtt gccctcgccg acgttcgcca     180
agcccaggtt gcgacacgc cggtgattgt gcgtgggca atgancgggc tgctggcccg      240
gccgaattcc aaggcgtcga tcggcacggt gttccaggac cgggccgctc gctacggtga     300
ccgagtcttc ctgaaattcg gcgatcagca gctgacctac cgcgacgcta acgccaccgc     360
caaccggtac gccgcggtgt tggccgcccg cggcgtcggc cccggcgacg tcgttggcat     420
catgttgcgt aactcaccca gcacagtctt ggcgatgctg ccacggtca agtgcggcgc      480 tatcgccggc atgctcaact accaccagcg cg                                   512

<210> SEQ ID NO 5
<211> LENGTH: 456
<212> TYPE: DNA
```

-continued

<213> ORGANISM: Mycobacterium tuberculosis
<220> FEATURE:
<221> NAME/KEY: variation
<222> LOCATION: (1)..(456)
<223> OTHER INFORMATION: n = A, C, G, or T

<400> SEQUENCE: 5
gcaacggaga ggtggactat gccggaccgg caccgcgaag gggttggtgc cggcccgggt 60
ggtgacggtg cacattctgc gcaattcgct gagttccggt ggtgaccttc ctgggcgcgg 120
agtctgggcg cgctgatggc ggagcgaktg tgaccgaagg aantcngttc aacatccacg 180
gcgtcggggg cgtgctgtat caagcggtca ccgtcaggag acgccgacgg tggtgtcgat 240
cgtgacggtg ctggtgctga tctacctgat caccaatctg ttggtggatc tgctgtatgc 300
ggccctggac gccgnngatn cgctatggct gagcacacgg ggttctggct cgatgcctng 360
cgcgggttgc gccggcgtcc taaantcgtg atcgcgcggc gctgakcctg ctgattcttg 420
tcgtggcggc gtttccgtcg ttgtttaccg cagccg 456

<210> SEQ ID NO 6
<211> LENGTH: 172
<212> TYPE: DNA
<213> ORGANISM: Mycobacterium tuberculosis
<220> FEATURE:
<221> NAME/KEY: variation
<222> LOCATION: (1)..(172)
<223> OTHER INFORMATION: n = A, C, G, or T

<400> SEQUENCE: 6
tcncttatcg cttcagctgg catctgccca aggaccgaat ctggacctat gacggccagc 60
tgaagatggc ccgcgacgaa gggcgttggc acgttcgctg gaccaccagc gggttgcatc 120
ccaagctagg cgaacatcaa aggttcgcgc tacgagccga cccgccgcgg cg 172

<210> SEQ ID NO 7
<211> LENGTH: 232
<212> TYPE: DNA
<213> ORGANISM: Mycobacterium tuberculosis
<220> FEATURE:
<221> NAME/KEY: variation
<222> LOCATION: (1)..(232)
<223> OTHER INFORMATION: n = A, C, G, or T

<400> SEQUENCE: 7
cttctcgcgc cagcncgtcc cgctgtccgg gatgncgcta ccggtcgtca gcgccaagac 60
ggtgcagctc aacgacggcg ggttggtgcg cacggtgcac ttgccggccc ccaatgtcgc 120
ggggctgctg agtgcggccn gcgtgccgct gttgcaaagc gaccacgtgg tgcccgccgc 180
gacggccccg atcgtcgaag gcatgcagat ccaggtgacc cgcaaatcgg at 232

<210> SEQ ID NO 8
<211> LENGTH: 173
<212> TYPE: DNA
<213> ORGANISM: Mycobacterium tuberculosis
<220> FEATURE:
<221> NAME/KEY: variation
<222> LOCATION: (1)..(173)
<223> OTHER INFORMATION: n = A, C, G, or T

<400> SEQUENCE: 8
gttcgncgcg ctcaaaaggt tgacgatggt cacgtcgcac gtgctggccg agaccaaggt 60
ggatttcggt gaagacctca aaganctcta ctcgnatcgt caaggccctc aacgacgacc 120
gaaaggattt cgtcacctcg ctgcagctgt tgctgacgtt cccatttccc aac 173

<210> SEQ ID NO 9
<211> LENGTH: 223
<212> TYPE: DNA
<213> ORGANISM: Mycobacterium tuberculosis
<220> FEATURE:
<221> NAME/KEY: variation
<222> LOCATION: (1)..(223)
<223> OTHER INFORMATION: n = A, C, G, or T

<400> SEQUENCE: 9
cctgttncaa cggtncnttc ncggaacgga cgacttctga tncgnnctcg gncgttccct    60
cgcaccggtc gatggtgatc aaggtcagcg tcttcgcggt ggtcatgctg ctggtggccg   120
ccggtctggt ggtggtattc ggggacttcc ggtttggtcc cacaaccgtc taccacgcca   180
ccttcaccga cncgtngcgg ctgaangcag gccagaaggt tcg                     223

<210> SEQ ID NO 10
<211> LENGTH: 120
<212> TYPE: DNA
<213> ORGANISM: Mycobacterium tuberculosis

<400> SEQUENCE: 10
caacgagatc gcacccgtga ttaggaggtg acggtggcag cgccgacccc gtcgaatcgg    60
atcgaagtaa cgctccgtag acgccagctc gtccgcgccg atgccgacct gccacccgtg   120

<210> SEQ ID NO 11
<211> LENGTH: 162
<212> TYPE: DNA
<213> ORGANISM: Mycobacterium tuberculosis
<220> FEATURE:
<221> NAME/KEY: variation
<222> LOCATION: (1)..(162)
<223> OTHER INFORMATION: n = A, C, G, or T

<400> SEQUENCE: 11
cggcttccag cgggtgcgcc aagcacggcc ggtccgtgcg agatcgtccc caatggcacg    60
ccggcgccca agacaccccc ggntaccgtg ccttcgtcgc gcaacctcgc gaccaacccc   120
gagatcgcca ccnnctacng ccgggacatg accgtggtgc gg                      162

<210> SEQ ID NO 12
<211> LENGTH: 133
<212> TYPE: DNA
<213> ORGANISM: Mycobacterium tuberculosis
<220> FEATURE:
<221> NAME/KEY: variation
<222> LOCATION: (1)..(133)
<223> OTHER INFORMATION: n = A, C, G, or T

<400> SEQUENCE: 12
gactggnccc gaygytgtgn ccgghncgth ggncghgchg cantcgaycc tggccgttgc    60
ttcggtgccg ggttgttcat cgccttcgac cagttgtggc gctggaacag catagtggcg   120
ctagtgctat cgg                                                      133

<210> SEQ ID NO 13
<211> LENGTH: 395
<212> TYPE: DNA
<213> ORGANISM: Mycobacterium tuberculosis

<400> SEQUENCE: 13
gcgcacactg cgcatgctgc cgtacccgcg ccaggcatga gtcttaggcc gaaatgcctg    60
gttaactggc gtgtcgtggt tgacccgcgg gcgtgcggct acagtgcatg ctgtgatcgg   120

-continued

```
cagtgggaga ggtagcggtg cggcgtaagg tgcggaggtt gactctggcg gtgtcggcgt    180
tggtggcttt gttcccggcg gtcgcggggt gctccgattc cggcgacaac aaaccgggag    240
cgacgatccc gtcgacaccg gcaaacgctg agggccggca cggacccttc ttcccgcaat    300
gtggcggcgt cagcgatcag acggtgaccg agctgacaag ggtgaccggg ctggtcaaca    360
ccgccaagaa gtcggtgggc tgccaatggc tggcg                              395
```

<210> SEQ ID NO 14
<211> LENGTH: 175
<212> TYPE: DNA
<213> ORGANISM: Mycobacterium tuberculosis
<220> FEATURE:
<221> NAME/KEY: variation
<222> LOCATION: (1)..(175)
<223> OTHER INFORMATION: n = A, C, G, or T

<400> SEQUENCE: 14

```
ccagnccncc naacntgtyn cgntctcayy tcgccgtcgc tgccggtncg tgtgtgcacc     60
atctgcaccg acccgtgkaa cytcgatcac ganactggna gagntcaggc atnaaagccg    120
gagtggcaca gcaacggtcg ctactggaat tggcgaagct ggatgctgag ctgac         175
```

<210> SEQ ID NO 15
<211> LENGTH: 265
<212> TYPE: DNA
<213> ORGANISM: Mycobacterium tuberculosis
<220> FEATURE:
<221> NAME/KEY: variation
<222> LOCATION: (1)..(265)
<223> OTHER INFORMATION: n = A, C, G, or T

<400> SEQUENCE: 15

```
gggctggatt cgaggctcng tgcatgccgt acgactaggg gtagcgccca gctgctcaat     60
accatcggtt ggataacaaa ggctgaacat gaatggcttg atctcacaag cgtgcggctc    120
ccaccgaccc cggcgcccct cgagcctggg ggctgtcgcg atcctgatcg cggcgacact    180
tttcgcgact gtcgttgcgg ggtgcgggaa aaaaccgacc acggcgagct ccccgagtcc    240
cgggtcgccg tcgccggaag cccac                                         265
```

<210> SEQ ID NO 16
<211> LENGTH: 170
<212> TYPE: DNA
<213> ORGANISM: Mycobacterium tuberculosis
<220> FEATURE:
<221> NAME/KEY: variation
<222> LOCATION: (1)..(170)
<223> OTHER INFORMATION: n = A, C, G, or T

<400> SEQUENCE: 16

```
cgccatgncg aagcgmaccc cggtccggaa ggcctgcaca gttctagccg tgctcgccgc     60
gacgctactc ctcgcctgcg gcggtcccac gcagccacgc agcatcacct tgacctttat    120
ncgcaacgcg caatcccagg ccaacgccga cgggatcatc gacaccgaca              170
```

<210> SEQ ID NO 17
<211> LENGTH: 181
<212> TYPE: DNA
<213> ORGANISM: Mycobacterium tuberculosis
<220> FEATURE:
<221> NAME/KEY: variation
<222> LOCATION: (1)..(181)
<223> OTHER INFORMATION: n = A, C, G, or T

<400> SEQUENCE: 17

```
accngttccc gccggnctna cncncggtgc cgttgcaccg gccanctgca gcctgcccg      60 acgccgaagt ggtgttcgcn ccgcggccgc ttcgaaccgc ccgggattgg cacggtcggc    120
aabgcattcg tcagcnntgc gctcgaaggt caacaagaat gtcggggtct acgcggtgaa    180
a                                                                   181
```

<210> SEQ ID NO 18
<211> LENGTH: 95
<212> TYPE: DNA
<213> ORGANISM: Mycobacterium tuberculosis

<400> SEQUENCE: 18

```
aggtkacggt ggcagcgccg accccgtcga atcggwtcga agaaygctcc gkacacgcca     60
gctgcgtccg ygccgatgcc gacctgccac ccgtg                                95
```

<210> SEQ ID NO 19
<211> LENGTH: 283
<212> TYPE: DNA
<213> ORGANISM: Mycobacterium tuberculosis
<220> FEATURE:
<221> NAME/KEY: variation
<222> LOCATION: (1)..(283)
<223> OTHER INFORMATION: n = A, C, G, or T

<400> SEQUENCE: 19

```
gcgcatgcgc aaccacttgg aatccgttga caatcgcatc ggtggccggc ccgtcggtga     60
ccgcntgcaa cagcgcggtg gtcaccnaca gcgaaaccag gtncttgtcg gctccggagg   120
tggcgatgac gtggcgccgg gaggtgttga gggtcatgtc gttttcgcgn taggtgccct   180
cgatgattga tgacggaaag cnncgtngaa anttggcnat agcggcgttt gtggtctgcn   240
atncgagcra ttnctgnctg tcagtgtagn cgtgtgtgat ggc                     283
```

<210> SEQ ID NO 20
<211> LENGTH: 156
<212> TYPE: DNA
<213> ORGANISM: Mycobacterium tuberculosis
<220> FEATURE:
<221> NAME/KEY: variation
<222> LOCATION: (1)..(156)
<223> OTHER INFORMATION: n = A, C, G, or T

<400> SEQUENCE: 20

```
tcttctacaa ggacgccttc gccaagcacc aggagctgtt cgacgacttg gncgtcaacg     60
tcaacaatgg cttgtccgat ctgtacragc aagwtcgagt cgctgccgnb cgcaacgcga   120
cgagatcatc gaggacctac accgttgcca cgaaca                             156
```

<210> SEQ ID NO 21
<211> LENGTH: 123
<212> TYPE: DNA
<213> ORGANISM: Mycobacterium tuberculosis
<220> FEATURE:
<221> NAME/KEY: variation
<222> LOCATION: (1)..(123)
<223> OTHER INFORMATION: n = A, C, G, or T

<400> SEQUENCE: 21

```
atnccgttcc actnccgcgg cagcagctgg ntttgcgcac acggtgaccc agtggcgntt     60
ggtggggcct cgctgacggc gagtntggnc gagcgtcctc ggtcggtgnc ctntcntccc   120
gcc                                                                 123
```

<210> SEQ ID NO 22
<211> LENGTH: 823
<212> TYPE: DNA
<213> ORGANISM: Mycobacterium tuberculosis
<220> FEATURE:
<221> NAME/KEY: variation
<222> LOCATION: (1)..(823)
<223> OTHER INFORMATION: n = A, C, G, or T

<400> SEQUENCE: 22

```
cggtcacgca attgatggcc gcgcgcaagg scgcatggtg agatgncca accacaccac      60
cggctgggtc cgcatggact tcgtggttcc cagtcgcggc ctgattgggt ggcgcaccga    120
cttcctcacc gagacccgtg ctccggtgt cgggcatgcg gtgttcgacg gatnaccggc    180
catgggcggg ggagkccggg cccgnccaca ccggttctct ggtatcggac cgggccggcg    240
ccatcacacc gttcgcgttg ctgcaactcg ccgatcgggg gcagttcttc gtcgagcccg    300
gccaacagan ccntacgagg ncantggctg ctgggatcaa cccccgtccg gaggacctcg    360
acatcaatgt cacccggagn agnangctga ccnaacatgc gctcatcgac cgcggatgtc    420
atcgagacgg tngccaagcc gctgcagctg gatctcgagc gcgccatgga gttatgtgcg    480
cccgacgaat gcgtcgaggt gaccccggag atcgtgcgga tccgcaaagt cgagctggcc    540
gccgccgccc gggctcgcag ccgggcgcgc accaaggcgc gtggctagca acttggcgcg    600
ctggccgcgc gagcgtaacg ccactgcgaa atccagcccg gcttttcgca gccgggttac    660
gctcgtgggg gtactggata gcctgatggg cgtgcccagc ccagtccgcc gcgtctgtgt    720
gacggtcggc gcgttggtcg cgctggcgtg tatggtgttg gccgggtgca cggtcagccc    780
gccgccggca ccccagagca ctgatacgcc gcgcagcaca ccg                      823
```

<210> SEQ ID NO 23
<211> LENGTH: 103
<212> TYPE: DNA
<213> ORGANISM: Mycobacterium tuberculosis

<400> SEQUENCE: 23

```
cttccggcgg gacaacaaca ggtctcaccg gcgccacacc ctgacacctg atcgcgtctg     60
ccgatcccgg tcggagcacc cgggttccac cgctgtgccc ccc                      103
```

<210> SEQ ID NO 24
<211> LENGTH: 207
<212> TYPE: DNA
<213> ORGANISM: Mycobacterium tuberculosis
<220> FEATURE:
<221> NAME/KEY: variation
<222> LOCATION: (1)..(207)
<223> OTHER INFORMATION: n = A, C, G, or T

<400> SEQUENCE: 24

```
gccaccggtt catcgcgtgg tgctggtcac cgccnggaan gcctcagcgg atcccctgct     60
gccaccgccg cctatccctg ccccagtctc ggcgccggca acagtcccgy ccgtgcagaa    120
cctcacggct ncthccgggc gggagcagca acaggttctc accggygccw ngyacccgca    180
ccgatcgcgt cgccgattcc ggtcgga                                        207
```

<210> SEQ ID NO 25
<211> LENGTH: 204
<212> TYPE: DNA
<213> ORGANISM: Mycobacterium tuberculosis
<220> FEATURE:
<221> NAME/KEY: variation
<222> LOCATION: (1)..(204)
<223> OTHER INFORMATION: n = A, C, G, or T

<400> SEQUENCE: 25

| | | | | | |
|---|---|---|---|---|---|
| ttncgcannc | gttcatccag | gtccactggt | gtcgcanctc | tcnntgatgc | accggttccg | 60
| gatatatgtc | nacatcnccs | tcstcgtcct | ggtgctggta | ctnacgaacc | tgatcgcgca | 120
| tttcaccaca | ccgtgngcga | gcatcgccac | cgtcccggcc | gccygcggtc | ggactggtga | 180
| tcttggtkcg | gagtagaggc | ctgg | | | | 204

<210> SEQ ID NO 26
<211> LENGTH: 207
<212> TYPE: DNA
<213> ORGANISM: Mycobacterium tuberculosis
<220> FEATURE:
<221> NAME/KEY: variation
<222> LOCATION: (1)..(207)
<223> OTHER INFORMATION: n = A, C, G, or T

<400> SEQUENCE: 26

| | | | | | |
|---|---|---|---|---|---|
| ataccngtca | tccngcacat | ngtcaacctn | gagtcggtnc | tcacctacga | ggcacgcccg | 60
| agatgcatca | ctggtgctcg | rtcagncctt | cacggcttgg | ccgccttccg | gtaggaccgt | 120
| hgcatgcccg | tcttcggcgc | ctcgggtgtt | cggtcctggc | tctcgggctg | ctggccnctg | 180
| cgccccaccc | cgcaccgggc | cggcttc | | | | 207

<210> SEQ ID NO 27
<211> LENGTH: 289
<212> TYPE: DNA
<213> ORGANISM: Mycobacterium tuberculosis
<220> FEATURE:
<221> NAME/KEY: variation
<222> LOCATION: (1)..(289)
<223> OTHER INFORMATION: n = A, C, G, or T

<400> SEQUENCE: 27

| | | | | | |
|---|---|---|---|---|---|
| ccgtgatngg | ccggnncgnc | atgttacggg | nagccgggna | ttgcgntacg | ccacggtgat | 60
| cgcgctggtg | gccgcgctgg | tggncngcgt | gtacgtgctc | tcgtccaccg | gtaataagcg | 120
| caccatcgtg | ggctacttca | cctctgctgt | cgggctctat | cccggtgacc | aggtccgcgt | 180
| cctgggcgtc | ccggtgggtg | agatcgacat | gatcgagccg | cggtcgtccg | acgtcaagat | 240
| cactatgtcg | gtgtccaagg | acgtcaaggt | gcccgtgsac | gtgcaggcc | | 289

<210> SEQ ID NO 28
<211> LENGTH: 198
<212> TYPE: DNA
<213> ORGANISM: Mycobacterium tuberculosis
<220> FEATURE:
<221> NAME/KEY: variation
<222> LOCATION: (1)..(198)
<223> OTHER INFORMATION: n = A, C, G, or T

<400> SEQUENCE: 28

| | | | | | |
|---|---|---|---|---|---|
| ttgnaccang | cctatcgcaa | gccaatcacc | tatgacacgc | tgtggcaggc | tgacaccgat | 60
| ccgctgccag | tcgtcttccc | cattgtgcaa | ggtgaactga | gcaangcaga | ccggacaaca | 120
| ggtatcgata | cgccgaatg | ccggcttgga | cccggtgaat | tatcagaact | tygcagtcac | 180
| gaacgacggg | gtgattttt | | | | | 198

<210> SEQ ID NO 29
<211> LENGTH: 149
<212> TYPE: DNA

-continued

<213> ORGANISM: Mycobacterium tuberculosis
<220> FEATURE:
<221> NAME/KEY: variation
<222> LOCATION: (1)..(149)
<223> OTHER INFORMATION: n = A, C, G, or T

<400> SEQUENCE: 29
tcacganggt rynacmgcaa cwcgaccgcc acgtcasgcc gccgcgcacg aagatcaccg 60
tgcctgcncg atgggtcgtg aacggaatag aaygcagcgg tgaggtcaan ygcgaagccg 120
ggaaccaaat ccggtgaccg cgtcggcat 149

<210> SEQ ID NO 30
<211> LENGTH: 210
<212> TYPE: DNA
<213> ORGANISM: Mycobacterium tuberculosis
<220> FEATURE:
<221> NAME/KEY: variation
<222> LOCATION: (1)..(210)
<223> OTHER INFORMATION: n = A, C, G, or T

<400> SEQUENCE: 30
ggacccgcca agcatcagcc ggtcaacagc cgccgccggt ggccaaagtt cgagcagccg 60
ccggtatcgt gctcggcccg gctagaccaa aaactttacg ccagcgcccg aagccacccg 120
actccaaggc ctcggcccgg ttgggttcgc acatgggtga gttctatatg ccctacccgg 180
gcacccggtt caaccaggaa accgtctcgc 210

<210> SEQ ID NO 31
<211> LENGTH: 255
<212> TYPE: DNA
<213> ORGANISM: Mycobacterium tuberculosis
<220> FEATURE:
<221> NAME/KEY: variation
<222> LOCATION: (1)..(255)
<223> OTHER INFORMATION: n = A, C, G, or T

<400> SEQUENCE: 31
cagnccgctg ncccggaact gttccagcag ctacaagacc ttcgacaacg tngcgcgtca 60
acctgcantc gagcgcaacc tctcggtggc gctcaacgag tgttcgccgg cttcaacccg 120
ctggacccgc gaaacctcga cgtgtccccg ctgccttcgc tggccaagcg cgccgccgac 180
atcctgcgcc aggacgtggg cgggcaggtc gacattttcg atgtcaatgt gcccaccatc 240
cagtacgacc agagc 255

<210> SEQ ID NO 32
<211> LENGTH: 164
<212> TYPE: DNA
<213> ORGANISM: Mycobacterium tuberculosis
<220> FEATURE:
<221> NAME/KEY: variation
<222> LOCATION: (1)..(164)
<223> OTHER INFORMATION: n = A, C, G, or T

<400> SEQUENCE: 32 aayncenggc crtcgacggt nccggttcnc rccaccggtc tatatccacc cgggtcnrca 60
ttmanantga ntmnccgccg gtgcggccgt cgagcgtgac ctggcatccc ctgagacgct 120
gctgggttgc cccggggagn tcgamantcg ggcatcgcac catc 164

<210> SEQ ID NO 33
<211> LENGTH: 237
<212> TYPE: DNA
<213> ORGANISM: Mycobacterium tuberculosis
<220> FEATURE:
<221> NAME/KEY: variation
<222> LOCATION: (1)..(237)
<223> OTHER INFORMATION: n = A, C, G, or T

<400> SEQUENCE: 33

| | | | | |
|---|---|---|---|---|
| acggacggca | acgggatgcg | acccgatccc | accggtcgcc | acgagggacg ctacttcgtc | 60 |
| gccgggcagc | cganccgacc | gtcngttcng | cganggcgac | ngccgaagcc gttgaccccac | 120 |
| nttggtcagc | agcagctgga | tsagtcaggt | gccgttggtg | tttcgccgtc agcggtgtcg | 180 |
| gggtgggtgc | gttctgggca | ccgtcgactg | tggtgggcgc | tngcgggcgn tggtggc | 237 |

<210> SEQ ID NO 34
<211> LENGTH: 371
<212> TYPE: DNA
<213> ORGANISM: Mycobacterium tuberculosis
<220> FEATURE:
<221> NAME/KEY: variation
<222> LOCATION: (1)..(371)
<223> OTHER INFORMATION: n = A, C, G, or T

<400> SEQUENCE: 34

| | | | | | |
|---|---|---|---|---|---|
| cggatgctcg | gcctccggta | cccaactcga | actcgcgccc | acngcggacn gcagggccgc | 60 |
| ggttggcacc | accagcgaca | tcaatcangc | aggatcccgc | cacgttgcaa gacggcggca | 120 |
| atcttcgcct | gtcgctcacc | gactttccgc | ccaacttcaa | catcttgcac atcgacggca | 180 |
| acaacgccga | ggtcgcggcg | atgatgaaag | ccaccttgcc | gcgcgcgttc atcatcggac | 240 |
| cggacggctc | gacgacggtc | gacaccaact | acttcaccag | catcgagctg accaggaccg | 300 |
| ccccgcaggt | ggtcacctac | accatcaatc | ccgaggcggt | gtggtccgac gggaccccga | 360 |
| tcacctggcc | g | | | | 371 |

<210> SEQ ID NO 35
<211> LENGTH: 26
<212> TYPE: DNA
<213> ORGANISM: Mycobacterium tuberculosis
<220> FEATURE:
<221> NAME/KEY: variation
<222> LOCATION: (1)..(26)
<223> OTHER INFORMATION: n = A, C, G, or T

<400> SEQUENCE: 35
gagaactccg ggccganttt tggaca                                         26

<210> SEQ ID NO 36
<211> LENGTH: 202
<212> TYPE: DNA
<213> ORGANISM: Mycobacterium tuberculosis

<400> SEQUENCE: 36

| | | | | |
|---|---|---|---|---|
| tgtcggtagc | gttcgcgtcc | atgattgctc | ttgcaacgct | gttgacgctt atcaatcaag | 60 |
| tcgtcggcac | tccgtatatt | cccggtggcg | attctcccgc | cgggaccgac tgctcggagc | 120 |
| tggcttcgtg | ggtatcgaat | gcggcgacgg | ccaggccggt | tttcggagat aggttcaaca | 180 |
| ccggcaacga | ggaagcgcct | tg | | | 202 |

<210> SEQ ID NO 37
<211> LENGTH: 319
<212> TYPE: DNA
<213> ORGANISM: Mycobacterium tuberculosis
<220> FEATURE:
<221> NAME/KEY: variation
<222> LOCATION: (1)..(319)

```
<223> OTHER INFORMATION: n = A, C, G, or T

<400> SEQUENCE: 37 ctantttag  aytnngtcgt  gacatatccg  ctgtacgcgt  gggacggncc  attattggat      60
aatgcgtgat  aagcaccaca  agaantgatt  ncctatggat  attgtcggta  ncgttcgcgt    120
ccatgattgc  tcttgcaacg  ctgttgacgc  ttatcaatca  agtcgtcggc  actccgtata    180
ttcccggtgg  cgattctccc  gccgggaccg  actgctcgga  gctggcttcg  tgggtatcga    240
atgcggcgac  ggccaggccg  gttttcggag  ataggttcaa  caccggcaac  gaggaagcng    300
ccttggcggc  tcgggctt                                                      319

<210> SEQ ID NO 38
<211> LENGTH: 263
<212> TYPE: DNA
<213> ORGANISM: Mycobacterium tuberculosis

<400> SEQUENCE: 38
ggtacttgtc  gtcgatggac  tcccggtctc  gattcaggaa  cagcgtcccg  acgacaccgg      60
ctcccaccag  cccgagaaac  gccaccacgc  cgcgagcgcc  caccacagtc  gacggtgcca    120
gaacgcacca  cccgacacgt  gacggcgaaa  caccaacggc  acctgactga  tgccagctgc    180
tgctgaccaa  gtgggcacgc  tcggcgcgcc  tcggaacgag  tcgtcgctgc  cgcgacgaag    240
acgcctcggc  gacgtggatc  ggg                                                263

<210> SEQ ID NO 39
<211> LENGTH: 841
<212> TYPE: DNA
<213> ORGANISM: Mycobacterium tuberculosis
<220> FEATURE:
<221> NAME/KEY: variation
<222> LOCATION: (1)..(841)
<223> OTHER INFORMATION: n = A, C, G, or T

<400> SEQUENCE: 39
gcgttgcgcg  ccctcgagca  gtcnnttggc  ggcgatcccg  agacaatgat  tcccgacatc      60
cggtacacac  cgaaccccaa  cgatgcgccg  ggcggcccgc  tggtagaaag  gggaaatcgc    120
cagtgctgac  tcgcttcatc  cgacgccagt  tgatcctttt  tgcgatcgtc  tccgtagtgg    180
caatcgtcgt  attgggctgg  tactacctgc  gaattccgag  tctggtgggt  atcgggcagt    240
acaccttgaa  ggccgacttg  cccgcatcgg  gtggcctgta  tccgacggcc  aatgtgacct    300
accgcggtat  caccattggc  aaggttactg  ccgtcgagcc  caccgaccag  ggcgcacgag    360
tgacgatgag  catcgccagc  aactacaaaa  tcccgtcga  tgcctcggcg  aacgtgcatt    420
cggtgtcagc  ggtgggcgag  cagtacatcg  acctggtgtc  caccggtgct  ccgggtaaat    480
acttctcctc  cggacagacc  atcaccaagg  gcaccgttcc  cagtgagatc  gggcggcgc     540 tggacaattc  caatcgcggg  ttggccgcat  tgcccacgga  gaagatcggc  ttgctgctcg    600
acgagaccgc  gcaagcggtg  ggtgggctgg  gacccgcgtt  gcaacggttg  gtcgattcca    660
ctcaagcgat  cgtcggtgac  ttcaaaacca  acattggcga  cgtcaacgac  atcatcgaga    720
actccgggcc  gattttggac  agccaggtca  cacgggtga  tcagatcgac  ngctgggcgc     780
gcaaattgaa  caatctggcc  gcacagaccg  cgaccaggga  tcagaacgtg  cgaagcatcc    840
t                                                                          841

<210> SEQ ID NO 40
<211> LENGTH: 209
```

<212> TYPE: DNA
<213> ORGANISM: Mycobacterium tuberculosis
<220> FEATURE:
<221> NAME/KEY: variation
<222> LOCATION: (1)..(209)
<223> OTHER INFORMATION: n = A, C, G, or T

<400> SEQUENCE: 40

```
gcggttggca ccaccagcga naatcagcag gndcccgcca cgttgcaaga cggcggcaat      60
cttcgcctgt cgctcaccga ctttccgccc aacttcaaca tcttgcacat cgacggcaab    120
aabgccgagg tcgcggcgat gatgaaagcc accttgccgc gcgcgttcat catcggaccg    180
gacggctcga cgacggtcga caccaacta                                       209
```

<210> SEQ ID NO 41
<211> LENGTH: 167
<212> TYPE: DNA
<213> ORGANISM: Mycobacterium tuberculosis
<220> FEATURE:
<221> NAME/KEY: variation
<222> LOCATION: (1)..(167)
<223> OTHER INFORMATION: n = A, C, G, or T

<400> SEQUENCE: 41

```
agatcgtcag tgagcagaac cccgccaaac cggccgcccg aggtgttgtt cgagggctga      60
aggcgctgct cgcgacggtc gntgctggcc gtcgtcggga tcgggcttng gctcgcgctg    120
tacttcacgc cggcgatgtc ggcccgcgag atcgtgnatc atcggga                  167
```

<210> SEQ ID NO 42
<211> LENGTH: 221
<212> TYPE: DNA
<213> ORGANISM: Mycobacterium tuberculosis
<220> FEATURE:
<221> NAME/KEY: variation
<222> LOCATION: (1)..(221)
<223> OTHER INFORMATION: n = A, C, G, or T

<400> SEQUENCE: 42

```
ccagntcctc nnatatcgac accctcnacn aagaccgctt cgcgagatca acnctcagat      60
atncnnacta tcnccnntnc acgcacacct caacatnana naatngaact atngncttcg    120
cctcaccacc aaggttcagg ttancggctg ncgtttkctc tkcgccggct cgaacacgcc    180
atcgtgcgcc ggkacacccg gatgtttgac gacccgctgc a                         221
```

<210> SEQ ID NO 43
<211> LENGTH: 117
<212> TYPE: DNA
<213> ORGANISM: Mycobacterium tuberculosis
<220> FEATURE:
<221> NAME/KEY: variation
<222> LOCATION: (1)..(117)
<223> OTHER INFORMATION: n = A, C, G, or T

<400> SEQUENCE: 43

```
cggyccgnnc aayyygncgc gchncggygy agaggtcgny aaggtcgcca aggtaacgct      60
gatcgayggg nacangcaag tattggtgna cttcaccgtg ghthgcthgc tgtyagc       117
```

<210> SEQ ID NO 44
<211> LENGTH: 385
<212> TYPE: DNA
<213> ORGANISM: Mycobacterium tuberculosis

<400> SEQUENCE: 44

```
gaacctcctc gcccgcgctt ggcctagcat taatcgactg gcacgacagt tgcccgactg     60
ggtacacggc atggacgcaa cgcgaatgaa tgtgagttag ctcactcatt aggcacccca    120
ggcgttgaca ctttatgctt ccggctcgtg tagttgtgtg ggaattgtgg agcggataac    180
aatttcgacg acgaggaaac agctgtagac atggattgac gaatttgaat acgactcact    240
ataggaattc gagctcggta cccggggatc ctctagagtc cttcgccgcg ggtcgccacc    300
atcagggcca gtgcgatcgc aagcgcgggg taccgggcgc catagtcttc agcatcggcg    360
tgttgaccgc agagaccgga cgggg                                         385
```

<210> SEQ ID NO 45
<211> LENGTH: 285
<212> TYPE: DNA
<213> ORGANISM: Mycobacterium tuberculosis
<220> FEATURE:
<221> NAME/KEY: variation
<222> LOCATION: (1)..(285)
<223> OTHER INFORMATION: n = A, C, G, or T

<400> SEQUENCE: 45

```
cccgcagcag tacccgcagn cccacacccg ctatncgcag cccgaacagt tcggtgcaca     60
gcccacccna gctcggcgtg cccggtcagt acggccaata ccagcagccg ggccaatatg    120
nccagccggn acagtnacgn ccagcccggc cagtacgcna ccgcccggtc agtacccgg    180 gcaatacggc ccgtatgncc agtcgggtca ggggtcgaag cgttcggttg cggtgatcgg    240
cggcgtgatc gccgtgatgg ccgtgctgtt catcggcgcg gttct                   285
```

<210> SEQ ID NO 46
<211> LENGTH: 186
<212> TYPE: DNA
<213> ORGANISM: Mycobacterium tuberculosis
<220> FEATURE:
<221> NAME/KEY: variation
<222> LOCATION: (1)..(186)
<223> OTHER INFORMATION: n = A, C, G, or T

<400> SEQUENCE: 46

```
gcncgtgncc gtgccgcccg gttgaacgtg agcngctgnc natngcccca gccgagacga     60
gaacgtcccc gaggagtatg cagactggga agacgccgaa gactatgacg actatgacga    120
ctatgaggcc gcagaccagg aggccgcacg gtcggcatcc tggcgacggc ggttgcgggt    180 ncggtt                                                              186
```

<210> SEQ ID NO 47
<211> LENGTH: 409
<212> TYPE: DNA
<213> ORGANISM: Mycobacterium tuberculosis
<220> FEATURE:
<221> NAME/KEY: variation
<222> LOCATION: (1)..(409)
<223> OTHER INFORMATION: n = A, C, G, or T

<400> SEQUENCE: 47

```
gtcgctgaat gtgttgtcgg agaccgtnga tcagacctat ccgcacctga gcgccgccnt     60
cgacgggntg gctaagttct ccgacaccat cggcaagcgc gacgagcaga ntcacgcacc    120
tactagccca ggccaaccag gtggccagca tcctgggtga tcgcagtgag caggtcgacc    180
gcctattggt caacgctaag accctgatcc ccgcgttcaa cgagcgcggc cgcgcggtcg    240
acgccctgct ggggaacatc tccgctttct cgncccaggt gcaaaacctt natcaacgac    300
aacccgaacc tgaaccatgt gctcgnnnag ctgcgcatcc tcancgacct gttggtcgac    360
```
cgcaaggagg atttggctga aaccctgacg atcttgggca gattcagcg          409

<210> SEQ ID NO 48
<211> LENGTH: 464
<212> TYPE: DNA
<213> ORGANISM: Mycobacterium tuberculosis
<220> FEATURE:
<221> NAME/KEY: variation
<222> LOCATION: (1)..(464)
<223> OTHER INFORMATION: n = A, C, G, or T

<400> SEQUENCE: 48
agnccgtgca ctggaacttc ggctcgatgt ctccgatgtg gacggcaagc tgatgatctc      60
ccggttggan gtcgattcga tgasaaatgn cttggcggct ggtggtgttc gatgncctgg     120
caccactggc cacgatcgcc gccntggccg cgatcggcgn cttngctcgg ctggcccctg     180
tggtgggttt cgacgtgctc ggtgttggtg ctgctggtgg tcgaaggtgt ggcaatcaac     240
nttctggctg ttgcgtcgtg attcggtaac cgtcggtacc gacgacgatg cgcccgggct     300
gcgactggcc gttgtcttcc tgtgcgccgc gcgatctcg gcggcggtgg tgactgggta     360
cctgcgctgg acgacaccgg accgcgactt caatcgggat tcccgggaag tggtgcatct     420
tgccacgggg atggccgaga cggtcgcgtc attctccccg agcg                      464

<210> SEQ ID NO 49
<211> LENGTH: 423
<212> TYPE: DNA
<213> ORGANISM: Mycobacterium tuberculosis
<220> FEATURE:
<221> NAME/KEY: variation
<222> LOCATION: (1)..(423)
<223> OTHER INFORMATION: n = A, C, G, or T
<400> SEQUENCE: 49
gtccaaggcc gtagcccacc tcctggaagt cgtaccacgt cgactcgacc aggacggctg      60
cantcagcna cttcgtcaac ccggcgatca tcaacntgca cctacggcag tgtgnacgca     120
ccccggacca tcgcactggc cggggnttca cacgccgaac actgnctgac cgcactggat     180
ctgctnggtc gcatgcacca cttcaaggtg gtgacgtacc tcaaaatggg ttkcccgttg     240
tccaccgagg aagtcccgct gatncatggg caataacgct ccctatccgc agtgtcacca     300
gtgggtgcaa gcggcgatgg ccaagttggt cgctgaccac cccgactacg ttttcacaac     360
ctcgactcga ccgtggaaca tcaaacccgg cgatgtgatg ccagcaacct atgtcgggat     420
ctg                                                                    423

<211> LENGTH: 279
<212> TYPE: DNA
<213> ORGANISM: Mycobacterium tuberculosis

<400> SEQUENCE: 50
cggtcgagcc gatgaacgtc tgcagttcac cgcaaccacg ctcagcggtg ctcccttcga      60
tgcgcaagcc tgcaaggcaa tgccgcggtg ttgtggttct ggacgccgtg gtgcccgttc     120
tgcaactgtc agaagccccc agccgcagcc aggtagcggc cgctaatccg gcggtcacct     180
tcgtcggaat cgccacccgc gccgacgtcg ggcgatgca gagctttgtc tcgaagtaca     240
acctgaattt caccaacctc aatgacgccg atggtgtga                            279

<210> SEQ ID NO 51

<211> LENGTH: 331

-continued

<212> TYPE: DNA
<213> ORGANISM: Mycobacterium tuberculosis
<220> FEATURE:
<221> NAME/KEY: variation
<222> LOCATION: (1)..(331)
<223> OTHER INFORMATION: n = A, C, G, or T

<400> SEQUENCE: 51

```
cggcccgscg gcgccntggt gaagcttggm gmmtgggtgn agcgcagctg cccaccacac     60
ggraccnngg tgcggacgcg gntgacgcgc ctggtggtca gcatcgtggc cggtctgctg    120
ttgtatgcca gcttcccgcc gcgcaactgc tggtnggcgg cggtggttgs gctncgcatt    180
gctggcctgg gtgctgaccc accgcgcgac gacaccggtg ggtgggctgg gctacggcct    240
gctattcggc ctggtgttct acgtctcgtt gttgccgtgg atcggcgagc tggtgnnccc    300
cgggccctgg ttggcactgg cgacgacgtg c                                   331
```

<210> SEQ ID NO 52
<211> LENGTH: 507
<212> TYPE: DNA
<213> ORGANISM: Mycobacterium tuberculosis

<400> SEQUENCE: 52

```
tgtattcccg tcgatgcgtt gctgcaggta ggccttgaaa tcgttggggg tcacgacgcg     60
gacctcgaag ttcatcatcg agtgatacgt gccacacatc tcggcgcagt ggcccacgaa    120
tgctccggtc ttggtgattt cttcgatctg gaagacgttg accgagttgt ttgccaccgg    180
gttaggcatc acgtcacgct tgaacaagaa ctccggcacc cagaatgcgt gtatcacatc    240
ggctgaggcc atttggaatt cgatacgctt gccggacggc agcaccagca ccggaatttc    300
ggtgctggtg cccaacgtct cgaccttgtc gaaattcagg taggtccggt cctcggtgtt    360
gagcccgcgc accggcccga ccagctcttc gccgtacttg tccttgccct ctggcttgga    420
aaccatggcg cgcttgcgct ccggatcggc accatcatag gtcagtgtgc cgtctttgaa    480
gttcaccctt tgatagccaa acttcca                                        507
```

<210> SEQ ID NO 53
<211> LENGTH: 293
<212> TYPE: DNA
<213> ORGANISM: Mycobacterium tuberculosis

<400> SEQUENCE: 53

```
ccacacaaca caaatctacg tcgtaatgca gtcgtaagtc catccgacgt cgatggcaag     60
gacagcaccc gacggccaac ggcatataca tcgtcggctc gccggtcaca agcacatcat    120
catggactcg tccactacgg cgtacccgtc aactcgccca acggatatcg caccgatgtc    180
gactggccac ccagatctcc tacagcggtg tcttcgtgca ctcagcgccg tggtcggtgg    240
gggctcaggg ccacaccaac accagccatg gctgcctgaa cgtcagcccg agc           293
```

<210> SEQ ID NO 54
<211> LENGTH: 820
<212> TYPE: DNA
<213> ORGANISM: Mycobacterium tuberculosis
<220> FEATURE:
<221> NAME/KEY: variation
<222> LOCATION: (1)..(820)
<223> OTHER INFORMATION: n = A, C, G, or T

<400> SEQUENCE: 54

```
cgccgccggc gngcgctacc ggtgcgggag ggtacaccca agcantccgg gaccggccgt     60
```

-continued

| | |
|---|---|
| cycgccggga acgccgtgct cctacacacc ggcggcgggc gcgttgccac ggcccgacac | 120 |
| cccactaccc tgncgcgggc gccaccgttg gcccgttcgg tggacccgac ttcccggcac | 180 |
| cgctcgatgt ccagccgtcg ccgcctaatc ccgatgggcc gccgccgacg ccgggcatcc | 240 |
| taagtgctgg gcggccgggc gagccggctc cggctgttcc ggncataccg atgccsctgc | 300 |
| cgccgaacnn nnnnnnnnnt gcacgcaccc aaccgcttga gccgtttcct gacgggacgg | 360 |
| gaggtagcaa ccaatgagca ccatcttcga catccgsagc ctgcgactgy cgaaactgtc | 420 |
| tgcaaaggta gtggtcgtcg gcgggttggt ggtggtcttg gcggtcgtgg ccgctgcggc | 480 |
| cggcgcgcgg ctctaccgga aactgactac cactaccgtg gtcgcrtatt tnctstgagg | 540 |
| cgctcgcgct gtacccagga gacaaagtcc agatcatggg tgtgcgggtc ggttctatcg | 600 |
| acaagatcga gccggccggc gacaagatgc gagtcacgtt gcactacagc aacaaatacc | 660 |
| aggtgccggc cacgnctacc gcgtcgatcc tcaaccccag cctggtggcc tcgcgcacca | 720 |
| tccagctgtc accgccgtac accggcggcc cggtcttgca agacgcgcg gtgatcccaa | 780 |
| tcgagcgcac ccaggtgccc gtcgagtggg atcagttgcg | 820 |

<210> SEQ ID NO 55
<211> LENGTH: 117
<212> TYPE: DNA
<213> ORGANISM: Mycobacterium tuberculosis

<400> SEQUENCE: 55

| | |
|---|---|
| cagccacctc gttcgccgcc gacatcgact atcagccgac ccggccactg ctgacctgat | 60 |
| cgccaacagc tggaggccct accggctgca gttcaattca cccgctgcgg gtcggcg | 117 |

<210> SEQ ID NO 56
<211> LENGTH: 242
<212> TYPE: DNA
<213> ORGANISM: Mycobacterium tuberculosis

<400> SEQUENCE: 56

| | |
|---|---|
| aggtgtcgtg cttcatgcct ggcgcccaat ccagtttcta caccgactgg tatcacccTT | 60 |
| cgcagacaaa cggccagaac tacacctaca agtgggagac cttccttacc acacagatgc | 120 |
| ccgcctggct acaggccaac aaggcgtgtc ccccacaggc aacgcggcgg tgggtctttc | 180 |
| gatctcgggc ggttccgcgc tgaccctggc cgcgtactac ccgcagcagt tcccgtacgc | 240 |
| cg | 242 |

<210> SEQ ID NO 57
<211> LENGTH: 345
<212> TYPE: DNA
<213> ORGANISM: Mycobacterium tuberculosis

<400> SEQUENCE: 57

| | |
|---|---|
| tgctgcagat agccaaggat cccgaggtcg tgattgatat cacgtctttc cagtggaatt | 60 |
| ggaagtttgg ctatcaaagg gtgaacttca agacggcac actgacctat gatggtgccg | 120 |
| atccggagcg caagcgcgcc atggtttcca gccagaggg caaggacaag tacggcgaag | 180 |
| agctggtcgg gccggtgcgc gggctcaaca ccgaggaccg gacctacctg aatttcgaca | 240 |
| aggtcgagac gttgggcacc agcaccgaaa ttccggtgct ggtgctgccg tccggcaagc | 300 |
| gtatcgaatt ccaaatggcc tcagccgatg tgatacacgc attct | 345 |

<210> SEQ ID NO 58

<210> SEQ ID NO 58
<211> LENGTH: 262
<212> TYPE: DNA
<213> ORGANISM: Mycobacterium tuberculosis
<220> FEATURE:
<221> NAME/KEY: variation
<222> LOCATION: (1)..(262)
<223> OTHER INFORMATION: n = A, C, G, or T

<400> SEQUENCE: 58

| | | | | | |
|---|---|---|---|---|---|
| cngactccaa | cnagtgcgnt | caancngntg | tnccngacaa | gaaggttcct | acatccgcaa | 60 |
| ntcggtgnaa | ngccactgtg | gatgcctacg | acggaacggt | cacgctgtac | caacaggacg | 120 |
| naaaaggatc | cggtgctcaa | ggcctggatg | caggtcttcc | ccggcacggt | aaagcctaag | 180 |
| agcgacattg | cgccggagct | tgccgagcan | ctgcggtatc | ccgaggacct | gttcaaggtg | 240 |
| cagcgcatgt | tgttggccaa | at | | | | 262 |

<210> SEQ ID NO 59
<211> LENGTH: 241
<212> TYPE: DNA
<213> ORGANISM: Mycobacterium tuberculosis
<220> FEATURE:
<221> NAME/KEY: variation
<222> LOCATION: (1)..(241)
<223> OTHER INFORMATION: n = A, C, G, or T

<400> SEQUENCE: 59

| | | | | | |
|---|---|---|---|---|---|
| ccaccannna | acrrcacagc | tccggccrrc | cgtncgcagg | ccacccgcan | cgtagtgctc | 60 |
| aaattcttcc | aggacctcgg | tggggyacat | ccgtccacct | ggtacaaggc | cttcaactac | 120 |
| aacctcgcga | cctcgcagcc | catcaccttc | gacacgttgt | tcgtgcccgg | caccacgcca | 180 |
| ctggacagca | tctaccccat | cgttcagcgc | gagctggcac | gtcagaccgg | tttcggtgcc | 240 |
| g | | | | | | 241 |

<210> SEQ ID NO 60
<211> LENGTH: 243
<212> TYPE: DNA
<213> ORGANISM: Mycobacterium tuberculosis
<220> FEATURE:
<221> NAME/KEY: variation
<222> LOCATION: (1)..(243)
<223> OTHER INFORMATION: n = A, C, G, or T

<400> SEQUENCE: 60

| | | | | | |
|---|---|---|---|---|---|
| ccggcggatc | tgcgtgacga | ntgtatncca | cggnactacc | cgcggtcctt | cctcnantnc | 60 |
| cgccggncca | gncgcagnct | ncngatgtcc | ngctataacc | tgcgcgatcg | ccgccgggct | 120 |
| gcccgacaac | acggtgngcg | ccgccgctgc | ttccgccaat | tctgggtgnc | ggcatnccgg | 180 |
| cagcgcccgg | cccagcactg | agaggggac | gttgatgcgg | tggccgacgg | cgtggctgct | 240 |
| ggc | | | | | | 243 |

<210> SEQ ID NO 61
<211> LENGTH: 2348
<212> TYPE: DNA
<213> ORGANISM: Mycobacterium tuberculosis
<220> FEATURE:
<221> NAME/KEY: variation
<222> LOCATION: (1)..(2348)
<223> OTHER INFORMATION: n = A, C, G, or T

<400> SEQUENCE: 61

| | | | | | |
|---|---|---|---|---|---|
| gcgctgtcat | tcggacttcg | gaccgcgttg | gcggtggtgc | tgatcatgaa | nctacgacgg | 60 |
| cgccaccggc | agcttcccgt | catgggtgct | ctatccctgt | gcgctggcca | tgatggtgtt | 120 |

-continued

```
ctcgaagtcg ttcagcgtgc tgcgcagcgc agtgacaccg agggtgatgc cgccaaccat    180
cgacttggtc cgggtcaact cacggctgac cgtgttcggc ctgctcggcg gcaccatcgc    240
tggtggcgcg attgcggccg gagtcgaatt cgtctgcacc cacctgttcc agctgccggg    300
cgcgttgttc gtcgtcgtcg cgatcaccat cgctggcgct tcgctgtcga tgcgcattcc    360
gcgctgggtc gaggtgacca gcggtgaggt cccggccaca ttgagctacc accgggatag    420
gggcagacta cggcgacngc tggccggagg aagtcaagaa cctcggcgga acactccgac    480
aaccgttggg ccgcaacatc attacctccc tgtggggtaa ctgcaccatc aaggtgatgg    540
tcggctttct gttcttgtat ccggcgtttg tcgccaaggc gcacgaagcc aacgggtggg    600
tgcaattggg catgctgggc ctgatcggcc ggcggccgc ggtcggcaac ttcgccggca    660
atttcaccag cgcacgcctg cagctaggca ggccagctgt gctggtngtg cgctgcaccg    720
tgctagttac cgtgttagcc atcgcggccg cggtggccgg cagcctggca gcgacagcga    780
ttgccaccct gatcacggca gggtccagtg ccattgctaa agcctcgctg gacgcctcgt    840
tgcagcacga cctgcccgag gagtcgcggg catcgggggtt tgggcgttcc gagtcgactc    900
ttcagctggc ctgggtgctg ggcggcgcgg tgggcgtgtt ggtgtacacc gagctgtggg    960
tgggcttcac tgcggtgagc gcgctgctga tcctgggtct ggctcagacc atcgtcagct   1020
tccgcggcga ttcgctgatc cctggcctgg gcggtaatcg gcccgtgatg gccgagcaag   1080
aaaccacccg tcgtggtgcg gcggtggcgc cgnagtgaag cgcggtgtcg caacgctgcc   1140
ggtgatcctg gtgattctgc tctcggtggc ggccggggcc ggtgcatggc tgctagtacg   1200
cggacacggt ccgcagcaac ccagatcag cgcttactcg cacgggcacc tgacccgcgt   1260
ggggccctat ttgtactgca acgtggtcga cctcgacgac tgtcagaccc cgcangcgca   1320
gggcgaattg ccggtaagcg aacgctatcc cgtgcagctc tcggtacccg aagtcatttc   1380
ccgggcgccg tggcgtttgc tgcaggtata ccaggacccc gccaacacca ccagcacctt   1440
gtttcggccg gacacccggt tggcggtcac catccccact gtcgacccgc agcgcgggcg   1500
gctgaccggg attgtcgtgc agttgctgac gttggtggtc gaccactcgg gtgaactacg   1560
cgacgntccg cacgcggaat ggtcggtgcg ccttatcttt tgacgaggcc gcggctcgac   1620
gggacgctta agcgcggtcg gcgccaacgg tccgaagagc cgccgacacc cggggcacat   1680
cggcgcatca tggaactgtg cggatcggag tcggggtttg caccacgccc gacgcgcggc   1740
aggccgcggt ggaggctgcg ggccaggcgc gcgacgagct ggcgggtgag cgccgtcgc    1800
tggcggtgtt gcttggatcg cgtgcacaca ccgaccgggc tgccgacgtc ctgagcgcgg   1860
tgctgcagat gatcgayccg cccgcgcttg tcggttgcat cgcccaggcc atcgtcgccg   1920
gccgccacga gatcgaggac gagcccgcgg tggtggtgtg gctggcgtcc ggcttggccg   1980
ccgagacatt ccagctggac tttgtccgta ccggctcggg tgccctgatc accggttatc   2040
ggttcgaccg caccgcccgg gatctgcatc tgctgctgcc ggacccgtac acattcccgt   2100
cgaacctgct catcgagcac cccaacaccg acctgccggg caccgccgtc gtgggcggcg   2160
ntggtgagcg gcgggcgccg gcggggcgac acccggctgt tccgcgatca cgacgtgctc   2220
acctccggcg tcgtcggcgt gcgcctgccc gggatgcgcg gtgtmccggt cgtgtcgcag   2280
ggttgccggc cgatcggcta cccatacatc gtcaccggcg cggacggcat actgatcacc   2340
gagctcgg                                                             2348
```

<210> SEQ ID NO 62
<211> LENGTH: 821

```
<212> TYPE: DNA
<213> ORGANISM: Mycobacterium tuberculosis
<220> FEATURE:
<221> NAME/KEY: variation
<222> LOCATION: (1)..(821)
<223> OTHER INFORMATION: n = A, C, G, or T
<400> SEQUENCE: 62
cgttacccgc tttacaccac cgccaaggcc aacctgaccg cgctcagcac cgggctgtcc      60
agctgtgcga tggccgacga cgtgctggcc gagcccgacc ccaatgccgg catgctgcaa     120
ccggttccgg gccaggcgtt cggaccggac ggacgctggg cggtatcagt cccgtcggct     180
tcaaacccga gggcgtgggc gaggacctca agtccgancc cggtggtctc caaacccggg     240
ctggtcaact ccgatgcgtc gcccaacaaa cccaacgccg ccatcaccga ctccgcgggc     300
accgccggag ggaagggccc ggntcgggat ncaacgggtt gcnacgcggc gctgccgttc     360
nggattggac ccggcacgta ccccggtgat gggcagctac gggagaaaca acctggccgc     420
cacggccacc tcggcctggt accagttacc gccccgcagc ccggaccggc cgctggtggt     480
ggtttccgcg gccggcgcca tctggtccta caaggaggac ggcgatttca tctacggcca     540
gtccctgaaa ctgcagtggg gcgtcaccgg cccggacggc cgcatccagc cactggggca     600
ggtatttccg atcgacatcg gaccgcaacc cgcgtggcgc aatctgcggt ttccgctggc     660
ctgggcgccg ccggaggccg acgtggcgcg cattgtcgcc tatgacccga acctgagccc     720
tgagcaatgg ttcgccttca ccccgccccg ggttccggtg ctggaatctc tgcagcggtt     780
gatcgggtca gcgacaccgg tgttgatgga catcgcgacc g                         821

<210> SEQ ID NO 63
<211> LENGTH: 479
<212> TYPE: DNA
<213> ORGANISM: Mycobacterium tuberculosis
<220> FEATURE:
<221> NAME/KEY: variation
<222> LOCATION: (1)..(479)
<223> OTHER INFORMATION: n = A, C, G, or T
<400> SEQUENCE: 63
gccagccgtg atcggctgay cggncagntg atcaccaacc tcaacgtggt gctgggcntc      60
gctggncgct cacacngatc ggttggacca gscggttgacg tcgctatcag cgttgattca    120
ccggctcgcg caacgcaaga ccgacatctc caacgccgtg gcctacacca acgcgccgcc    180
ggctcggtcg ccgatctnct gtcgcaggct cgcgcnncgt tggcgaangt ggttcgcgag    240
accgatcggg tggccggcat cgcggccgcc gaccacgact acctcgacaa tctgctcaac    300
acgctgccgg acaaatacca ggcgctggtc cgccagggta tgtacggcga cttcttcgcc    360
ttctacctgt gcgacgtcgt gctcaaggtc aacggcaagg gcggccagcc ggtgtacatc    420
aagctggccg gtcaggacan gcnggcggtg cgcgccgaaa tgaaatcctt cgccgaacg    479

<210> SEQ ID NO 64
<211> LENGTH: 481
<212> TYPE: DNA
<213> ORGANISM: Mycobacterium tuberculosis
<220> FEATURE:
<221> NAME/KEY: variation
<222> LOCATION: (1)..(481)
<223> OTHER INFORMATION: n = A, C, G, or T
<400> SEQUENCE: 64
kgtctcgcgn ccttaacatc cggtcgcccc ancggtaatc tgcctgtgga tgccgtccgg     60
aantataagc aaatggccag gagtgcgtga cgcagttatg gctcggtata gttccgtttnt   120 tgccccggac tgggggcgtg aggtggaact aatggcggtg tcgggtgata tttccgacgg    180
```

```
caagcgacca tataggtgga tcgacggcaa taaasacacg ctctggccac gtttcttggc      240
ggggaaaggg gtgatgctat cggagccaat ggtatcgcga caacacttgc agatgccgcc      300
aaggccgatc acgctaatga cggattcggg gccacaaacg ttccccgttc tggcggtttt      360
ctctgactac acctcagatc aaggtgtgat tttgatggat cgcgccagtt atcgggccca      420
ttggcaggat gatgacgtga cgaccatgtt tcttttttg gcnatncggg tgcgaatagc       480
g                                                                      481
```

<210> SEQ ID NO 65
<211> LENGTH: 469
<212> TYPE: DNA
<213> ORGANISM: Mycobacterium tuberculosis
<220> FEATURE:
<221> NAME/KEY: variation
<222> LOCATION: (1)..(469)
<223> OTHER INFORMATION: n = A, C, G, or T

<400> SEQUENCE: 65

```
ggcgaggtca gtgaagccga ggaagcggaa aggagcgccc aatacggaac cgcctctccc       60
cgcgcgttgg ccgattcatt aaatgcagct ggcacgacag gtttcccgac tggaamgcgg      120
gcagtgagcg caasgcaatt aatgtgagtt agctcactca ttaggcaccc caggctttac      180
actttatgct tccggctcgt atgttgtgtg gaattgtgag cggataacaa tttcacacag      240
gaaacagcta tgacatgatt acgaatttaa tacgactcac tatagggaat tcgagctcgg      300
tacccgggga tcctctagag tcgcttcggt tggcggcgac cagcagtgga tccacggtgg      360
ccgcccgcgc ggcdtcatac accgccgcgg cctccttggc ctgtgcggcc sgcttagcgc      420
gcgtgttgct gccgtgctta gccanctggc atagggggct gccgcgcgc                  469
```

<210> SEQ ID NO 66
<211> LENGTH: 291
<212> TYPE: DNA
<213> ORGANISM: Mycobacterium tuberculosis
<220> FEATURE:
<221> NAME/KEY: variation
<222> LOCATION: (1)..(291)
<223> OTHER INFORMATION: n = A, C, G, or T

<400> SEQUENCE: 66

```
caggttcgac tgatctagct gnrrrccara ccggcacnag ncgacantta ccantacctg       60
acanacagnc cgntcnagcc aanccgnann naggangcag nagnaacagg cagatgcatc      120
taatgatacc cgcggagtat atctccaacg tgatatatga aggtccgcgt gctgactcat      180
tgtatgccgc cgaccagcga ttgcgacaat tagctgactc agttagaacg actgccgagt      240
cgctcaacac cacgctcgac gagctgcacg agaactggaa aggtagtttc a              291
```

<210> SEQ ID NO 67
<211> LENGTH: 1306
<212> TYPE: DNA
<213> ORGANISM: Mycobacterium tuberculosis

<400> SEQUENCE: 67

```
gtgatacagg aggcgccaac agtgacacct cgcgggccag gtcgtttgca acgcttgtcg       60
cagtgcaggc ctcagcgcgg ctccggaggg cctgcccgtg gtcttcgaca gctggcgctc      120
gcagcaatgc tgggggcatt ggccgtcacc gtcagtggat gcagctggtc ggaagccctg      180
ggcatcggtt ggccggaggg cattacccg gaggcacacc tcaatcgaga actgtggatc      240
ggggcggtga tcgcctccct ggcggttggg gtaatcgtgt gggtctcat cttctggtcc      300
```

```
gcggtatttc accggaagaa gaacaccgac actgagttgc cccgccagtt cggctacaac      360
atgccgctag agctggttct caccgtcata ccgttcctca tcatctcggt gctgttttat      420
ttcaccgtcg tggtgcagga gaagatgctg cagatagcca aggatcccga ggtcgtgatt      480
gatatcacgt ctttccagtg gaattggaag tttggctatc aaaggtgaa cttcaaagac       540 ggcacactga cctatgatgg tgccgatccg gagcgcaagc gcgccatggt ttccaagcca      600
gagggcaagg acaagtacgg cgaagagctg gtcgggccgg tgcgcgggct caacaccgag      660
gaccggacct acctgaattt cgacaaggtc gagacgttgg gcaccagcac cgaaattccg      720
gtgctggtgc tgccgtccgg caagcgtatc gaattccaaa tggcctcagc cgatgtgata      780
cacgcattct gggtgccgga gttcttgttc aagcgtgacg tgatgcctaa cccggtggca      840
aacaactcgg tcaacgtctt ccagatcgaa gaaatcacca agaccggagc attcgtgggc      900
cactgcgccg agatgtgtgg cacgtatcac tcgatgatga acttcgaggt ccgcgtcgtg      960 accccccaacg atttcaaggc ctacctgcag caacgcatcg acgggaakac aaacgccgag     1020
gccctgcggg cgatcaacca gccgccctt gcggtgacca cccacccgtt tgatactcgc       1080
cgcggtgaat tggccccgca gcccgtaggt taggacgctc atgcatatcg aagcccgact      1140
gtttgagttt gtcgccgcgt tcttcgtggt gacggcggtg ctgtacggcg tgttgacctc      1200
gatgttcgcc accggtggtg tcgagtgggc tggcaccact gcgctggcgc ttaccggcgg      1260
catggcgttg atcgtcgcca ccttcttccg gtttgtggcc gcggat                     1306
```

<210> SEQ ID NO 68
<211> LENGTH: 728
<212> TYPE: DNA
<213> ORGANISM: Mycobacterium tuberculosis
<220> FEATURE:
<221> NAME/KEY: variation
<222> LOCATION: (1)..(728)
<223> OTHER INFORMATION: n = A, C, G, or T
<400> SEQUENCE: 68

```
ggtgcctgcc atcggttcgc tggccacgct ggcatctttg gtctgttaga ggtatccgcg       60
cggatggcca gtcctgttgg cggggnttgt cgccacgatt gccgcccgcg ctgaancccg      120
acgacgccga tgccctgccc accacggatc ggctgaccac ccgagcgaac cgtgcagatg      180
cttggttgac gagcctgctg gcgnccttcg cggcctcggc gaccatcggt gccatcggaa      240
ccgccgtcgc aacccacggc atccacagst ccagcatngg cggtatcgcg ttggccgncg      300
tcaccggtgc gctgctgctg ctacgagcac gttcagcaga caccagaagg tcactggtgt      360
ttgccatctg tggaatcacc accgttgcaa cggcattnta ccgtcgccgc ggatcgggct      420
ctggaacacg gccgtggat tgccgcgctg accgccatgc tggnccgccg tggcaatgtt       480
tttgggcttc gtcgctcccg cgttgtcgct ctcgcccgtc acgtaccgca ccatcgaatt      540
gctggagtgt ctggcgctga tcgcaatggt tccattgacc gcttggstat gcggcgccta      600
caggcgcgtt cgccacctcg acctgacatg gacatgacca cngtcccgta ccctgcgcct      660
gctggtggta tcagcgctcg cgacgctgtc tgggttggga acgccggttg cgccacgcgg      720
tttcgccg                                                               728
```

<210> SEQ ID NO 69
<211> LENGTH: 1028
<212> TYPE: DNA
<213> ORGANISM: Mycobacterium tuberculosis
<220> FEATURE:
<221> NAME/KEY: variation
<222> LOCATION: (1)..(1028)
<223> OTHER INFORMATION: n = A, C, G, or T

<400> SEQUENCE: 69

| | | | | |
|---|---|---|---|---|
| gktcncggtg | atgtcgaccg | tcggcacgac | gagcgaaacc | tcaccggtcg acagtgtctg | 60 |
| cccgaggccg | cagccgacgt | gcccccggag | accgcgcgcc | aacacggtgc cgtacatgta | 120 |
| gcccgcacgg | cgcatcatcg | ccgagccggc | gtagatgttt | tcctgcacgg cgtgcgcggt | 180 |
| gaaccentcc | ggcgccagca | ccgccacctt | tcccgcgtcc | acgtcggcct gggtggtgac | 240 |
| gccgagcacc | ccaccgaaat | gatcgacatg | gctgtgggtg | tagatgaccg scgaccacgg | 300 |
| ggcggtcggc | tccgcggtgg | gcgcgataca | agtccagcgc | ggcggcggcc acctcggtgg | 360 |
| acaccaacgg | gtcgatgacg | atcagcccag | tgtcaccctc | aacgaagctg atattggaga | 420 |
| tatcgaatcc | gcggacctga | tagatgcccg | gcaccacctg | gtagaggccc tgtttcgcgg | 480 |
| tcagctggga | ttgccgccac | aggctgggat | gcaccgatgt | cggcgcggca ccgtcgagaa | 540 |
| acgagtacgc | gtcgttgtcc | cacaccacgc | gaccatcggc | agccttgatc acacacgggg | 600 |
| acagcgcggc | aatgaatccg | cgatcggcgt | cgtcgaaatc | cgttgtgtca tgcaacggta | 660 |
| acgagtgttc | accgtgtgcc | gcctggatga | cggcagtngg | gaggtttgtg ttccatcggc | 720 |
| actacattgc | cactactacg | gtgcacgccg | gtagatgcca | ttggcgaacc acgctaccga | 780 |
| ccagaaagag | agaatttttcc | gccgcaccta | gacctcgggc | cctcntaacg cgcatactgc | 840 |
| cgaagcggtc | ctcaatgccg | atggaccgct | acgacaggca | aaggagcaca gggtgaagcg | 900 |
| tggactgacg | gtcgcggtag | ccggagccgc | cattctggtc | gcaggtcttt ccggatgttc | 960 |
| aagcaacaag | tcgactacag | gaagcggtga | gaccacgacc | gcgngcaggc acgacgcaag | 1020 |
| ccccggcg | | | | | 1028 |

<210> SEQ ID NO 70
<211> LENGTH: 780
<212> TYPE: DNA
<213> ORGANISM: Mycobacterium tuberculosis
<220> FEATURE:
<221> NAME/KEY: variation
<222> LOCATION: (1)..(780)
<223> OTHER INFORMATION: n = A, C, G, or T

<400> SEQUENCE: 70

```
agatcaacac catcaccagt gcggtcatcg agttgctgca gggcnagggt ggtccgttgg     60
cgaacgtgct cgccgcyacc ggtgccttct cggcggcgct gggcgcacgc gaccagctga    120
tcggcgaggt aatcaccaac ctcaacgcgg tgctggcgac cgtcgatgca aagagcgcgc    180
aatttntcgg ccagtgtcga ccagctgcag cagctggtca gcggcctggc caagaaccgg    240
gatccgatcg cgggcgccat ttcgccgctg gcgtcgacga cgacggatct tacggaactg    300
ttgcggaatt cgcgcgccgc gctgcaaggc atcctggaaa acgcccggcc gctggctacc    360
gagctggaca accgaaaggc cgaggtcaas aacgacatcg agcagctcgg cgaggactac    420
ctgcgcctgt ccgcgctggg cagttacgga gcattcnttc aacatctact tctgctcggt    480
gacgatcaag atcaacggac cggccggcag cgacatcctg ctgccgatcg gcggccagcc    540
ggatcccagc aaggggaggt gcgcctttgc taaataggaa gccaagtagc aaacacgaac    600
gcgacccgnt ccgcaccggc atcttcggcc tggtgctggt gatctgcgtc gtcctgatcg    660
cattcggcta cagcgggttg cctttctggc cacagggcaa aacctacgac gcgtatttca    720
ccgacgccgg tgggatcacc cccggtaact cggtttatgt ctcgggcctc aaggtgggcg    780
```

<210> SEQ ID NO 71
<211> LENGTH: 689
<212> TYPE: DNA
<213> ORGANISM: Mycobacterium tuberculosis
<220> FEATURE:
<221> NAME/KEY: variation
<222> LOCATION: (1)..(689)
<223> OTHER INFORMATION: n = A, C, G, or T
<400> SEQUENCE: 71

```
ctatccgcaa ggcttcgcag acgctcggct gnaccgcaga atcgcggtgc acccacgatt      60
gccagtagcg cgggcccact cgtgcctact acacttcgtc gtagccaaat catcggcccc     120
gtagtatctc cggagatgac agatgaatgt cgtcgacatt tcgcggtggc agttcggtat     180
caccaccgtc tatcacttca ttttcgtnac cgctgaccat cggcctggcc ccngctgatc     240
gcggtcatgc aaactgctgt nggtcgtcac cgataacccc gcctggtatc gcctcaccaa     300
attcttcggc aaattgttcc tgatcaactt tgccatcggc gtggcgaccg gaatcgtgca     360
ggaatttcag ttcggcatga actggagcga gtactcccga ttcgtcggcg atgtcttcgg     420
cgccccgctg gccatggagg gcctggcggc cttcttcttc gaatccacct tcatcggggtt    480
gtggatcttc ggctggaaca ggctgccccg gctggtgcat ctggcctgca tctggatcgt     540
cgcaatcgcg gtcaacgtgt ccgcgttctt catcatcgng gcaaactcct tcatgcagca     600
tccggtcggc gcgcactaca acccgaccac cgggcgtgcc gagttgagca gcatcgtcgt     660
gcctgctgac caacaacacc gcacaggcg                                        689
```

<210> SEQ ID NO 72
<211> LENGTH: 274
<212> TYPE: DNA
<213> ORGANISM: Mycobacterium tuberculosis
<400> SEQUENCE: 72

```
ccgcagcacc gaggcaagca tcgcacccgt cgattcccgc catcccggcg acatgatggt      60
catgtccgac accgacgccc gcacctcgct tcccgagttg accgcgctgc cgtggacgc      120
cgcaacggat gcgtcggttc attcgatccc ggctcgaaat tggccatggc gaacgcatct    180
tgctgtgatg gttcgggcag tagatctcca ctgccgcact gataaactcg ggtcatggtc    240
gtcgtgaggc ggacagggta gaggcgcatg accg                                 274
```

<210> SEQ ID NO 73
<211> LENGTH: 252
<212> TYPE: DNA
<213> ORGANISM: Mycobacterium tuberculosis

<400> SEQUENCE: 73

```
gtgatgcctt ccagcattgg attggtcgtc ggttcgatgc tgtggcgaca gataaaccgc      60
ctgttcgggg tgcgtggcct ctgctgggca gcgcactgct caacgccgct ctgcgctgct    120
gtgcatggtg gccgagtcgt gtgggcagtg ggttcacgcc tgggcgtact tcacggcgtt    180
cctgctggct acggtggccg ctcaaacggt ggtcgccgca tcgatatcgt ggatcagcgt    240
cctcgcgccc ga                                                          252
```

<210> SEQ ID NO 74
<211> LENGTH: 160
<212> TYPE: DNA
<213> ORGANISM: Mycobacterium tuberculosis

<400> SEQUENCE: 74

```
ggcgccgccg tcgtgctggc cgcccggccc ggtgggggtg ccggccagcg tggttccgcc      60
```

```
agtggccgcg ccgaacgtat tggccggcgt cctcgagcac gacaacgacg ggtcggggc      120 ggcggtgctg gccgcgctgg ccaagctgcc acccggtggt                           160
```

<210> SEQ ID NO 75
<211> LENGTH: 401
<212> TYPE: DNA
<213> ORGANISM: Mycobacterium tuberculosis
<220> FEATURE:
<221> NAME/KEY: variation
<222> LOCATION: (1)..(401)
<223> OTHER INFORMATION: n = A, C, G, or T

<400> SEQUENCE: 75

```
atcagccgcg ggtcgacgcc gccgatgacc tcgacgtcgt cgtcgtcgct gccggtactc      60
aatccaatca ccatcctctt acgcaccttc taggagtgtg ttgctgcggc agtgccgngc     120
cattcgtaga ttcgggcctc gccgttgtcg tagatcttcg cccacgacct cgatgtctct    180
aacgacacta gtccgtccgg cacngcaaan ccccgcaccg tcggagtgct ggtcaggnta    240
tagncggtac aggnggactt ggwwggcctc gagtanccga ggwwcgntct ncccgttgcg    300
gncataggcc agaagatgaa ccggtgtaga ccgggcctgt tgcgagggtc gtagtcgtag    360
gtcccagagg tgtcggacgc ccaggttaat acacagcgtg c                        401
```

<210> SEQ ID NO 76
<211> LENGTH: 248
<212> TYPE: DNA
<213> ORGANISM: Mycobacterium tuberculosis

<400> SEQUENCE: 76

```
gcagacctct ggccgctggt ggtgctgggt acctgcgctg gcgacaccgg accgcagacc      60
gtcaatcggg actcccggga acgtggtgcc atcttgccac ggggatggcc gacgcggctc     120
gtcattctcc ccgagcgcac cggccgccgc tgttgaccgg gccgcggcga ctgatggtgc     180
ccgcacacgc gggcgggttc aaggagcaat acgccaagtc cagcgccgct ctcgcacggc    240
gcggtgtt                                                              248
```

<210> SEQ ID NO 77
<211> LENGTH: 17
<212> TYPE: PRT
<213> ORGANISM: Mycobacterium tuberculosis

<400> SEQUENCE: 77

Val His Leu Ala Thr Gly Met Ala Glu Thr Val Ala Ser Phe Ser Pro
 1               5                  10                  15
Ser

<210> SEQ ID NO 78
<211> LENGTH: 17
<212> TYPE: PRT
<213> ORGANISM: Mycobacterium tuberculosis

<400> SEQUENCE: 78

Arg Glu Val Val His Leu Ala Thr Gly Met Ala Glu Thr Val Ala Ser
 1               5                  10                  15
Phe

<210> SEQ ID NO 79
<211> LENGTH: 17
<212> TYPE: PRT

```
<213> ORGANISM: Mycobacterium tuberculosis

<400> SEQUENCE: 79

Arg Asp Ser Arg Glu Val Val His Leu Ala Thr Gly Met Ala Glu Thr
  1               5                  10                  15
Val

<210> SEQ ID NO 80
<211> LENGTH: 17
<212> TYPE: PRT
<213> ORGANISM: Mycobacterium tuberculosis

<400> SEQUENCE: 80

Asp Phe Asn Arg Asp Ser Arg Glu Val Val His Leu Ala Thr Gly Met
  1               5                  10                  15
Ala

<210> SEQ ID NO 81
<211> LENGTH: 17
<212> TYPE: PRT
<213> ORGANISM: Mycobacterium tuberculosis

<400> SEQUENCE: 81

Ile Ser Ala Ala Val Val Thr Gly Tyr Leu Arg Trp Thr Thr Pro Asp
  1               5                  10                  15
Arg

<210> SEQ ID NO 82
<211> LENGTH: 17
<212> TYPE: PRT
<213> ORGANISM: Mycobacterium tuberculosis

<400> SEQUENCE: 82

Ala Val Val Phe Leu Cys Ala Ala Ala Ile Ser Ala Ala Val Val Thr
  1               5                  10                  15
Gly

<210> SEQ ID NO 83
<211> LENGTH: 17
<212> TYPE: PRT
<213> ORGANISM: Mycobacterium tuberculosis

<400> SEQUENCE: 83

Val Thr Asp Asn Pro Ala Trp Tyr Arg Leu Thr Lys Phe Phe Gly Lys
  1               5                  10                  15
Leu

<210> SEQ ID NO 84
<211> LENGTH: 17
<212> TYPE: PRT
<213> ORGANISM: Mycobacterium tuberculosis

<400> SEQUENCE: 84

Ala Trp Tyr Arg Leu Thr Lys Phe Phe Gly Lys Leu Phe Leu Ile Asn
  1               5                  10                  15
Phe

<210> SEQ ID NO 85
<211> LENGTH: 17
<212> TYPE: PRT
<213> ORGANISM: Mycobacterium tuberculosis
```

<400> SEQUENCE: 85

Lys Phe Phe Gly Lys Leu Phe Leu Ile Asn Phe Ala Ile Gly Val Ala
 1               5                  10                  15
Thr

<210> SEQ ID NO 86
<211> LENGTH: 17
<212> TYPE: PRT
<213> ORGANISM: Mycobacterium tuberculosis

<400> SEQUENCE: 86

Phe Leu Ile Asn Phe Ala Ile Gly Val Ala Thr Gly Ile Val Gln Glu
 1               5                  10                  15
Phe

<210> SEQ ID NO 87
<211> LENGTH: 17
<212> TYPE: PRT
<213> ORGANISM: Mycobacterium tuberculosis

<400> SEQUENCE: 87

Ala Ile Gly Val Ala Thr Gly Ile Val Gln Glu Phe Gln Phe Gly Met
 1               5                  10                  15
Asn

<210> SEQ ID NO 88
<211> LENGTH: 17
<212> TYPE: PRT
<213> ORGANISM: Mycobacterium tuberculosis

<400> SEQUENCE: 88

Thr Gly Ile Val Gln Glu Phe Glu Phe Gly Met Asn Trp Ser Glu Tyr
 1               5                  10                  15
Ser

<210> SEQ ID NO 89
<211> LENGTH: 17
<212> TYPE: PRT
<213> ORGANISM: Mycobacterium tuberculosis

<400> SEQUENCE: 89

Glu Phe Gln Phe Gly Met Asn Trp Ser Glu Tyr Ser Arg Phe Val Gly
 1               5                  10                  15
Asp

<210> SEQ ID NO 90
<211> LENGTH: 17
<212> TYPE: PRT
<213> ORGANISM: Mycobacterium tuberculosis

<400> SEQUENCE: 90

Met Asn Trp Ser Glu Tyr Ser Arg Phe Val Gly Asp Val Phe Gly Ala
 1               5                  10                  15
Pro

<210> SEQ ID NO 91
<211> LENGTH: 17
<212> TYPE: PRT
<213> ORGANISM: Mycobacterium tuberculosis

```
<400> SEQUENCE: 91

Trp Ser Glu Tyr Ser Arg Phe Val Gly Asp Val Phe Gly Ala Pro Leu
 1               5                  10                  15
Ala

<210> SEQ ID NO 92
<211> LENGTH: 17
<212> TYPE: PRT
<213> ORGANISM: Mycobacterium tuberculosis

<400> SEQUENCE: 92

Glu Tyr Ser Arg Phe Val Gly Asp Val Phe Gly Ala Pro Leu Ala Met
 1               5                  10                  15
Glu

<210> SEQ ID NO 93
<211> LENGTH: 17
<212> TYPE: PRT
<213> ORGANISM: Mycobacterium tuberculosis

<400> SEQUENCE: 93

Ser Arg Phe Val Gly Asp Val Phe Gly Ala Pro Leu Ala Met Glu Ser
 1               5                  10                  15
Leu

<210> SEQ ID NO 94
<211> LENGTH: 17
<212> TYPE: PRT
<213> ORGANISM: Mycobacterium tuberculosis

<400> SEQUENCE: 94

Trp Ile Phe Gly Trp Asn Arg Leu Pro Arg Leu Val His Leu Ala Cys
 1               5                  10                  15
Ile

<210> SEQ ID NO 95
<211> LENGTH: 17
<212> TYPE: PRT
<213> ORGANISM: Mycobacterium tuberculosis

<400> SEQUENCE: 95

Trp Asn Arg Leu Pro Arg Leu Val His Leu Ala Cys Ile Trp Ile Val
 1               5                  10                  15
Ala

<210> SEQ ID NO 96
<211> LENGTH: 17
<212> TYPE: PRT
<213> ORGANISM: Mycobacterium tuberculosis

<400> SEQUENCE: 96

Gly Arg Ala Glu Leu Ser Ser Ile Val Val Leu Leu Thr Asn Asn Thr
 1               5                  10                  15
Ala

<210> SEQ ID NO 97
<211> LENGTH: 17
<212> TYPE: PRT
<213> ORGANISM: Mycobacterium tuberculosis

<400> SEQUENCE: 97
```

```
Gly Lys Thr Tyr Asp Ala Tyr Phe Thr Asp Ala Gly Gly Ile Thr Pro
 1               5                  10                  15
Gly
```

<210> SEQ ID NO 98
<211> LENGTH: 17
<212> TYPE: PRT
<213> ORGANISM: Mycobacterium tuberculosis

<400> SEQUENCE: 98

```
Tyr Asp Ala Tyr Phe Thr Asp Ala Gly Gly Ile Thr Pro Gly Asn Ser
 1               5                  10                  15
Val
```

<210> SEQ ID NO 99
<211> LENGTH: 17
<212> TYPE: PRT
<213> ORGANISM: Mycobacterium tuberculosis

<400> SEQUENCE: 99

```
Trp Pro Gln Gly Lys Thr Tyr Asp Ala Tyr Phe Thr Asp Ala Gly Gly
 1               5                  10                  15
Ile
```

<210> SEQ ID NO 100
<211> LENGTH: 17
<212> TYPE: PRT
<213> ORGANISM: Mycobacterium tuberculosis

<400> SEQUENCE: 100

```
Ala Thr Gly Met Ala Glu Thr Val Ala Ser Phe Ser Pro Ser Glu Gly
 1               5                  10                  15
Ser
```

<210> SEQ ID NO 101
<211> LENGTH: 17
<212> TYPE: PRT
<213> ORGANISM: Mycobacterium tuberculosis

<400> SEQUENCE: 101

```
Gly Trp Glu Arg Arg Leu Arg His Ala Val Ser Pro Lys Asp Pro Ala
 1               5                  10                  15
Gln
```

<210> SEQ ID NO 102
<211> LENGTH: 17
<212> TYPE: PRT
<213> ORGANISM: Mycobacterium tuberculosis

<400> SEQUENCE: 102

```
Thr Gly Ser Gly Glu Thr Thr Thr Ala Ala Gly Thr Thr Ala Ser Pro
 1               5                  10                  15
Gly
```

<210> SEQ ID NO 103
<211> LENGTH: 17
<212> TYPE: PRT
<213> ORGANISM: Mycobacterium tuberculosis

<400> SEQUENCE: 103

```
Gly Ala Ala Ile Leu Val Ala Gly Leu Ser Gly Cys Ser Ser Asn Lys
 1               5                  10                  15

Ser
```

<210> SEQ ID NO 104
<211> LENGTH: 17
<212> TYPE: PRT
<213> ORGANISM: Mycobacterium tuberculosis

<400> SEQUENCE: 104

```
Ala Val Ala Gly Ala Ala Ile Leu Val Ala Gly Leu Ser Gly Cys Ser
 1               5                  10                  15

Ser
```

<210> SEQ ID NO 105
<211> LENGTH: 17
<212> TYPE: PRT
<213> ORGANISM: Mycobacterium tuberculosis

<400> SEQUENCE: 105

```
Leu Thr Val Ala Val Ala Gly Ala Ala Ile Leu Val Ala Gly Leu Ser
 1               5                  10                  15

Gly
```

<210> SEQ ID NO 106
<211> LENGTH: 21
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 106
cccagcttgt gatacaggag g                                          21

<210> SEQ ID NO 107
<211> LENGTH: 22
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 107
ggcctcagcg cggctccgga gg                                         22

<210> SEQ ID NO 108
<211> LENGTH: 46
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 108
tctagacacc accaccacca ccacgtgaca cctcgcgggc caggtc               46

<210> SEQ ID NO 109
<211> LENGTH: 28
<212> TYPE: DNA
<213> ORGANISM: Mycobacterium tuberculosis
<220> FEATURE:
<223> OTHER INFORMATION: Description of Artificial Sequence:PCR Primer

<400> SEQUENCE: 109
aagcttcgcc atgccgccgg taagcgcc                                   28

<210> SEQ ID NO 110
<211> LENGTH: 330
<212> TYPE: DNA
<213> ORGANISM: Mycobacterium tuberculosis
<220> FEATURE:
<221> NAME/KEY: variation
<222> LOCATION: (1)..(330)
<223> OTHER INFORMATION: n = A, C, G, or T

<400> SEQUENCE: 110

| | | | | | |
|---|---|---|---|---|---|
| gcacgtcgtc | gccagtgcca | accagggccc | ggggcnnacc | agctcgccga | tccacggcaa | 60 |
| caacgagacg | tagaacacca | ggccgaatag | caggccgtag | cccagcccac | ccaccggtgt | 120 |
| cgtcgcgcgg | tgggtcagca | cccaggccag | caatgcgnag | cccaaccacc | gccgnccacc | 180 |
| agcagttgcg | cggcgggaag | ctggcataca | acagcagacc | ggccacgatg | ctgaccacca | 240 |
| ggcgcgtcan | ccgcgtccgc | accgngtccc | gtgtggtggg | cagctgcgct | ncacccakkc | 300 |
| kccaagcttc | accanggcgc | cgscgggccg | | | | 330 |

<210> SEQ ID NO 111
<211> LENGTH: 431
<212> TYPE: DNA
<213> ORGANISM: Mycobacterium tuberculosis
<220> FEATURE:
<221> NAME/KEY: variation
<222> LOCATION: (1)..(431)
<223> OTHER INFORMATION: n = A, C, G, or T

<400> SEQUENCE: 111

| | | | | | |
|---|---|---|---|---|---|
| tgtcccgcat | ggtagtcggg | ctggnccngg | tgatcgcttg | cagctttngc | cgtggatgtg | 60 |
| agaaaggaat | atgttggtga | tcaccatgtt | tcgtgtactc | gtggcgcgga | tgacggcgct | 120 |
| ggcggtcgac | gangtcgggc | atgtccaccg | tggaatacgc | catcggtacc | atcgcggcgg | 180 |
| ctgcnttcgg | tgcgatcctc | tacacggtcg | tcaccgggga | ttccattgtg | tcggcgctca | 240 |
| accgcatcat | cggtcgcgcg | ctcagcacca | aggtttagcg | tcgtgtgcgg | gtgcgagcac | 300 |
| cgtggaagcg | gcgttggcga | tcgccaccct | ggtgctggtg | ctggtgctgt | gcctggcggg | 360 |
| cgtcaccgcg | gtatcaatgc | aggtgcgctg | tatcgacgcg | gcccgcgagg | ccgctcgatt | 420 |
| ggccgcgcgc | g | | | | | 431 |

<210> SEQ ID NO 112
<211> LENGTH: 143
<212> TYPE: PRT
<213> ORGANISM: Mycobacterium tuberculosis

<400> SEQUENCE: 112

Ala Gly Gly Cys Gly Ala Cys Gly Gly Thr Gly Gly Cys Ala Cys
 1               5                  10                  15

Cys Ala Cys Cys Ala Cys Gly Ala Gly Thr Gly Ala Gly Thr Cys Ala
                20                  25                  30

Gly Gly Cys Ala Gly Gly Ala Gly Cys Cys Cys Gly Cys Cys Ala
                35                  40                  45

Cys Gly Thr Thr Gly Cys Gly Gly Ala Cys Gly Gly Cys Gly Cys Gly
            50                  55                  60

Ala Ala Thr Cys Thr Thr Cys Gly Cys Cys Thr Gly Thr Gly Gly Cys
65                  70                  75                  80

Thr Cys Ala Cys Cys Gly Ala Cys Thr Thr Thr Cys Cys Gly Cys Cys
                85                  90                  95

Cys Ala Ala Cys Thr Thr Cys Ala Ala Cys Gly Ala Thr Cys Thr Thr

```
              100                 105                 110
Gly Cys Ala Cys Ala Thr Gly Ala Cys Gly Cys Ala Ala Gly
            115                 120                 125

Ala Ala Cys Gly Cys Cys Gly Ala Gly Gly Thr Cys Gly Cys Gly
        130                 135                 140
```

<210> SEQ ID NO 113
<211> LENGTH: 363
<212> TYPE: PRT
<213> ORGANISM: Mycobacterium tuberculosis

<400> SEQUENCE: 113

```
Met Thr Pro Arg Gly Pro Gly Arg Leu Gln Arg Leu Ser Gln Cys Arg
  1               5                  10                  15

Pro Gln Arg Gly Ser Gly Gly Pro Ala Arg Gly Leu Arg Gln Leu Ala
             20                  25                  30

Leu Ala Ala Met Leu Gly Ala Leu Ala Val Thr Val Ser Gly Cys Ser
         35                  40                  45

Trp Ser Glu Ala Leu Gly Ile Gly Trp Pro Glu Gly Ile Thr Pro Glu
     50                  55                  60

Ala His Leu Asn Arg Glu Leu Trp Ile Gly Ala Val Ile Ala Ser Leu
 65                  70                  75                  80

Ala Val Gly Val Ile Val Trp Gly Leu Ile Phe Trp Ser Ala Val Phe
                 85                  90                  95

His Arg Lys Lys Asn Thr Asp Thr Glu Leu Pro Arg Gln Phe Gly Tyr
            100                 105                 110

Asn Met Pro Leu Glu Leu Val Leu Thr Val Ile Pro Phe Leu Ile Ile
        115                 120                 125

Ser Val Leu Phe Tyr Phe Thr Val Val Gln Glu Lys Met Leu Gln
    130                 135                 140

Ile Ala Lys Asp Pro Glu Val Val Ile Asp Thr Ser Phe Gln Trp
145                 150                 155                 160

Asn Trp Lys Phe Gly Tyr Gln Arg Val Asn Phe Lys Asp Gly Thr Leu
            165                 170                 175

Thr Tyr Asp Gly Ala Asp Pro Glu Arg Lys Arg Ala Met Val Ser Lys
        180                 185                 190

Pro Glu Gly Lys Asp Lys Tyr Gly Glu Glu Leu Val Gly Pro Val Arg
    195                 200                 205

Gly Leu Asn Thr Glu Asp Arg Thr Tyr Leu Asn Phe Asp Lys Val Glu
    210                 215                 220

Thr Leu Gly Thr Ser Thr Glu Ile Pro Val Leu Val Leu Pro Ser Gly
225                 230                 235                 240

Lys Arg Ile Glu Phe Gln Met Ala Ser Ala Asp Val Ile His Ala Phe
            245                 250                 255

Trp Val Pro Glu Phe Leu Phe Lys Arg Asp Val Met Pro Asn Pro Val
        260                 265                 270

Ala Asn Asn Ser Val Asn Val Phe Gln Ile Glu Glu Ile Thr Lys Thr
    275                 280                 285

Gly Ala Phe Val Gly His Cys Ala Glu Met Cys Gly Thr Tyr His Ser
    290                 295                 300

Met Met Asn Phe Glu Val Arg Val Val Thr Pro Asn Asp Phe Lys Ala
305                 310                 315                 320

Tyr Leu Gln Gln Arg Ile Asp Gly Asn Thr Asn Ala Glu Ala Leu Arg
            325                 330                 335
```

Ala Ile Asn Gln Pro Pro Leu Ala Val Thr Thr His Pro Phe Asp Thr
        340                 345                 350

Arg Arg Gly Glu Leu Ala Pro Gln Pro Val Gly
        355                 360

<210> SEQ ID NO 114
<211> LENGTH: 709
<212> TYPE: DNA
<213> ORGANISM: Mycobacterium tuberculosis

<400> SEQUENCE: 114

| | | | | | |
|---|---|---|---|---|---|
| ggatccgcgg | agtatatctc | caacgtaata | tatgaaggtc | cgcgtgctga | ctcattgtat | 60 |
| gccgccgacc | agcgattgcg | acaattagct | gactcagtta | gaacgactgc | cgagtcgctc | 120 |
| aacaccacgc | tcgacgagct | gcacgagaac | tggaaaggta | gttcatcgga | atggatggcc | 180 |
| gacgcggctt | tgcggtatct | cgactggctg | tctaaacact | cccgtcagat | tttgcgaacc | 240 |
| gcccgcgtga | tcgaatccct | cgtaatggcc | tatgaggaga | cacttctgag | ggtggtaccc | 300 |
| ccggcgacta | tcgccaacaa | ccgcgaggag | gtgcgcaggc | tgatcgcgag | caacgtggcc | 360 |
| gggggtaaac | actccagcaa | tcgcagacct | cgaggcacaa | tacgagcagt | accgggccga | 420 |
| aaatatccaa | gcaatggacc | gctatctaag | ttggacccga | tttgcgctat | cgaagctgcc | 480 |
| ccgatggcgg | gagccgccgc | agatccacag | gagcgggtag | gtccaagagg | ccggcgcggt | 540 |
| cttgcaggcc | agcaacaatg | ccgcggtcga | ccaggcccat | cgcttcgctg | ctcgcacgac | 600 |
| acaccgcggt | ttcagatgaa | tcaggcgttt | cacaccatgt | gaacatgtt | gctgacgtgt | 660 |
| tttgcatgtc | aggagaaacc | gagatgacga | tcaacaacca | ggtaagctt | | 709 |

<210> SEQ ID NO 115
<211> LENGTH: 1831
<212> TYPE: DNA
<213> ORGANISM: Mycobacterium tuberculosis

<400> SEQUENCE: 115

| | | | | | |
|---|---|---|---|---|---|
| ggatccccgg | ctaccatgcc | ttcgtcgcgc | aacctcgcga | ccaacccga | gatcgccacc | 60 |
| ggctaccgcc | gggacatgac | cgtggtgcgg | accgcccact | atgcggcagc | caccgccaat | 120 |
| ccgctggcca | ctcaggtggc | ctgccgagta | ttgcgcgacg | tggtaccgc | cgccgatgcc | 180 |
| gtcgtggccg | cccaggcggt | gctggggttg | gtcgaaccgc | aatcctccgg | gatcggcggc | 240 |
| ggcggatatc | tggtgtactt | cgacgcccgc | acgggctcag | tgcaggccta | cgacggccgt | 300 |
| gaggtggccc | cagcggccgc | caccgagaac | taccttcgct | gggtcagcga | cgtcgaccgc | 360 |
| agcgcgccca | ggcccaacgc | ccgagcctcg | ggacggtcga | tcggagtacc | gggcatcctg | 420 |
| cgaatgctgg | agatggtgca | caacgagcac | gggcgcacac | cctggcgcga | cctcttcggc | 480 |
| cccgcggtaa | cgctggccga | tggcggtttt | gacatcagcg | ccaggatggg | cgcggccatc | 540 |
| tccgacgctg | cgccgcaact | gcgagacgac | ccggaggctc | gcaagtattt | cctcaatccc | 600 |
| gacggcagcc | cgaaacccgc | gggaacccgg | ctgacgaacc | ccgcgtactc | aaaaaccctg | 660 |
| tccgccatcg | cctccgccgg | cgccaacgcc | ttctattccg | gcgacattgc | ccacgacatc | 720 |
| gtggcggcgg | cgagcgacac | atcgaatggc | cgcacgccgg | gcctgttgac | cattgaggac | 780 |
| ctggcgggtt | acctcgccaa | gagacgccaa | ccgttgtgca | cgacctatcg | cggccgggag | 840 |
| atctgcggca | tgccatcgtc | gggtggcgtc | gccgtggccg | caaccttggg | catcctcgag | 900 |
| cacttcccga | tgagcgacta | cgcgcccagc | aaggtcgacc | tcaacggcgg | tcgcccgacc | 960 |
| gtgatggggg | ttcacctgat | agcggaggcc | gaacggctgg | cctatgccga | ccgcgaccaa | 1020 |

-continued

```
tatatcgctg acgtcgattt tgtccggctg cccggcggct cgctcaccac gctggttgac    1080
ccgggctact tggcagcacg cgccgcgcta atctcgccgc aacacagcat gggcagcgcc    1140
agaccggggg acttcggcgc accgacggcc gtcgcccgc cagtgcctga gcatggcacc     1200
agccacctca gcgtcgtcga ttcgtacggc aatgcggcca cgttgacgac gacggtggaa    1260
tcttcgttcg gctcctacca cctggtgac ggattcatcc tcaacaacca gctgagcgat     1320
ttcagcgccg agccacacgc tactgacgga tcaccggtgg ctaaccgggt cgagcctggg    1380
aagcgaccgc gcagttcgat ggcaccgacg ttggtgttcg atcactcgtc ggcggggcgc    1440
ggtgcgctgt acgcggtgct cggttctccg ggcggctcca tgatcatcca gttcgtcgtg    1500
aaaacacttg tggcgatgct ggattgggt ctgaatccgc agcaggcggt ttccctggtc     1560
gatttcggcg ccgcgaactc gccgcacact aacctcggcg gtgagaatcc cgagatcaac    1620
acttccgacg atggtgatca tgacccgctg gtgcaaggcc tgcgcgcgct ggggcatcga    1680
gttaatcttg ccgagcaatc cagtgggctc tcggcgatca cccgcagcga ggcgggttgg    1740
gccggcggcg ccgacccacg ccgcgaaggc cggtcatgg gcgacgatgc ctgagccgtt     1800
cgccggcggg cggccaaacg aacgcggatc c                                   1831
```

<210> SEQ ID NO 116
<211> LENGTH: 516
<212> TYPE: DNA
<213> ORGANISM: Mycobacterium tuberculosis

<400> SEQUENCE: 116

```
gaattcaagc gcggtgtcgc aacgctgccg gtgatcctgg tgattctgct ctcggtggcg     60
gccggggccg gtgcatggct gctagtacgc ggacacggtc cgcagcaacc cgagatcagc    120
gcttactcgc acgggcacct gacccgcgtg gggccctatt tgtactgcaa cgtggtcgac    180
ctcgacgact gtcagacccc gcaggcgcag ggcgaattgc cggtaagcga acgctatccc    240
gtgcagctct cggtacccga agtcatttcc cgggcgccgt ggcgtttgct gcaggtatac    300
caggaccccg ccaacaccac cagcaccttg tttcggccgg acacccggtt ggcggtcacc    360
atccccactg tcgacccgca gcgcgggcgg ctgaccggga ttgtcgtgca gttgctgacg    420
ttggtggtcg accactcggg tgaactacgc gacgttccgc acgcggaatg gtcggtgcgc    480
cttatctttt gacgaggccg cggctcgacg aagctt                              516
```

<210> SEQ ID NO 117
<211> LENGTH: 2831
<212> TYPE: DNA
<213> ORGANISM: Mycobacterium tuberculosis

<400> SEQUENCE: 117

```
gaattcgcgc cgatgctgga cgcggcggcc gcttgggatg gactggccga cgaattgggt     60
tcggccgcgg cctcgttttc ggcggtgacg gcggggctgg caggttcctc gtggctgggc    120
gcggcgtcga cggcgatgac gggagcggcc gcccccatc tgggctggtt gagcgcggcg     180
gcggcgcagg cccagcaggc ggccacccaa accggctgg cggcggccgc cttcgaggca     240 gccctggcg cgacgtaca tccggcgatc atctcggcca accgggcact gttcgtgtcg     300
ctggtggtct cgaacctgct gggccaaaac gccccggcga tcgcggccac cgaggccgcc    360
tacgagcaga tgtgggccca ggacgtgcg gcgatgtttg gctaccatgc cggggcttcg    420
gcggccgtct cggcgttgac accgttcggc caggcgctgc cgaccgtggc gggcggcggt    480
```

-continued

```
gcgctggtca gcgcggccgc ggctcaggtg accacgcggg tcttccgcaa cctgggcttg    540
gcgaacgtcg gcgagggcaa cgtcggcaac ggtaatgtcg ggaacttcaa tctcggctcg    600
gccaacatcg gcaacggcaa catcggcagc ggcaacatcg gcagctccaa catcgggttt    660
ggcaacgtgg gtcctgggtt gaccgcagcg ctgaacaaca tcggtttcgg caacaccggc    720
agcaacaaca tcgggtttgg caacaccggc agcaacaaca tcggcttcgg caataccgga    780
gacggcaacc gaggtatcgg gctcacgggt agcggtttgt tggggttcgg cggcctgaac    840
tcgggcaccg gcaacatcgg tctgttcaac tcgggcaccg gaaacgtcgg catcggcaac    900
tcgggtaccg ggaactgggg cattggcaac tcgggcaaca gctacaacac cggttttggc    960
aactccggcg acgccaacac gggcttcttc aactccggaa tagccaacac cggcgtcggc   1020
aacgccggca actacaacac cggtagctac aacccgggca acagcaatac cggcggcttc   1080
aacatgggcc agtacaacac gggctacctg aacagcggca actacaacac cggcttggca   1140
aactccggca atgtcaacac cggcgccttc attactggca acttcaacaa cggcttcttg   1200
tggcgcggcg accaccaagg cctgattttc gggagcccg gcttcttcaa ctcgaccagt    1260
gcgccgtcgt cgggattctt caacagcggt gccggtagcg cgtccggctt cctgaactcc   1320
ggtgccaaca attctggctt cttcaactct tcgtcggggg ccatcggtaa ctccggcctg   1380
gcaaacgcgg gcgtgctggt atcgggcgtg atcaactcgg gcaacaccgt atcgggtttg   1440
ttcaacatga gcctggtggc catcacaacg ccggccttga tctcgggctt cttcaacacc   1500
ggaagcaaca tgtcgggatt tttcggtggc ccaccggtct tcaatctcgg cctggcaaac   1560
cggggcgtcg tgaacattct cggcaacgcc aacatcggca attacaacat tctcggcagc   1620
ggaaacgtcg gtgacttcaa catccttggc agcggcaacc tcggcagcca aaacatcttg   1680
ggcagcggca acgtcggcag cttcaatatc ggcagtggaa acatcggagt attcaatgtc   1740
ggttccggaa gcctgggaaa ctacaacatc ggatccggaa acctcgggat ctacaacatc   1800
ggttttggaa acgtcggcga ctacaacgtc ggcttcggga acgcgggcga cttcaaccaa   1860
ggctttgcca caccggcaa caacaacatc gggttcgcca caccggcaa caacaacatc    1920
ggcatcgggc tgtccggcga caaccagcag ggcttcaata ttgctagcgg ctggaactcg   1980
ggcaccggca acagcggcct gttcaattcg ggcaccaata acgttggcat cttcaacgcg   2040
ggcaccggaa acgtcggcat cgcaaactcg ggcaccggga actgggtat cgggaacccg    2100
ggtaccgaca ataccggcat cctcaatgct ggcagctaca acacgggcat cctcaacgcc   2160
ggcgacttca acacgggctt ctacaacacg ggcagctaca acaccggcgg cttcaacgtc   2220
ggtaacacca acaccggcaa cttcaacgtg ggtgacacca ataccggcag ctataacccg   2280
ggtgacacca acaccggctt cttcaatccc ggcaacgtca ataccggcgc tttcgacacg   2340
ggcgacttca acaatggctt cttggtggcg ggcgataacc agggccagat tgccatcgat   2400
ctctcggtca ccactccatt catccccata aacgagcaga tggtcattga cgtacacaac   2460
gtaatgacct cgcggcaa catgatcacg gtcaccgagg cctcgaccgt tttcccccaa    2520
accttctatc tgagcggttt gttcttcttc ggcccggtca atctcagcgc atccacgctg   2580
accgttccga cgatcaccct caccatcggc ggaccgacgg tgaccgtccc catcagcatt   2640
gtcggtgctc tggagagccg cacgattacc ttcctcaaga tcgatccggc gccgggcatc   2700
ggaaattcga ccaccaaccc ctcgtccggc ttcttcaact cgggcaccgg tggcacatct   2760
ggcttccaaa acgtcggcgg cggcagttca ggcgtctgga acagtggttt gagcagcaag   2820
cttgggaatt c                                                       2831
```

<210> SEQ ID NO 118
<211> LENGTH: 1823
<212> TYPE: DNA
<213> ORGANISM: Mycobacterium tuberculosis

<400> SEQUENCE: 118

| | | | | | |
|---|---|---|---|---|---|
| gaattcgctg | accgtggcca | gcgacgaggc | tgcgccccgg | gcatcgcgtc | tgcgctcagg | 60 |
| gcgtcgtttc | aggggaaatc | cagaccctgg | acgcagactc | gatattgggc | tttcgcgtta | 120 |
| ttaacaccgc | tcgtcgtggc | tatggtgctc | accggatgct | cggcctccgg | tacccaactc | 180 |
| gaactcgcgc | ccactgcgga | ccgcagggcc | gcggttggca | ccaccagcga | catcaatcag | 240 |
| caggatcccg | ccacgttgca | agacggcggc | aatcttcgcc | tgtcgctcac | cgactttccg | 300 |
| cccaacttca | acatcttgca | catcgacggc | aacaacgccg | aggtcgcggc | gatgatgaaa | 360 |
| gccaccttgc | cgcgcgcgtt | catcatcgga | ccggacggct | cgacgacggt | cgacaccaac | 420 |
| tacttcacca | gcatcgagct | gaccaggacc | gccccgcagg | tggtcaccta | caccatcaat | 480 |
| cccgaggcgg | tgtggtccga | cgggaccccg | atcacctggc | gggacatcgc | cagccagatt | 540 |
| catgcgatca | gcggcgccga | caaggcattc | gagatcgctt | ctagcagcgg | cgccgagcgt | 600 |
| gtggcgtcgg | taaccagagg | ggtcgacgac | cggcaggccg | tggtgacgtt | cgccaagccg | 660 |
| tacgcggagt | ggcgcggtat | gttcgcgggc | aacggcatgc | tgctgccggc | cagtatgacc | 720 |
| gccacacccg | aggcattcaa | taagggtcaa | ctcgatgggc | ccggtccgtc | ggcgggtccg | 780 |
| ttcgtcgtgt | ctgccctgga | ccgcaccgcg | cagcgaatcg | tgttgacccg | taacccgaga | 840 |
| tggtgggggg | cacggccacg | cctggacagc | atcacatacc | tggtgctcga | tgatgccgcc | 900 |
| cggctgccgg | cgctgcagaa | caacacaatc | gacgccaccg | gcgtcggcac | actggaccag | 960 |
| ctgaccatcg | cggcgcgcac | caagggcatc | tcgatccggc | gcgcccccgg | gcccagctgg | 1020 |
| tatcacttca | ccctcaacgg | tgcgcctggg | tcgatcctcg | ccgacaaggc | gctgcgcctg | 1080 |
| gcgatcgcca | agggcatcga | ccgatacacc | atcgccaggg | tcgcccaata | cggcctcacc | 1140 |
| agcgacccgg | tgccactgaa | caaccacgtc | ttcgtcgccg | gccaagacgg | ctaccaggac | 1200 |
| aacagcggcg | ttgtcgccta | caacccggaa | caagcgaaac | gggagctgga | cgccctgggc | 1260 |
| tggaggcgaa | gcggcgcgtt | ccgggagaag | gacggtcgcc | agctcgtcat | ccgcgatctg | 1320 |
| ttctacgacg | cacaaagcac | ccggcagttc | gcccagatcg | cccaacacac | cctggcgcag | 1380 |
| atcggcgtca | aactcgaact | tcaggccaag | tccggcagcg | gtttcttcag | cgactacgtc | 1440 |
| aacgtggggg | ctttcgacat | cgcacagttc | ggctgggtgg | cgacgcgtt | tccgctgtca | 1500 |
| tcgctcaccc | agatctacgc | ttcggacggg | gaaagcaact | tcggcaagat | cggtagcccg | 1560 |
| caaatcgacg | ccgcgatcga | gcgaacgctg | gcagaactcg | atcccggcaa | ggcgagggcc | 1620 |
| ttggccaacc | aggtcgacga | gctgatctgg | gccgaaggat | tcagcctgcc | gcttacccag | 1680 |
| tcgcccggca | ccgttgcggt | ccgcagcacg | ctggccaact | tcggcgcgac | gggtctggca | 1740 |
| gacctggact | acaccgccat | cgggttcatg | cgacgctgag | ccggcggcga | ccagctcagc | 1800 |
| tgaagcttaa | gtcggcggaa | ttc | | | | 1823 |

<210> SEQ ID NO 119
<211> LENGTH: 886
<212> TYPE: DNA
<213> ORGANISM: Mycobacterium tuberculosis

<400> SEQUENCE: 119

```
gaattcatct cacaagcgtg cggctcccac cgacccggc gccctcgag cctgggggct    60
gtcgcgatcc tgatcgcggc gacactttc gcgactgtcg ttgcggggtg cgggaaaaaa   120
ccgaccacgg cgagctcccc gagtcccggg tcgccgtcgc cggaagccca gcagatcctg   180
caagacagtt ccaaggcgac gaaggcctg cattccgtcc acgtggtggt gacggtaaac   240
aatctctcga ccctcccgtt tgagagcgtc gatgccgacg tgaccaacca accgcagggc   300
aatggccagg cggtgggcaa cgccaaggtc agaatgaagc ccaacacccc ggtggtggcc   360
accgagttcc tggtcacgaa caagaccatg tacacgaagc ggggcggcga ctatgtctcg   420
gtgggtccgg cggagaagat ctatgacccg ggcatcatcc tggacaagga ccgggggctg   480
ggcgcggtcg tcgggcaagt gcaaaaccg acaatccagg acgtgacgc catcgacggc   540
ctggccaccg tcaaggtgtc cggaccatc gacgccgcgg tgatcgatcc gatcgtgcct   600
cagctaggta agggtggggg caggctcccg ataaccttgt ggatcgtcga caccaacgcc   660
tcaacgccgg cacccgccgc gaacctggtg cggatggtca ttgacaagga ccaaggcaac   720
gtcgacatca cgctgtccaa ttgggtgcg ccggtcacca tcccgaaccc ggcgggataa   780
caggcgcgaa ccgcccggt ccagccccat cgctggtcga tggcctggcc ggtccggtac   840
tcgtccgcgg gcggaggccg ccttcgaaga aatcctttga gaattc            886
```

<210> SEQ ID NO 120
<211> LENGTH: 1020
<212> TYPE: DNA
<213> ORGANISM: Mycobacterium tuberculosis

<400> SEQUENCE: 120

```
gaattcatga tccagatcgc gcgcacctgg cgggtcttcg caggcggcat ggccaccggt    60
ttcatcggcg tggtgctggt caccgccggg aaggcctcag cggatcccct gctgccaccg   120
ccgcctatcc ctgccccagt ctcggcgccg gcaacagtcc cgcccgtgca gaacctcacg   180
gcgcttccgg gcgggagcag caacaggttc tcaccggcgc cagcacccgc accgatcgcg   240
tcgccgattc cggtcggagc acccgggtcc accgctgtgc cccgctgcc gccgccagtg   300
actcccgcga tcagcggcac acttcgggac cacctccggg agaagggcgt caagctggag   360
gcacagcgac cgcacggatt caaggcgctc gacatcacac tgcccatgcc gccgcgctgg   420
actcaggtgc ccgaccccaa cgtgcccgac gcgttcgtgg tgatcgccga ccggttgggc   480
aacagcgtct acacgtcgaa tgcgcagctg gtggtgtata ggctgatcgg tgacttcgat   540
cccgctgagg ccatcacaca cggctacatt gacagccaga aattgctcgc atggcagacc   600
acaaacgcct cgatggccaa tttcgacggc tttccgtcat caatcatcga gggcacctac   660
cgcgaaaacg acatgaccct caacacctcc cggcgccacg tcatcgccac ctccggagcc   720
gacaagtacc tggtttcgct gtcggtgacc accgcgctgt cgcaggcggt caccgacggg   780
ccggccaccg atgcgattgt caacggattc caagtggttg cgcatgcggc gcccgctcag   840
gcgcctgccc cggcacccgg ttcggcaccg gtgggactac ccgggcaggc gcctgggtat   900
ccgcccgcgg gcaccctgac accagtcccg ccgcgctagg tcgcgatgag gccgagcaga   960
aacacgggcc cgcatggagc tcggtgagcg gattcgtcgg cggcctcgaa gcttgaattc  1020
```

<210> SEQ ID NO 121
<211> LENGTH: 1354
<212> TYPE: DNA
<213> ORGANISM: Mycobacterium tuberculosis

<400> SEQUENCE: 121

-continued

```
gaattcacgc ggagccgggg attgcgctac gccacggtga tcgcgctggt ggccgcgctg      60
gtgggcggcg tgtacgtgct ctcgtccacc ggtaataagc gcaccatcgt gggctacttc     120
acctctgctg tcgggctcta tcccggtgac caggtccgcg tcctgggcgt cccggtgggt     180
gagatcgaca tgatcgagcc gcggtcgtcc gacgtcaaga tcactatgtc ggtgtccaag     240
gacgtcaagg tgcccgtgga cgtgcaggcc gtgatcatgt cgccgaattt ggtggcggcg     300
cgcttcattc agctcacccc ggtgtatacc ggcggggcgg tactgcccga caacggtcgg     360
atcgatctgg atcgcaccgc ggtgccggtg aatgggacg aggtgaaaga ggggctcacc      420
cggttggccg ccgacctgag tccggcggcg ggcgagctgc aggggccgct gggcgcggcg     480
atcaaccagg ccgcggacac ccttgacggc aacggagact cgttacacaa cgcgttgcgc    540
gagcttgcgc aggtcgccgg gcggctgggg gattcgcgcg cgacatcttt cggcaccgtc    600
aagaacctgc aggtactggt cgacgcgcta tcggagagcg acgagcagat tgtgcagttc    660
gccggccacg tggcatcggt gtcgcaggtg ctcgccgaca gctcggccaa tctggaccag    720
accctgggca cgctcaacca ggcgctgtcc gacatcaggg ggttcttgcg cgagaacaac    780
tcgacgctga tcgaaacggt gaatcagctc aacgactttg cgcagacgtt gagtgaccag    840
agcgagaaca tcgagcaagt gctgcacgtg gctgggccgg ggatcaccaa cttctacaac    900
atctatgacc ctgcgcaagg caccctcaac ggtctgttgt cgatacccaa cttcgctaac    960
ccggtgcagt tcatctgcgg cggttccttc gataccgccg cgggcccgtc ggcgccggac   1020
tactaccggc gcgccgagat ctgccgtgag cggctggggc cggtgctgcg ccggctcacg   1080
gtgaattacc cgccgatcat gttccacccg cttaacacga tcacggcgta caagggccag   1140
atcatctacg acaccccggc caccgaggcc aagtcggaga cgccggttcc ggaattgact   1200
tgggtacccg cgggaggagg agcgcctgtg ggcaaccccg cggatctgca gagcctactc   1260
gtcccaccgg cgcccggtcc ggcaccggcc ccgccggcgc cggggggcagg accgggcgag  1320
catgggggcg gcggatgaac cgaagcttga attc                                1354
```

<210> SEQ ID NO 122
<211> LENGTH: 1382
<212> TYPE: DNA
<213> ORGANISM: Mycobacterium tuberculosis

<400> SEQUENCE: 122
ggcatggacc cgctgaaccg ccgacaattc ctcgcgctgg ccgctgccgc cgccggcgtg 60
accgccggct gcgccgggat gggcggcggc ggttcggtga agtccggttc cggcccaatc 120
gacttctggt ccagtcatcc cggccaatcc agcgcggcgg aacgggagct gatcggtcgt 180
ttccaggacc gattccccac tctgtcggtc aagctgatcg acgccggcaa ggactacgac 240
gaggtggcac agaaattcaa tgcggcgctc atcggaaccg acgtgcccga cgtcgttttg 300
ctcgacgacc gatggtggtt ccatttcgcc ctcagcggtg ttctcactgc ccttgacgac 360
ctgttcggcc aagttggggt ggacacaacg gattacgtcg attcgctgct ggccgactat 420
gagttcaacg gccgccatta cgctgtgccg tatgctcgct cgacgccgct gttctactac 480
aacaaggcgg cgtggcaaca ggccggccta cccgaccgcg gaccgcaatc ctggtcagag 540
ttcgacgagt ggggtccgga gttacagcgc gtggtcggcg ccggtcgatc ggcgcacggc 600
tgggctaacg ccgacctcat ctcgtggacg tttcagggac cgaactgggc attcggcggt 660
gcctactccg acaagtggac attgacattg accgagcccg ccacgatcgc ggccggcaac 720

```
ttctatcgga actccatcca tggcaagggt tatgcggcgg tcgccaacga tattgccaac    780
gagttcgcca ccggaatcct ggcctcggcc gtggcatcca ccggctcgct ggccggcatc    840
accgcatctg cccgattcga cttcggcgcc gcaccgctgc ccacgggccc ggacgcagcg    900
cccgcctgtc cgacgggcgg tgcggggctg gcgataccgg ccaagctctc cgaggagcga    960
aaagtcaacg cgctcaagtt catcgcattc gtcaccaacc cgacgaacac cgcctacttc   1020
agccagcaaa ccggctatct gccggtgcgc aagtccgccg tcgacgatgc cagcgaacgg   1080
cactatctgg cggacaatcc ccgtgcgcgg gtggcgctcg accagctgcc acacacccgg   1140
acacaagact acgcacgggt tttcctgccc ggtggtgacc ggatcatctc cgccggcctg   1200
gaatccatcg gctgcgcgg  agccgacgtg accaagacct tcacgaacat ccaaaaacgg   1260
ttgcaggtca tcctggatcg gcagatcatg cggaagctgg cggggcatgg ctaacgttca   1320
gtactctgct gtcacccagc gctatcccgg cgccgacgcg ccgaccgtcg aagcttggat   1380
cc                                                                 1382
```

<210> SEQ ID NO 123
<211> LENGTH: 629
<212> TYPE: DNA
<213> ORGANISM: Mycobacterium tuberculosis

<400> SEQUENCE: 123

```
ggatccgtag cggtgcggcg taaggtgcgg aggttgactc tggcggtgtc ggcgttggtg     60
gctttgttcc cggcggtcgc ggggtgctcc gattccggcg acaacaaacc gggagcgacg    120
atcccgtcga caccggcaaa cgctgagggc cggcacggac ccttcttccc gcaatgtggc    180
ggcgtcagcg atcagacggt gaccgagctg acaagggtga ccgggctggt caacaccgcc    240
aagaattcgg tgggctgcca atggctggcg gcggcggta  tcttgggccc gcacttctcc    300
ttctcctggt accgcggcag cccgatcggg cgggaacgca agaccgagga gttgtcgcgc    360
gcgagtgtcg aggacatcaa catcgacggc acagcggtt  tcatcgccat cggtaacgag    420
cccagtttgg gtgactcact gtgtgaagtc ggaatccagt tctccgacga cttcatcgaa    480
tggtcggtga gtttcagcca gaagccgttc ccgctgccgt gcgacatcgc caaagaactg    540
acccgccaat cgattgcgaa ttcgaaatga cacgtgtcct ggtcggtgcg gccgccttga    600
tcaccgcaaa gcttgtcttg accggatcc                                     629
```

<210> SEQ ID NO 124
<211> LENGTH: 692
<212> TYPE: DNA
<213> ORGANISM: Mycobacterium tuberculosis

<400> SEQUENCE: 124

```
ggatccatcg ccatgcaact ctcctcccgg ttggaaaatc atcgcaagcc cttccccgg     60 acggtatcga cagggcaggc tatcgccatg gcgaagcgca cccggtccg  gaaggcctgc    120 acagttctag ccgtgctcgc cgcgacgcta ctcctcggcg cctgcggcgg tcccacgcag    180
ccacgcagca tcaccttgac ctttatccgc aacgcgcaat cccaggccaa cgccgacggg    240
atcatcgaca ccgacatgcc cggttccggc ctcagcgccg acggcaaagc agaggcgcag    300
caggtcgcgc accaggtttc ccgcagagat gtcgacagca tctattcctc ccccatggcg    360
gccgaccagc agaccgccgg gccgttggcc ggcgaacttg gcaagcaagt cgagattctt    420
ccgggcctgc aagcgatcaa cgccggctgg ttcaacggca acccgaatc  aatggccaac    480
```

| | |
|---|---:|
| tcaacatata tgctggcacc ggcagactgg ctggccggcg atgttcacaa cactattccg | 540 |
| gggtcgatca gcggcaccga attcaattcc cagttcagcg ccgccgtccg caagatctac | 600 |
| gacagcggcc acaatacgcc ggtcgtgttc tcgcaggggg tagcgatcat gatctggacg | 660 |
| ctgatgaacg cacgaaactc tagggaaagc tt | 692 |

<210> SEQ ID NO 125
<211> LENGTH: 1004
<212> TYPE: DNA
<213> ORGANISM: Mycobacterium tuberculosis

<400> SEQUENCE: 125

| | |
|---|---:|
| ggatccgggg gtgctgggat gacggaacac aacgaggacc cacagatcga gcgcgtggcc | 60 |
| gacgacgccg ccgacgagga ggcggttacg gagccgttgg ccaccgaatc gaaggacgaa | 120 |
| ccggccgagc acccagaatt cgaagggccg cgtcggcgcg cccgccgcga acgtgccgaa | 180 |
| cgtcgcgccg cgcaggctcg agctaccgcg atcgagcagg ctcgccgcgc ggccaaacgg | 240 |
| cgagcccgcg gcagatcgt cagtgagcag aaccccgcca aaccgccgc ccgaggtgtt | 300 |
| gttcgagggc tgaaggcgct gctcgcgacg tcgtgctgg ccgtcgtcgg gatcgggctt | 360 |
| gggctcgcgc tgtacttcac gccggcgatg tcggcccgcg agatcgtgat catcgggatc | 420 |
| ggggcggtga gccgcgagga ggttctcgac gccgccagag tgcggccggc aacgccgttg | 480 |
| ctgcagatcg acacccaaca ggttgctgac cgagtggcca cgatccggcg ggtggccagt | 540 |
| gcgcgggtgc agcggcagta cccgtcgcc ttgcggatca ccatcgtcga gcgggtcccg | 600 |
| gtggtggtca aggattttc ggacggcccg cacctttttg accgcgacgg cgtcgacttc | 660 |
| gcgaccgatc cgccaccgcc ggcgttgcct tatttcgatg tggacaatcc cggtcctagc | 720 |
| gatccgacga ccaaggcggc gctgcaggtg ttgaccgcgc tgcatcctga gttgcaagc | 780 |
| caggtggggc ggatcgcggc cccgtcggtg gcctcgatca ccctgacgtt ggccgatggc | 840 |
| cgcgtggtga tctggggaac caccgaccgc tgcgaagaga aggccgaaaa gctggcggcg | 900 |
| ctgttgaccc agccaggcag aacgtacgac gtgtccagcc ccgacctgcc gaccgtgaaa | 960 |
| tagccgaaaa aatgcccgcc gcgtatcggc gcgcctgcaa gctt | 1004 |

<210> SEQ ID NO 126
<211> LENGTH: 1624
<212> TYPE: DNA
<213> ORGANISM: Mycobacterium tuberculosis

<400> SEQUENCE: 126

| | |
|---|---:|
| ggatcccaga tgaatgtcgt cgacatttcg cggtggcagt tcggtatcac caccgtctat | 60 |
| cacttcattt tcgtaccgct gaccatcggc ctggccccgc tgatcgcggt catgcaaacg | 120 |
| ctgtgggtcg tcaccgataa ccccgcctgg tatcgcctca ccaaattctt cggcaaattg | 180 |
| ttcctgatca actttgccat cggcgtggcg accggaatcg tgcaggaatt tcagttcggc | 240 |
| atgaactgga gcgagtactc ccgattcgtc ggcgatgtct tcggcgcccc gctgccatg | 300 |
| gagggcctgg cggccttctt cttcgaatcc accttcatcg ggttgtggat cttcggctgg | 360 |
| aacaggctgc cccggctggt gcatctggcc tgcatctgga tcgtcgcaat cgcggtcaac | 420 |
| gtgtccgcgt tcttcatcat cgcggcaaac tccttcatgc agcatccggt cggcgcgcac | 480 |
| tacaacccga ccaccgggcg tgccgagttg agcagcatcg tcgtgctgct gaccaacaac | 540 |
| accgcacagg cggcgtttac ccacactgtc agcggtcgc tgctgaccgc cgggaccttc | 600 |
| gtcgccgcgg tgagcgcctg gtggctggtc cgttcgagca ccacgcacgc cgactcagat | 660 |

-continued

```
acccaagcca tgtatcgtcc cgcgaccatc ctggggtgtt gggttgcgtt ggccgccacg      720
gccgggttgt tgttcaccgg cgaccaccaa ggcaagctga tgttccagca gcagccgatg      780
aagatggcgt cggccgaatc gttgtgcgat acccagacag atccaaactt ctctgtcctg      840
acggtcggcc ggcaaaacaa ctgcgacagc ctcacccgtg tcatcgaagt gccctatgtg      900
ttgccgttcc tcgccgaggg ccggatcagc ggtgtgacgt tgcagggtat ccgcgatctg      960
cagcaggaat accagcagcg cttcggacca aacgactacc ggcccaacct cttcgtcacc     1020
tactggtcat ttcgcatgat gatcgggttg atggcgatcc cggtgctgtt cgcactgatt     1080
gcgctctggc tcacccgtgg cggccagatc cccaatcaac gctggttctc ctggctggcg     1140
ctgctaacca tgcccgcccc gttcctggcc aacagcgccg gatgggtgtt caccgagatg     1200
gggcgccagc cctgggtcgt cgtccctaac ccgaccggtg atcagctggt tcgactcacc     1260
gtcaaagcag gcgtctcgga tcactccgcc accgtggtcg ccacgtcttt gctgatgttc     1320
accttggtct acgcggtact tgcggtcatc tggtgctggc tgctcaagcg ttacatcgtc     1380
gaaggccccc tggaacacga cgcggaaccg gctgcgcacg gggcaccccg cgacgacgag     1440
gtagcaccat tgtcgtttgc ttactgaggc caactgaccc cggaaaggag cagccggtgg     1500
tactccaaga attgtggttc ggtgtcatcg cagcgctgtt cctcggtttc ttcatcctag     1560
aagggttcga cttcggcgtg ggcatgctga tggcgccgtt cgctcatgtc ggtatggggg     1620
atcc                                                                  1624

<210> SEQ ID NO 127
<211> LENGTH: 1414
<212> TYPE: DNA
<213> ORGANISM: Mycobacterium tuberculosis

<400> SEQUENCE: 127
gaattccaag gcgtcgatcg gcacggtgtt ccaggaccgg gccgctcgct acggtgaccg       60
agtcttcctg aaattcggcg atcagcagct gacctaccgc gacgctaacg ccaccgccaa      120
ccggtacgcc gcggtgttgg ccgcccgcgg cgtcggcccc ggcgacgtcg ttggcatcat      180
gttgcgtaac tcacccagca cagtcttggc gatgctggcc acggtcaagt gcggcgctat      240
cgccggcatg ctcaactacc accagcgcgg cgaggtgttg gcgcacagcc tgggtctgct      300
ggacgcgaag gtactgatcg cagagtccga cttggtcagc gccgtcgccg aatgcgggcgc      360 ctcgcgcggc cgggtagcgg gcgacgtgct gaccgtcgag gacgtggagc gattcgccac      420
aacggcgccc gccaccaacc cggcgtcggc gtcggcggtg caagccaaag acaccgcgtt      480
ctacatcttc acctcgggca ccaccggatt cccaaggcc agtgtcatga cgcatcatcg      540
gtggctgcgg gcgctggccg tcttcggagg gatgggggctg cggctgaagg gttccgacac      600
gctctacagc tgcctgccgc tgtaccacaa caacgcgtta acggtcgcgg tgtcgtcggt      660
gatcaattct ggggcgaccc tggcgctggg taagtcgttt tcggcgtcgc ggttctggga      720
tgaggtgatt gccaaccggg cgacggcgtt cgtctacatc ggcgaaatct gccgttatct      780
gctcaaccag ccggccaagc cgaccgaccg tgcccaccag gtgcgggtga tctgcggtaa      840
cgggctgcgg ccggagatct gggatgagtt caccacccgc ttcggggtcg cgcgggtgtg      900
cgagttctac gccgccagcg aaggcaactc ggccttatc aacatcttca cgtgcccag      960 gaccgccggg tatcgccga tgccgcttgc ctttgtggaa tacgacctgg acaccggcga     1020
tccgctgcgg gatgcgagcg ggcgagtgcg tcgggtaccc gacggtgaac ccggcctgtt     1080
```

```
gcttagccgg gtcaaccggc tgcagccgtt cgacggctac accgacccgg ttgccagcga   1140
aaagaagttg gtgcgcaacg cttttcgaga tggcgactgt tggttcaaca ccggtgacgt   1200
gatgagcccg cagggcatgg ccatgccgc cttcgtcgat cggctgggcg acaccttccg   1260
ctggaagggc gagaatgtcg ccaccactca ggtcgaagcg gcactggcct ccgaccagac   1320
cgtcgaggag tgcacggtct acggcgtcca gattccgcgc accggcgggc gcgccggaat   1380
ggccgcgatc acactgcgcg ctggcgccga attc                               1414
```

<210> SEQ ID NO 128
<211> LENGTH: 228
<212> TYPE: PRT
<213> ORGANISM: Mycobacterium tuberculosis

<400> SEQUENCE: 128

```
Gly Ser Ala Glu Tyr Ile Ser Asn Val Ile Tyr Glu Gly Pro Arg Ala
 1               5                  10                  15

Asp Ser Leu Tyr Ala Ala Asp Gln Arg Leu Arg Gln Leu Ala Asp Ser
             20                  25                  30

Val Arg Thr Thr Ala Glu Ser Leu Asn Thr Thr Leu Asp Glu Leu His
         35                  40                  45

Glu Asn Trp Lys Gly Ser Ser Glu Trp Met Ala Asp Ala Ala Leu
     50                  55                  60

Arg Tyr Leu Asp Trp Leu Ser Lys His Ser Arg Gln Ile Leu Arg Thr
 65                  70                  75                  80

Ala Arg Val Ile Glu Ser Leu Val Met Ala Tyr Glu Glu Thr Leu Leu
                 85                  90                  95

Arg Val Val Pro Pro Ala Thr Ile Ala Asn Asn Arg Glu Glu Val Arg
            100                 105                 110

Arg Leu Ile Ala Ser Asn Val Ala Gly Lys His Ser Ser Asn Arg
        115                 120                 125

Arg Pro Arg Gly Thr Ile Arg Ala Val Pro Gly Arg Lys Tyr Pro Ser
    130                 135                 140

Asn Gly Pro Leu Ser Lys Leu Asp Pro Ile Cys Ala Ile Glu Ala Ala
145                 150                 155                 160

Pro Met Ala Gly Ala Ala Asp Pro Gln Glu Arg Val Gly Pro Arg
                165                 170                 175

Gly Arg Arg Gly Leu Ala Gly Gln Gln Gln Cys Arg Gly Arg Pro Gly
            180                 185                 190

Pro Ser Leu Arg Cys Ser His Asp Thr Pro Arg Phe Gln Met Asn Gln
        195                 200                 205

Ala Phe His Thr Met Val Asn Met Leu Leu Thr Cys Phe Ala Cys Gln
    210                 215                 220

Glu Lys Pro Arg
225
```

<210> SEQ ID NO 129
<211> LENGTH: 597
<212> TYPE: PRT
<213> ORGANISM: Mycobacterium tuberculosis

<400> SEQUENCE: 129

```
Gly Ser Pro Ala Thr Met Pro Ser Ser Arg Asn Leu Ala Thr Asn Pro
 1               5                  10                  15

Glu Ile Ala Thr Gly Tyr Arg Arg Asp Met Thr Val Val Arg Thr Ala
             20                  25                  30
```

-continued

```
His Tyr Ala Ala Ala Thr Ala Asn Pro Leu Ala Thr Gln Val Ala Cys
         35                  40                  45
Arg Val Leu Arg Asp Gly Gly Thr Ala Asp Ala Val Val Ala Ala
 50                  55                  60
Gln Ala Val Leu Gly Leu Val Glu Pro Gln Ser Ser Gly Ile Gly Gly
 65                  70                  75                  80
Gly Gly Tyr Leu Val Tyr Phe Asp Ala Arg Thr Gly Ser Val Gln Ala
             85                  90                  95
Tyr Asp Gly Arg Glu Val Ala Pro Ala Ala Thr Glu Asn Tyr Leu
             100                 105                 110
Arg Trp Val Ser Asp Val Asp Arg Ser Ala Pro Arg Pro Asn Ala Arg
         115                 120                 125
Ala Ser Gly Arg Ser Ile Gly Val Pro Gly Ile Leu Arg Met Leu Glu
 130                 135                 140
Met Val His Asn Glu His Gly Arg Thr Pro Trp Arg Asp Leu Phe Gly
 145                 150                 155                 160
Pro Ala Val Thr Leu Ala Asp Gly Gly Phe Asp Ile Ser Ala Arg Met
             165                 170                 175
Gly Ala Ala Ile Ser Asp Ala Ala Pro Gln Leu Arg Asp Asp Pro Glu
             180                 185                 190
Ala Arg Lys Tyr Phe Leu Asn Pro Asp Gly Ser Pro Lys Pro Ala Gly
         195                 200                 205
Thr Arg Leu Thr Asn Pro Ala Tyr Ser Lys Thr Leu Ser Ala Ile Ala
         210                 215                 220
Ser Ala Gly Ala Asn Ala Phe Tyr Ser Gly Asp Ile Ala His Asp Ile
 225                 230                 235                 240
Val Ala Ala Ser Asp Thr Ser Asn Gly Arg Thr Pro Gly Leu Leu
             245                 250                 255
Thr Ile Glu Asp Leu Ala Gly Tyr Leu Ala Lys Arg Arg Gln Pro Leu
             260                 265                 270
Cys Thr Thr Tyr Arg Gly Arg Glu Ile Cys Gly Met Pro Ser Ser Gly
         275                 280                 285
Gly Val Ala Val Ala Ala Thr Leu Gly Ile Leu Glu His Phe Pro Met
 290                 295                 300
Ser Asp Tyr Ala Pro Ser Lys Val Asp Leu Asn Gly Gly Arg Pro Thr
 305                 310                 315                 320
Val Met Gly Val His Leu Ile Ala Glu Ala Arg Leu Ala Tyr Ala
             325                 330                 335
Asp Arg Asp Gln Tyr Ile Ala Asp Val Asp Phe Val Arg Leu Pro Gly
         340                 345                 350
Gly Ser Leu Thr Thr Leu Val Asp Pro Gly Tyr Leu Ala Ala Arg Ala
         355                 360                 365
Ala Leu Ile Ser Pro Gln His Ser Met Gly Ser Ala Arg Pro Gly Asp
         370                 375                 380
Phe Gly Ala Pro Thr Ala Val Ala Pro Val Pro Glu His Gly Thr
 385                 390                 395                 400
Ser His Leu Ser Val Val Asp Ser Tyr Gly Asn Ala Ala Thr Leu Thr
             405                 410                 415
Thr Thr Val Glu Ser Ser Phe Gly Ser Tyr His Leu Val Asp Gly Phe
             420                 425                 430
Ile Leu Asn Asn Gln Leu Ser Asp Phe Ser Ala Glu Pro His Ala Thr
         435                 440                 445
```

```
Asp Gly Ser Pro Val Ala Asn Arg Val Glu Pro Gly Lys Arg Pro Arg
        450                 455                 460

Ser Ser Met Ala Pro Thr Leu Val Phe Asp His Ser Ser Ala Gly Arg
465                 470                 475                 480

Gly Ala Leu Tyr Ala Val Leu Gly Ser Pro Gly Ser Met Ile Ile
                485                 490                 495

Gln Phe Val Val Lys Thr Leu Val Ala Met Leu Asp Trp Gly Leu Asn
                500                 505                 510

Pro Gln Gln Ala Val Ser Leu Val Asp Phe Gly Ala Ala Asn Ser Pro
                515                 520                 525

His Thr Asn Leu Gly Gly Glu Asn Pro Glu Ile Asn Thr Ser Asp Asp
        530                 535                 540

Gly Asp His Asp Pro Leu Val Gln Gly Leu Arg Ala Leu Gly His Arg
545                 550                 555                 560

Val Asn Leu Ala Glu Gln Ser Ser Gly Leu Ser Ala Ile Thr Arg Ser
                565                 570                 575

Glu Ala Gly Trp Ala Gly Gly Ala Asp Pro Arg Arg Glu Gly Ala Val
                580                 585                 590

Met Gly Asp Asp Ala
        595
```

<210> SEQ ID NO 130
<211> LENGTH: 163
<212> TYPE: PRT
<213> ORGANISM: Mycobacterium tuberculosis

<400> SEQUENCE: 130

```
Glu Phe Lys Arg Gly Val Ala Thr Leu Pro Val Ile Leu Val Ile Leu
 1               5                  10                  15

Leu Ser Val Ala Ala Gly Ala Gly Ala Trp Leu Leu Val Arg Gly His
                20                  25                  30

Gly Pro Gln Gln Pro Glu Ile Ser Ala Tyr Ser His Gly His Leu Thr
            35                  40                  45

Arg Val Gly Pro Tyr Leu Tyr Cys Asn Val Val Asp Leu Asp Asp Cys
        50                  55                  60

Gln Thr Pro Gln Ala Gln Gly Glu Leu Pro Val Ser Glu Arg Tyr Pro
65                  70                  75                  80

Val Gln Leu Ser Val Pro Glu Val Ile Ser Arg Ala Pro Trp Arg Leu
                85                  90                  95

Leu Gln Val Tyr Gln Asp Pro Ala Asn Thr Thr Ser Thr Leu Phe Arg
                100                 105                 110

Pro Asp Thr Arg Leu Ala Val Thr Ile Pro Thr Val Asp Pro Gln Arg
            115                 120                 125

Gly Arg Leu Thr Gly Ile Val Val Gln Leu Leu Thr Leu Val Val Asp
        130                 135                 140

His Ser Gly Glu Leu Arg Asp Val Pro His Ala Glu Trp Ser Val Arg
145                 150                 155                 160

Leu Ile Phe
```

<210> SEQ ID NO 131
<211> LENGTH: 943
<212> TYPE: PRT
<213> ORGANISM: Mycobacterium tuberculosis

<400> SEQUENCE: 131

```
Glu Phe Ala Pro Met Leu Asp Ala Ala Ala Ala Trp Asp Gly Leu Ala
```

-continued

```
  1               5                  10                 15
Asp Glu Leu Gly Ser Ala Ala Ser Phe Ser Ala Val Thr Ala Gly
                20                  25                 30
Leu Ala Gly Ser Ser Trp Leu Gly Ala Ser Thr Ala Met Thr Gly
             35                  40                 45
Ala Ala Ala Pro Tyr Leu Gly Trp Leu Ser Ala Ala Ala Gln Ala
          50                  55                 60
Gln Gln Ala Ala Thr Gln Thr Arg Leu Ala Ala Ala Phe Glu Ala
 65                  70                  75                 80
Ala Leu Ala Ala Thr Val His Pro Ala Ile Ile Ser Ala Asn Arg Ala
                 85                  90                 95
Leu Phe Val Ser Leu Val Val Ser Asn Leu Leu Gly Gln Asn Ala Pro
                100                 105                110
Ala Ile Ala Ala Thr Glu Ala Ala Tyr Glu Gln Met Trp Ala Gln Asp
            115                 120                 125
Val Ala Ala Met Phe Gly Tyr His Ala Gly Ala Ser Ala Ala Val Ser
        130                 135                 140
Ala Leu Thr Pro Phe Gly Gln Ala Leu Pro Thr Val Ala Gly Gly Gly
145                 150                 155                 160
Ala Leu Val Ser Ala Ala Ala Gln Val Thr Thr Arg Val Phe Arg
                165                 170                 175
Asn Leu Gly Leu Ala Asn Val Gly Glu Gly Asn Val Gly Asn Gly Asn
                180                 185                 190
Val Gly Asn Phe Asn Leu Gly Ser Ala Asn Ile Gly Asn Gly Asn Ile
            195                 200                 205
Gly Ser Gly Asn Ile Gly Ser Ser Asn Ile Gly Phe Gly Asn Val Gly
        210                 215                 220
Pro Gly Leu Thr Ala Ala Leu Asn Asn Ile Gly Phe Gly Asn Thr Gly
225                 230                 235                 240
Ser Asn Asn Ile Gly Phe Gly Asn Thr Gly Ser Asn Ile Gly Phe
                245                 250                 255
Gly Asn Thr Gly Asp Gly Asn Arg Gly Ile Gly Leu Thr Gly Ser Gly
                260                 265                 270
Leu Leu Gly Phe Gly Gly Leu Asn Ser Gly Thr Gly Asn Ile Gly Leu
            275                 280                 285
Phe Asn Ser Gly Thr Gly Asn Val Gly Ile Gly Asn Ser Gly Thr Gly
290                 295                 300
Asn Trp Gly Ile Gly Asn Ser Gly Asn Ser Tyr Asn Thr Gly Phe Gly
305                 310                 315                 320
Asn Ser Gly Asp Ala Asn Thr Gly Phe Phe Asn Ser Gly Ile Ala Asn
                325                 330                 335
Thr Gly Val Gly Asn Ala Gly Asn Tyr Asn Thr Gly Ser Tyr Asn Pro
            340                 345                 350
Gly Asn Ser Asn Thr Gly Gly Phe Asn Met Gly Gln Tyr Asn Thr Gly
        355                 360                 365
Tyr Leu Asn Ser Gly Asn Tyr Asn Thr Gly Leu Ala Asn Ser Gly Asn
    370                 375                 380
Val Asn Thr Gly Ala Phe Ile Thr Gly Asn Phe Asn Asn Gly Phe Leu
385                 390                 395                 400
Trp Arg Gly Asp His Gln Gly Leu Ile Phe Gly Ser Pro Gly Phe Phe
                405                 410                 415
Asn Ser Thr Ser Ala Pro Ser Ser Gly Phe Phe Asn Ser Gly Ala Gly
                420                 425                 430
```

-continued

```
Ser Ala Ser Gly Phe Leu Asn Ser Gly Ala Asn Ser Gly Phe Phe
            435                 440                 445
Asn Ser Ser Gly Ala Ile Gly Asn Ser Gly Leu Ala Asn Ala Gly
    450                 455                 460
Val Leu Val Ser Gly Val Ile Asn Ser Gly Asn Thr Val Ser Gly Leu
465                 470                 475                 480
Phe Asn Met Ser Leu Val Ala Ile Thr Thr Pro Ala Leu Ile Ser Gly
                485                 490                 495
Phe Phe Asn Thr Gly Ser Asn Met Ser Gly Phe Phe Gly Gly Pro Pro
                500                 505                 510
Val Phe Asn Leu Gly Leu Ala Asn Arg Gly Val Val Asn Ile Leu Gly
                515                 520                 525
Asn Ala Asn Ile Gly Asn Tyr Asn Ile Leu Gly Ser Gly Asn Val Gly
    530                 535                 540
Asp Phe Asn Ile Leu Gly Ser Gly Asn Leu Gly Ser Gln Asn Ile Leu
545                 550                 555                 560
Gly Ser Gly Asn Val Gly Ser Phe Asn Ile Gly Ser Gly Asn Ile Gly
                565                 570                 575
Val Phe Asn Val Gly Ser Gly Ser Leu Gly Asn Tyr Asn Ile Gly Ser
                580                 585                 590
Gly Asn Leu Gly Ile Tyr Asn Ile Gly Phe Gly Asn Val Gly Asp Tyr
            595                 600                 605
Asn Val Gly Phe Gly Asn Ala Gly Asp Phe Asn Gln Gly Phe Ala Asn
            610                 615                 620
Thr Gly Asn Asn Asn Ile Gly Phe Ala Asn Thr Gly Asn Asn Asn Ile
625                 630                 635                 640
Gly Ile Gly Leu Ser Gly Asp Asn Gln Gln Gly Phe Asn Ile Ala Ser
                645                 650                 655
Gly Trp Asn Ser Gly Thr Gly Asn Ser Gly Leu Phe Asn Ser Gly Thr
                660                 665                 670
Asn Asn Val Gly Ile Phe Asn Ala Gly Thr Gly Asn Val Gly Ile Ala
            675                 680                 685
Asn Ser Gly Thr Gly Asn Trp Gly Ile Gly Asn Pro Gly Thr Asp Asn
    690                 695                 7
Thr Gly Ile Leu Asn Ala Gly Ser Tyr Asn Thr Gly Ile Leu Asn Ala
705                 710                 715                 720
Gly Asp Phe Asn Thr Gly Phe Tyr Asn Thr Gly Ser Tyr Asn Thr Gly
                725                 730                 735
Gly Phe Asn Val Gly Asn Thr Asn Thr Gly Asn Phe Asn Val Gly Asp
                740                 745                 750
Thr Asn Thr Gly Ser Tyr Asn Pro Gly Asp Thr Asn Thr Gly Phe Phe
            755                 760                 765
Asn Pro Gly Asn Val Asn Thr Gly Ala Phe Asp Thr Gly Asp Phe Asn
    770                 775                 780
Asn Gly Phe Leu Val Ala Gly Asp Asn Gln Gly Gln Ile Ala Ile Asp
785                 790                 795                 800
Leu Ser Val Thr Thr Pro Phe Ile Pro Ile Asn Glu Gln Met Val Ile
                805                 810                 815
Asp Val His Asn Val Met Thr Phe Gly Gly Asn Met Ile Thr Val Thr
                820                 825                 830
Glu Ala Ser Thr Val Phe Pro Gln Thr Phe Tyr Leu Ser Gly Leu Phe
            835                 840                 845
Phe Phe Gly Pro Val Asn Leu Ser Ala Ser Thr Leu Thr Val Pro Thr
```

-continued

```
    850                 855                 860

Ile Thr Leu Thr Ile Gly Gly Pro Thr Val Thr Val Pro Ile Ser Ile
865                 870                 875                 880

Val Gly Ala Leu Glu Ser Arg Thr Ile Thr Phe Leu Lys Ile Asp Pro
                885                 890                 895

Ala Pro Gly Ile Gly Asn Ser Thr Thr Asn Pro Ser Ser Gly Phe Phe
            900                 905                 910

Asn Ser Gly Thr Gly Gly Thr Ser Gly Phe Gln Asn Val Gly Gly Gly
        915                 920                 925

Ser Ser Gly Val Trp Asn Ser Gly Leu Ser Ser Lys Leu Gly Asn
    930                 935                 940

<210> SEQ ID NO 132
<211> LENGTH: 592
<212> TYPE: PRT
<213> ORGANISM: Mycobacterium tuberculosis

<400> SEQUENCE: 132

Glu Phe Ala Asp Arg Gly Gln Arg Arg Gly Cys Ala Pro Gly Ile Ala
  1               5                  10                  15

Ser Ala Leu Arg Ala Ser Phe Gln Gly Lys Ser Arg Pro Trp Thr Gln
             20                  25                  30

Thr Arg Tyr Trp Ala Phe Ala Leu Leu Thr Pro Leu Val Val Ala Met
         35                  40                  45

Val Leu Thr Gly Cys Ser Ala Ser Gly Thr Gln Leu Glu Leu Ala Pro
     50                  55                  60

Thr Ala Asp Arg Arg Ala Ala Val Gly Thr Thr Ser Asp Ile Asn Gln
 65                  70                  75                  80

Gln Asp Pro Ala Thr Leu Gln Asp Gly Gly Asn Leu Arg Leu Ser Leu
                 85                  90                  95

Thr Asp Phe Pro Pro Asn Phe Asn Ile Leu His Ile Asp Gly Asn Asn
            100                 105                 110

Ala Glu Val Ala Ala Met Met Lys Ala Thr Leu Pro Arg Ala Phe Ile
        115                 120                 125

Ile Gly Pro Asp Gly Ser Thr Thr Val Asp Thr Asn Tyr Phe Thr Ser
    130                 135                 140

Ile Glu Leu Thr Arg Thr Ala Pro Gln Val Val Thr Tyr Thr Ile Asn
145                 150                 155                 160

Pro Glu Ala Val Trp Ser Asp Gly Thr Pro Ile Thr Trp Arg Asp Ile
                165                 170                 175

Ala Ser Gln Ile His Ala Ile Ser Gly Ala Asp Lys Ala Phe Glu Ile
            180                 185                 190

Ala Ser Ser Ser Gly Ala Glu Arg Val Ala Ser Val Thr Arg Gly Val
        195                 200                 205

Asp Asp Arg Gln Ala Val Val Thr Phe Ala Lys Pro Tyr Ala Glu Trp
    210                 215                 220

Arg Gly Met Phe Ala Gly Asn Gly Met Leu Leu Pro Ala Ser Met Thr
225                 230                 235                 240

Ala Thr Pro Glu Ala Phe Asn Lys Gly Gln Leu Asp Gly Pro Gly Pro
                245                 250                 255

Ser Ala Gly Pro Phe Val Val Ser Ala Leu Asp Arg Thr Ala Gln Arg
            260                 265                 270

Ile Val Leu Thr Arg Asn Pro Arg Trp Trp Gly Ala Arg Pro Arg Leu
        275                 280                 285
```

```
Asp Ser Ile Thr Tyr Leu Val Leu Asp Asp Ala Ala Arg Leu Pro Ala
    290                 295                 300

Leu Gln Asn Asn Thr Ile Asp Ala Thr Gly Val Gly Thr Leu Asp Gln
305                 310                 315                 320

Leu Thr Ile Ala Ala Arg Thr Lys Gly Ile Ser Ile Arg Arg Ala Pro
                325                 330                 335

Gly Pro Ser Trp Tyr His Phe Thr Leu Asn Gly Ala Pro Gly Ser Ile
                340                 345                 350

Leu Ala Asp Lys Ala Leu Arg Leu Ala Ile Ala Lys Gly Ile Asp Arg
                355                 360                 365

Tyr Thr Ile Ala Arg Val Ala Gln Tyr Gly Leu Thr Ser Asp Pro Val
    370                 375                 380

Pro Leu Asn Asn His Val Phe Val Ala Gly Gln Asp Gly Tyr Gln Asp
385                 390                 395                 400

Asn Ser Gly Val Val Ala Tyr Asn Pro Glu Gln Ala Lys Arg Glu Leu
                405                 410                 415

Asp Ala Leu Gly Trp Arg Arg Ser Gly Ala Phe Arg Glu Lys Asp Gly
                420                 425                 430

Arg Gln Leu Val Ile Arg Asp Leu Phe Tyr Asp Ala Gln Ser Thr Arg
    435                 440                 445

Gln Phe Ala Gln Ile Ala Gln His Thr Leu Ala Gln Ile Gly Val Lys
    450                 455                 460

Leu Glu Leu Gln Ala Lys Ser Gly Ser Gly Phe Phe Ser Asp Tyr Val
465                 470                 475                 480

Asn Val Gly Ala Phe Asp Ile Ala Gln Phe Gly Trp Val Gly Asp Ala
                485                 490                 495

Phe Pro Leu Ser Ser Leu Thr Gln Ile Tyr Ala Ser Asp Gly Glu Ser
                500                 505                 510

Asn Phe Gly Lys Ile Gly Ser Pro Gln Ile Asp Ala Ala Ile Glu Arg
                515                 520                 525

Thr Leu Ala Glu Leu Asp Pro Gly Lys Ala Arg Ala Leu Ala Asn Gln
    530                 535                 540

Val Asp Glu Leu Ile Trp Ala Glu Gly Phe Ser Leu Pro Leu Thr Gln
545                 550                 555                 560

Ser Pro Gly Thr Val Ala Val Arg Ser Thr Leu Ala Asn Phe Gly Ala
                565                 570                 575

Thr Gly Leu Ala Asp Leu Asp Tyr Thr Ala Ile Gly Phe Met Arg Arg
                580                 585                 590

<210> SEQ ID NO 133
<211> LENGTH: 259
<212> TYPE: PRT
<213> ORGANISM: Mycobacterium tuberculosis

<400> SEQUENCE: 133

Glu Phe Ile Ser Gln Ala Cys Gly Ser His Arg Pro Arg Arg Pro Ser
  1               5                  10                  15

Ser Leu Gly Ala Val Ala Ile Leu Ile Ala Ala Thr Leu Phe Ala Thr
                 20                  25                  30

Val Val Ala Gly Cys Gly Lys Lys Pro Thr Thr Ala Ser Ser Pro Ser
             35                  40                  45

Pro Gly Ser Pro Ser Pro Glu Ala Gln Gln Ile Leu Gln Asp Ser Ser
         50                  55                  60

Lys Ala Thr Lys Gly Leu His Ser Val His Val Val Thr Val Asn
 65                  70                  75                  80
```

-continued

```
Asn Leu Ser Thr Leu Pro Phe Glu Ser Val Asp Ala Asp Val Thr Asn
                 85                  90                  95
Gln Pro Gln Gly Asn Gly Gln Ala Val Gly Asn Ala Lys Val Arg Met
            100                 105                 110
Lys Pro Asn Thr Pro Val Val Ala Thr Glu Phe Leu Val Thr Asn Lys
            115                 120                 125
Thr Met Tyr Thr Lys Arg Gly Gly Asp Tyr Val Ser Val Gly Pro Ala
        130                 135                 140
Glu Lys Ile Tyr Asp Pro Gly Ile Ile Leu Asp Lys Asp Arg Gly Leu
145                 150                 155                 160
Gly Ala Val Val Gly Gln Val Gln Asn Pro Thr Ile Gln Gly Arg Asp
                165                 170                 175
Ala Ile Asp Gly Leu Ala Thr Val Lys Val Ser Gly Thr Ile Asp Ala
            180                 185                 190
Ala Val Ile Asp Pro Ile Val Pro Gln Leu Gly Lys Gly Gly Gly Arg
        195                 200                 205
Leu Pro Ile Thr Leu Trp Ile Val Asp Thr Asn Ala Ser Thr Pro Ala
210                 215                 220
Pro Ala Ala Asn Leu Val Arg Met Val Ile Asp Lys Asp Gln Gly Asn
225                 230                 235                 240
Val Asp Ile Thr Leu Ser Asn Trp Gly Ala Pro Val Thr Ile Pro Asn
                245                 250                 255
Pro Ala Gly

<210> SEQ ID NO 134
<211> LENGTH: 312
<212> TYPE: PRT
<213> ORGANISM: Mycobacterium tuberculosis

<400> SEQUENCE: 134

Glu Phe Met Ile Gln Ile Ala Arg Thr Trp Arg Val Phe Ala Gly Gly
 1               5                  10                  15
Met Ala Thr Gly Phe Ile Gly Val Val Leu Val Thr Ala Gly Lys Ala
             20                 25                  30
Ser Ala Asp Pro Leu Leu Pro Pro Pro Ile Pro Ala Pro Val Ser
         35                  40                  45
Ala Pro Ala Thr Val Pro Pro Val Gln Asn Leu Thr Ala Leu Pro Gly
     50                  55                  60
Gly Ser Ser Asn Arg Phe Ser Pro Ala Pro Ala Pro Ala Pro Ile Ala
 65                  70                  75                  80
Ser Pro Ile Pro Val Gly Ala Pro Gly Ser Thr Ala Val Pro Pro Leu
                 85                  90                  95
Pro Pro Pro Val Thr Pro Ala Ile Ser Gly Thr Leu Arg Asp His Leu
            100                 105                 110
Arg Glu Lys Gly Val Lys Leu Glu Ala Gln Arg Pro His Gly Phe Lys
        115                 120                 125
Ala Leu Asp Ile Thr Leu Pro Met Pro Pro Arg Trp Thr Gln Val Pro
    130                 135                 140
Asp Pro Asn Val Pro Asp Ala Phe Val Val Ile Ala Asp Arg Leu Gly
145                 150                 155                 160
Asn Ser Val Tyr Thr Ser Asn Ala Gln Leu Val Val Tyr Arg Leu Ile
                165                 170                 175
Gly Asp Phe Asp Pro Ala Glu Ala Ile Thr His Gly Tyr Ile Asp Ser
            180                 185                 190
```

-continued

```
Gln Lys Leu Leu Ala Trp Gln Thr Thr Asn Ala Ser Met Ala Asn Phe
        195                 200                 205

Asp Gly Phe Pro Ser Ser Ile Ile Glu Gly Thr Tyr Arg Glu Asn Asp
    210                 215                 220

Met Thr Leu Asn Thr Ser Arg Arg His Val Ile Ala Thr Ser Gly Ala
225                 230                 235                 240

Asp Lys Tyr Leu Val Ser Leu Ser Val Thr Thr Ala Leu Ser Gln Ala
                245                 250                 255

Val Thr Asp Gly Pro Ala Thr Asp Ala Ile Val Asn Gly Phe Gln Val
            260                 265                 270

Val Ala His Ala Ala Pro Ala Gln Ala Pro Ala Pro Ala Pro Gly Ser
        275                 280                 285

Ala Pro Val Gly Leu Pro Gly Gln Ala Pro Gly Tyr Pro Pro Ala Gly
    290                 295                 300

Thr Leu Thr Pro Val Pro Pro Arg
305                 310
```

<210> SEQ ID NO 135
<211> LENGTH: 445
<212> TYPE: PRT
<213> ORGANISM: Mycobacterium tuberculosis

<400> SEQUENCE: 135

```
Glu Phe Thr Arg Ser Arg Gly Leu Arg Tyr Ala Thr Val Ile Ala Leu
1               5                   10                  15

Val Ala Ala Leu Val Gly Gly Val Tyr Val Leu Ser Ser Thr Gly Asn
            20                  25                  30

Lys Arg Thr Ile Val Gly Tyr Phe Thr Ser Ala Val Gly Leu Tyr Pro
        35                  40                  45

Gly Asp Gln Val Arg Val Leu Gly Val Pro Val Gly Glu Ile Asp Met
    50                  55                  60

Ile Glu Pro Arg Ser Ser Asp Val Lys Ile Thr Met Ser Val Ser Lys
65                  70                  75                  80

Asp Val Lys Val Pro Val Asp Val Gln Ala Val Ile Met Ser Pro Asn
                85                  90                  95

Leu Val Ala Ala Arg Phe Ile Gln Leu Thr Pro Val Tyr Thr Gly Gly
            100                 105                 110

Ala Val Leu Pro Asp Asn Gly Arg Ile Asp Leu Asp Arg Thr Ala Val
        115                 120                 125

Pro Val Glu Trp Asp Glu Val Lys Glu Gly Leu Thr Arg Leu Ala Ala
    130                 135                 140

Asp Leu Ser Pro Ala Ala Gly Glu Leu Gln Gly Pro Leu Gly Ala Ala
145                 150                 155                 160

Ile Asn Gln Ala Ala Asp Thr Leu Asp Gly Asn Gly Asp Ser Leu His
                165                 170                 175

Asn Ala Leu Arg Glu Leu Ala Gln Val Ala Gly Arg Leu Gly Asp Ser
            180                 185                 190

Arg Gly Asp Ile Phe Gly Thr Val Lys Asn Leu Gln Val Leu Val Asp
        195                 200                 205

Ala Leu Ser Glu Ser Asp Glu Gln Ile Val Gln Phe Ala Gly His Val
    210                 215                 220

Ala Ser Val Ser Gln Val Leu Ala Asp Ser Ser Ala Asn Leu Asp Gln
225                 230                 235                 240

Thr Leu Gly Thr Leu Asn Gln Ala Leu Ser Asp Ile Arg Gly Phe Leu
```

-continued

```
            245                 250                 255
Arg Glu Asn Asn Ser Thr Leu Ile Glu Thr Val Asn Gln Leu Asn Asp
                260                 265                 270
Phe Ala Gln Thr Leu Ser Asp Gln Ser Glu Asn Ile Glu Gln Val Leu
            275                 280                 285
His Val Ala Gly Pro Gly Ile Thr Asn Phe Tyr Asn Ile Tyr Asp Pro
        290                 295                 300
Ala Gln Gly Thr Leu Asn Gly Leu Leu Ser Ile Pro Asn Phe Ala Asn
305                 310                 315                 320
Pro Val Gln Phe Ile Cys Gly Ser Phe Asp Thr Ala Ala Gly Pro
                325                 330                 335
Ser Ala Pro Asp Tyr Tyr Arg Arg Ala Glu Ile Cys Arg Glu Arg Leu
            340                 345                 350
Gly Pro Val Leu Arg Arg Leu Thr Val Asn Tyr Pro Pro Ile Met Phe
                355                 360                 365
His Pro Leu Asn Thr Ile Thr Ala Tyr Lys Gly Gln Ile Ile Tyr Asp
        370                 375                 380
Thr Pro Ala Thr Glu Ala Lys Ser Glu Thr Pro Val Pro Glu Leu Thr
385                 390                 395                 400
Trp Val Pro Ala Gly Gly Ala Pro Val Gly Asn Pro Ala Asp Leu
                405                 410                 415
Gln Ser Leu Leu Val Pro Pro Ala Pro Gly Pro Ala Pro Ala Pro Pro
            420                 425                 430
Ala Pro Gly Ala Gly Pro Gly Glu His Gly Gly Gly
            435                 440                 445
```

<210> SEQ ID NO 136
<211> LENGTH: 437
<212> TYPE: PRT
<213> ORGANISM: Mycobacterium tuberculosis

<400> SEQUENCE: 136

```
Gly Met Asp Pro Leu Asn Arg Arg Gln Phe Leu Ala Leu Ala Ala Ala
1               5                   10                  15
Ala Ala Gly Val Thr Ala Gly Cys Ala Gly Met Gly Gly Gly Ser
            20                  25                  30
Val Lys Ser Gly Ser Gly Pro Ile Asp Phe Trp Ser His Pro Gly
        35                  40                  45
Gln Ser Ser Ala Ala Glu Arg Glu Leu Ile Gly Arg Phe Gln Asp Arg
    50                  55                  60
Phe Pro Thr Leu Ser Val Lys Leu Ile Asp Ala Gly Lys Asp Tyr Asp
65                  70                  75                  80
Glu Val Ala Gln Lys Phe Asn Ala Ala Leu Ile Gly Thr Asp Val Pro
                85                  90                  95
Asp Val Val Leu Leu Asp Asp Arg Trp Trp Phe His Phe Ala Leu Ser
            100                 105                 110
Gly Val Leu Thr Ala Leu Asp Asp Leu Phe Gly Gln Val Gly Val Asp
        115                 120                 125
Thr Thr Asp Tyr Val Asp Ser Leu Leu Ala Asp Tyr Glu Phe Asn Gly
    130                 135                 140
Arg His Tyr Ala Val Pro Tyr Ala Arg Ser Thr Pro Leu Phe Tyr Tyr
145                 150                 155                 160
Asn Lys Ala Ala Trp Gln Gln Ala Gly Leu Pro Asp Arg Gly Pro Gln
                165                 170                 175
```

-continued

```
Ser Trp Ser Glu Phe Asp Glu Trp Gly Pro Glu Leu Gln Arg Val Val
            180                 185                 190

Gly Ala Gly Arg Ser Ala His Gly Trp Ala Asn Ala Asp Leu Ile Ser
        195                 200                 205

Trp Thr Phe Gln Gly Pro Asn Trp Ala Phe Gly Gly Ala Tyr Ser Asp
        210                 215                 220

Lys Trp Thr Leu Thr Leu Thr Glu Pro Ala Thr Ile Ala Ala Gly Asn
225                 230                 235                 240

Phe Tyr Arg Asn Ser Ile His Gly Lys Gly Tyr Ala Ala Val Ala Asn
                245                 250                 255

Asp Ile Ala Asn Glu Phe Ala Thr Gly Ile Leu Ala Ser Ala Val Ala
            260                 265                 270

Ser Thr Gly Ser Leu Ala Gly Ile Thr Ala Ser Ala Arg Phe Asp Phe
        275                 280                 285

Gly Ala Ala Pro Leu Pro Thr Gly Pro Asp Ala Ala Pro Ala Cys Pro
        290                 295                 300

Thr Gly Gly Ala Gly Leu Ala Ile Pro Ala Lys Leu Ser Glu Glu Arg
305                 310                 315                 320

Lys Val Asn Ala Leu Lys Phe Ile Ala Phe Val Thr Asn Pro Thr Asn
                325                 330                 335

Thr Ala Tyr Phe Ser Gln Gln Thr Gly Tyr Leu Pro Val Arg Lys Ser
            340                 345                 350

Ala Val Asp Asp Ala Ser Glu Arg His Tyr Leu Ala Asp Asn Pro Arg
        355                 360                 365

Ala Arg Val Ala Leu Asp Gln Leu Pro His Thr Arg Thr Gln Asp Tyr
        370                 375                 380

Ala Arg Val Phe Leu Pro Gly Gly Asp Arg Ile Ile Ser Ala Gly Leu
385                 390                 395                 400

Glu Ser Ile Gly Leu Arg Gly Ala Asp Val Thr Lys Thr Phe Thr Asn
                405                 410                 415

Ile Gln Lys Arg Leu Gln Val Ile Leu Asp Arg Gln Ile Met Arg Lys
            420                 425                 430

Leu Ala Gly His Gly
            435

<210> SEQ ID NO 137
<211> LENGTH: 189
<212> TYPE: PRT
<213> ORGANISM: Mycobacterium tuberculosis

<400> SEQUENCE: 137

Gly Ser Val Ala Val Arg Arg Lys Val Arg Arg Leu Thr Leu Ala Val
1               5                   10                  15

Ser Ala Leu Val Ala Leu Phe Pro Ala Val Ala Gly Cys Ser Asp Ser
            20                  25                  30

Gly Asp Asn Lys Pro Gly Ala Thr Ile Pro Ser Thr Pro Ala Asn Ala
        35                  40                  45

Glu Gly Arg His Gly Pro Phe Pro Gln Cys Gly Gly Val Ser Asp
    50                  55                  60

Gln Thr Val Thr Glu Leu Thr Arg Val Thr Gly Leu Val Asn Thr Ala
65                  70                  75                  80

Lys Asn Ser Val Gly Cys Gln Trp Leu Ala Gly Gly Ile Leu Gly
                85                  90                  95

Pro His Phe Ser Phe Ser Trp Tyr Arg Gly Ser Pro Ile Gly Arg Glu
            100                 105                 110
```

```
Arg Lys Thr Glu Glu Leu Ser Arg Ala Ser Val Glu Asp Ile Asn Ile
        115                 120                 125

Asp Gly His Ser Gly Phe Ile Ala Ile Gly Asn Glu Pro Ser Leu Gly
    130                 135                 140

Asp Ser Leu Cys Glu Val Gly Ile Gln Phe Ser Asp Phe Ile Glu
145                 150                 155                 160

Trp Ser Val Ser Phe Ser Gln Lys Pro Phe Pro Leu Pro Cys Asp Ile
                165                 170                 175

Ala Lys Glu Leu Thr Arg Gln Ser Ile Ala Asn Ser Lys
            180                 185

<210> SEQ ID NO 138
<211> LENGTH: 230
<212> TYPE: PRT
<213> ORGANISM: Mycobacterium tuberculosis

<400> SEQUENCE: 138

Gly Ser Ile Ala Met Gln Leu Ser Ser Arg Leu Glu Asn His Arg Lys
1               5                   10                  15

Pro Phe Pro Arg Thr Val Ser Thr Gly Gln Ala Ile Ala Met Ala Lys
            20                  25                  30

Arg Thr Pro Val Arg Lys Ala Cys Thr Val Leu Ala Val Leu Ala Ala
        35                  40                  45

Thr Leu Leu Gly Ala Cys Gly Gly Pro Thr Gln Pro Arg Ser Ile
    50                  55                  60

Thr Leu Thr Phe Ile Arg Asn Ala Gln Ser Gln Ala Asn Ala Asp Gly
65              70                  75                  80

Ile Ile Asp Thr Asp Met Pro Gly Ser Gly Leu Ser Ala Asp Gly Lys
                85                  90                  95

Ala Glu Ala Gln Gln Val Ala His Gln Val Ser Arg Arg Asp Val Asp
            100                 105                 110

Ser Ile Tyr Ser Ser Pro Met Ala Ala Asp Gln Gln Thr Ala Gly Pro
        115                 120                 125

Leu Ala Gly Glu Leu Gly Lys Gln Val Glu Ile Leu Pro Gly Leu Gln
    130                 135                 140

Ala Ile Asn Ala Gly Trp Phe Asn Gly Lys Pro Glu Ser Met Ala Asn
145                 150                 155                 160

Ser Thr Tyr Met Leu Ala Pro Ala Asp Trp Leu Ala Gly Asp Val His
                165                 170                 175

Asn Thr Ile Pro Gly Ser Ile Ser Gly Thr Glu Phe Asn Ser Gln Phe
            180                 185                 190

Ser Ala Ala Val Arg Lys Ile Tyr Asp Ser Gly His Asn Thr Pro Val
        195                 200                 205

Val Phe Ser Gln Gly Val Ala Ile Met Ile Trp Thr Leu Met Asn Ala
    210                 215                 220

Arg Asn Ser Arg Glu Ser
225                 230

<210> SEQ ID NO 139
<211> LENGTH: 320
<212> TYPE: PRT
<213> ORGANISM: Mycobacterium tuberculosis

<400> SEQUENCE: 139

Gly Ser Gly Gly Ala Gly Met Thr Glu His Asn Glu Asp Pro Gln Ile
1               5                   10                  15
```

-continued

```
Glu Arg Val Ala Asp Asp Ala Ala Asp Glu Glu Ala Val Thr Glu Pro
                 20                  25                  30
Leu Ala Thr Glu Ser Lys Asp Glu Pro Ala Glu His Pro Glu Phe Glu
             35                  40                  45
Gly Pro Arg Arg Arg Ala Arg Arg Glu Arg Ala Glu Arg Arg Ala Ala
         50                  55                  60
Gln Ala Arg Ala Thr Ala Ile Glu Gln Ala Arg Arg Ala Ala Lys Arg
 65                  70                  75                  80
Arg Ala Arg Gly Gln Ile Val Ser Glu Gln Asn Pro Ala Lys Pro Ala
                 85                  90                  95
Ala Arg Gly Val Val Arg Gly Leu Lys Ala Leu Leu Ala Thr Val Val
                100                 105                 110
Leu Ala Val Val Gly Ile Gly Leu Gly Leu Ala Leu Tyr Phe Thr Pro
            115                 120                 125
Ala Met Ser Ala Arg Glu Ile Val Ile Gly Ile Gly Ala Val Ser
            130                 135                 140
Arg Glu Glu Val Leu Asp Ala Ala Arg Val Arg Pro Ala Thr Pro Leu
145                 150                 155                 160
Leu Gln Ile Asp Thr Gln Gln Val Ala Asp Arg Val Ala Thr Ile Arg
                165                 170                 175
Arg Val Ala Ser Ala Arg Val Gln Arg Gln Tyr Pro Ser Ala Leu Arg
                180                 185                 190
Ile Thr Ile Val Glu Arg Val Pro Val Val Lys Asp Phe Ser Asp
            195                 200                 205
Gly Pro His Leu Phe Asp Arg Asp Gly Val Asp Phe Ala Thr Asp Pro
        210                 215                 220
Pro Pro Pro Ala Leu Pro Tyr Phe Asp Val Asp Asn Pro Gly Pro Ser
225                 230                 235                 240
Asp Pro Thr Thr Lys Ala Ala Leu Gln Val Leu Thr Ala Leu His Pro
                245                 250                 255
Glu Val Ala Ser Gln Val Gly Arg Ile Ala Ala Pro Ser Val Ala Ser
                260                 265                 270
Ile Thr Leu Thr Leu Ala Asp Gly Arg Val Val Ile Trp Gly Thr Thr
            275                 280                 285
Asp Arg Cys Glu Glu Lys Ala Glu Lys Leu Ala Ala Leu Leu Thr Gln
        290                 295                 300
Pro Gly Arg Thr Tyr Asp Val Ser Ser Pro Asp Leu Pro Thr Val Lys
305                 310                 315                 320
```

<210> SEQ ID NO 140
<211> LENGTH: 488
<212> TYPE: PRT
<213> ORGANISM: Mycobacterium tuberculosis

<400> SEQUENCE: 140

```
Gly Ser Gln Met Asn Val Val Asp Ile Ser Arg Trp Gln Phe Gly Ile
 1               5                  10                  15
Thr Thr Val Tyr His Phe Ile Phe Val Pro Leu Thr Ile Gly Leu Ala
                 20                  25                  30
Pro Leu Ile Ala Val Met Gln Thr Leu Trp Val Val Thr Asp Asn Pro
             35                  40                  45
Ala Trp Tyr Arg Leu Thr Lys Phe Phe Gly Lys Leu Phe Leu Ile Asn
         50                  55                  60
Phe Ala Ile Gly Val Ala Thr Gly Ile Val Gln Glu Phe Gln Phe Gly
```

```
              65                  70                  75                  80
         Met Asn Trp Ser Glu Tyr Ser Arg Phe Val Gly Asp Val Phe Gly Ala
                         85                  90                  95
         Pro Leu Ala Met Glu Gly Leu Ala Ala Phe Phe Glu Ser Thr Phe
                        100                 105                 110
         Ile Gly Leu Trp Ile Phe Gly Trp Asn Arg Leu Pro Arg Leu Val His
                        115                 120                 125
         Leu Ala Cys Ile Trp Ile Val Ala Ile Ala Val Asn Val Ser Ala Phe
                        130                 135                 140
         Phe Ile Ile Ala Ala Asn Ser Phe Met Gln His Pro Val Gly Ala His
         145                 150                 155                 160
         Tyr Asn Pro Thr Thr Gly Arg Ala Glu Leu Ser Ser Ile Val Val Leu
                        165                 170                 175
         Leu Thr Asn Asn Thr Ala Gln Ala Ala Phe Thr His Thr Val Ser Gly
                        180                 185                 190
         Ala Leu Leu Thr Ala Gly Thr Phe Val Ala Val Ser Ala Trp Trp
                        195                 200                 205
         Leu Val Arg Ser Ser Thr Thr His Ala Asp Ser Asp Thr Gln Ala Met
                        210                 215                 220
         Tyr Arg Pro Ala Thr Ile Leu Gly Cys Trp Val Ala Leu Ala Ala Thr
         225                 230                 235                 240
         Ala Gly Leu Leu Phe Thr Gly Asp His Gln Gly Lys Leu Met Phe Gln
                        245                 250                 255
         Gln Gln Pro Met Lys Met Ala Ser Ala Glu Ser Leu Cys Asp Thr Gln
                        260                 265                 270
         Thr Asp Pro Asn Phe Ser Val Leu Thr Val Gly Arg Gln Asn Asn Cys
                        275                 280                 285
         Asp Ser Leu Thr Arg Val Ile Glu Val Pro Tyr Val Leu Pro Phe Leu
                        290                 295                 300
         Ala Glu Gly Arg Ile Ser Gly Val Thr Leu Gln Gly Ile Arg Asp Leu
         305                 310                 315                 320
         Gln Gln Glu Tyr Gln Gln Arg Phe Gly Pro Asn Asp Tyr Arg Pro Asn
                        325                 330                 335
         Leu Phe Val Thr Tyr Trp Ser Phe Arg Met Met Ile Gly Leu Met Ala
                        340                 345                 350
         Ile Pro Val Leu Phe Ala Leu Ile Ala Leu Trp Leu Thr Arg Gly Gly
                        355                 360                 365
         Gln Ile Pro Asn Gln Arg Trp Phe Ser Trp Leu Ala Leu Leu Thr Met
         370                 375                 380
         Pro Ala Pro Phe Leu Ala Asn Ser Ala Gly Trp Val Phe Thr Glu Met
         385                 390                 395                 400
         Gly Arg Gln Pro Trp Val Val Pro Asn Pro Thr Gly Asp Gln Leu
                        405                 410                 415
         Val Arg Leu Thr Val Lys Ala Gly Val Ser Asp His Ser Ala Thr Val
                        420                 425                 430
         Val Ala Thr Ser Leu Leu Met Phe Thr Leu Val Tyr Ala Val Leu Ala
                        435                 440                 445
         Val Ile Trp Cys Trp Leu Leu Lys Arg Tyr Ile Val Glu Gly Pro Leu
                        450                 455                 460
         Glu His Asp Ala Glu Pro Ala His Gly Ala Pro Arg Asp Asp Glu
         465                 470                 475                 480
         Val Ala Pro Leu Ser Phe Ala Tyr
                        485
```

```
<210> SEQ ID NO 141
<211> LENGTH: 471
<212> TYPE: PRT
<213> ORGANISM: Mycobacterium tuberculosis

<400> SEQUENCE: 141

Asn Ser Lys Ala Ser Ile Gly Thr Val Phe Gln Asp Arg Ala Ala Arg
  1               5                  10                  15

Tyr Gly Asp Arg Val Phe Leu Lys Phe Gly Asp Gln Gln Leu Thr Tyr
             20                  25                  30

Arg Asp Ala Asn Ala Thr Ala Asn Arg Tyr Ala Ala Val Leu Ala Ala
         35                  40                  45

Arg Gly Val Gly Pro Gly Asp Val Val Gly Ile Met Leu Arg Asn Ser
     50                  55                  60

Pro Ser Thr Val Leu Ala Met Leu Ala Thr Val Lys Cys Gly Ala Ile
 65                  70                  75                  80

Ala Gly Met Leu Asn Tyr His Gln Arg Gly Glu Val Leu Ala His Ser
                 85                  90                  95

Leu Gly Leu Leu Asp Ala Lys Val Leu Ile Ala Glu Ser Asp Leu Val
            100                 105                 110

Ser Ala Val Ala Glu Cys Gly Ala Ser Arg Gly Arg Val Ala Gly Asp
        115                 120                 125

Val Leu Thr Val Glu Asp Val Glu Arg Phe Ala Thr Thr Ala Pro Ala
130                 135                 140

Thr Asn Pro Ala Ser Ala Ser Ala Val Gln Ala Lys Asp Thr Ala Phe
145                 150                 155                 160

Tyr Ile Phe Thr Ser Gly Thr Thr Gly Phe Pro Lys Ala Ser Val Met
                165                 170                 175

Thr His His Arg Trp Leu Arg Ala Leu Ala Val Phe Gly Gly Met Gly
            180                 185                 190

Leu Arg Leu Lys Gly Ser Asp Thr Leu Tyr Ser Cys Leu Pro Leu Tyr
        195                 200                 205

His Asn Asn Ala Leu Thr Val Ala Val Ser Ser Val Ile Asn Ser Gly
    210                 215                 220

Ala Thr Leu Ala Leu Gly Lys Ser Phe Ser Ala Ser Arg Phe Trp Asp
225                 230                 235                 240

Glu Val Ile Ala Asn Arg Ala Thr Ala Phe Val Tyr Ile Gly Glu Ile
                245                 250                 255

Cys Arg Tyr Leu Leu Asn Gln Pro Ala Lys Pro Thr Asp Arg Ala His
            260                 265                 270

Gln Val Arg Val Ile Cys Gly Asn Gly Leu Arg Pro Glu Ile Trp Asp
        275                 280                 285

Glu Phe Thr Thr Arg Phe Gly Val Ala Arg Val Cys Glu Phe Tyr Ala
    290                 295                 300

Ala Ser Glu Gly Asn Ser Ala Phe Ile Asn Ile Phe Asn Val Pro Arg
305                 310                 315                 320

Thr Ala Gly Val Ser Pro Met Pro Leu Ala Phe Val Glu Tyr Asp Leu
                325                 330                 335

Asp Thr Gly Asp Pro Leu Arg Asp Ala Ser Gly Arg Val Arg Arg Val
            340                 345                 350

Pro Asp Gly Glu Pro Gly Leu Leu Leu Ser Arg Val Asn Arg Leu Gln
        355                 360                 365

Pro Phe Asp Gly Tyr Thr Asp Pro Val Ala Ser Glu Lys Lys Leu Val
```

```
                370              375              380
Arg Asn Ala Phe Arg Asp Gly Asp Cys Trp Phe Asn Thr Gly Asp Val
385                 390                  395                 400

Met Ser Pro Gln Gly Met Gly His Ala Ala Phe Val Asp Arg Leu Gly
                405                  410                 415

Asp Thr Phe Arg Trp Lys Gly Glu Asn Val Ala Thr Thr Gln Val Glu
                420                  425                 430

Ala Ala Leu Ala Ser Asp Gln Thr Val Glu Glu Cys Thr Val Tyr Gly
                435                  440                 445

Val Gln Ile Pro Arg Thr Gly Arg Ala Gly Met Ala Ala Ile Thr
    450                  455                 460

Leu Arg Ala Gly Ala Glu Phe
465                 470

<210> SEQ ID NO 142
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 142
gtcaaggatc cggcatggac ccgctgaacc gccgac                             36

<210> SEQ ID NO 143
<211> LENGTH: 44
<212> TYPE: DNA
<213> ORGANISM: Artificial Sequence
<220> FEATURE:
<223> OTHER INFORMATION: Description of Artificial Sequence:PCR Primer

<400> SEQUENCE: 143
atgtcgggat ccaagctttc gacggtcggc gcgtcggcgc cggg                    44

<210> SEQ ID NO 144
<211> LENGTH: 37
<212> TYPE: DNA
<213> ORGANISM: Artificial Sequence
<220> FEATURE:
<223> OTHER INFORMATION: Description of Artificial Sequence:PCR Primer

<400> SEQUENCE: 144
gcagatgcat ctaatgggat ccgcggagta tatctcc                            37

<210> SEQ ID NO 145
<211> LENGTH: 37
<212> TYPE: DNA
<213> ORGANISM: Artificial Sequence
<220> FEATURE:
<223> OTHER INFORMATION: Description of Artificial Sequence:PCR Primer

<400> SEQUENCE: 145
ggcgccgtgg gtgtcagcga agcttacctg gttgttg                            37

<210> SEQ ID NO 146
<211> LENGTH: 31
<212> TYPE: DNA
<213> ORGANISM: Artificial Sequence
<220> FEATURE:
 <223> OTHER INFORMATION: Description of Artificial Sequence:PCR Primer

< 400> SEQUENCE: 146 ggtgccgaat tcgcgccgat gctggacgcg g                                  31
```

<210> SEQ ID NO 147
<211> LENGTH: 38
<212> TYPE: DNA
<213> ORGANISM: Artificial Sequence
<220> FEATURE:
<223> OTHER INFORMATION: Description of Artificial Sequence:PCR Primer

<400> SEQUENCE: 147
acccgaattc ccaagcttgc tgctcaaacc actgttcc            38

<210> SEQ ID NO 148
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 148
gcgcccaagg gatccccggc taccatgcct tcg                 33

<210> SEQ ID NO 149
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 149
ctcgaaggga tccgcgttcg tttggccgcc cgc                 33

<210> SEQ ID NO 150
<211> LENGTH: 37
<212> TYPE: DNA
<213> ORGANISM: Artificial Sequence
<220> FEATURE:
<223> OTHER INFORMATION: Description of Artificial Sequence:PCR Primer

<400> SEQUENCE: 150
ggcagtggga tccgtagcgg tgcggcgtaa ggtgcgg             37

<210> SEQ ID NO 151
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 151
gacttcgtgg atccggtcaa gacaagcttt gcggtgatca aggcggcc     48

<210> SEQ ID NO 152
<211> LENGTH: 43
<212> TYPE: DNA
<213> ORGANISM: Artificial Sequence
<220> FEATURE:
<223> OTHER INFORMATION: Description of Artificial Sequence:PCR Primer

<400> SEQUENCE: 152
catgaatgaa ttcatctcac aagcgtgcgg ctcccaccga ccc          43

<210> SEQ ID NO 153
<211> LENGTH: 36
<212> TYPE: DNA
<213> ORGANISM: Artificial Sequence
<220> FEATURE:

<223> OTHER INFORMATION: Description of Artificial Sequence:PCR Primer

<400> SEQUENCE: 153
ccttggcgaa ttctcaaagg aaagcttcga aggcgg                                    36

<210> SEQ ID NO 154
<211> LENGTH: 37
<212> TYPE: DNA
<213> ORGANISM: Artificial Sequence
<220> FEATURE:
<223> OTHER INFORMATION: Description of Artificial Sequence:PCR Primer

<400> SEQUENCE: 154
ggagttcgga tccatcgcca tgcaactctc ctcccgg                                   37

<210> SEQ ID NO 155
<211> LENGTH: 46
<212> TYPE: DNA
<213> ORGANISM: Artificial Sequence
<220> FEATURE:
<223> OTHER INFORMATION: Description of Artificial Sequence:PCR Primer

<400> SEQUENCE: 155
gggcagtgga tccgtggtca gcaagctttc cctagagttt cgtgcg                         46

<210> SEQ ID NO 156
<211> LENGTH: 35
<212> TYPE: DNA
<213> ORGANISM: Artificial Sequence
<220> FEATURE:
<223> OTHER INFORMATION: Description of Artificial Sequence:PCR Primer

<400> SEQUENCE: 156
gtggcgccga attcaagcgc ggtgtcgcaa cgctg                                     35

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 157
cgcttaagcg cgaagcttcg tcgagccgcg                                           30

<210> SEQ ID NO 158
<211> LENGTH: 38
<212> TYPE: DNA
<213> ORGANISM: Artificial Sequence
<220> FEATURE:
<223> OTHER INFORMATION: Description of Artificial Sequence:PCR Primer

<400> SEQUENCE: 158
gaccggaatt catgatccag atcgcgcgca cctggcgg                                  38

<210> SEQ ID NO 159
<211> LENGTH: 44
<212> TYPE: DNA
<213> ORGANISM: Artificial Sequence
<220> FEATURE:
<223> OTHER INFORMATION: Description of Artificial Sequence:PCR Primer

<400> SEQUENCE: 159
aacatgaatt caagcttcga ggccgccgac gaatccgctc accg                           44

<210> SEQ ID NO 160
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 160
cgggtcgccg aattcacgcg gagccgggga ttgcgc     36

<210> SEQ ID NO 161
<211> LENGTH: 39
<212> TYPE: DNA
<213> ORGANISM: Artificial Sequence
<220> FEATURE:
<223> OTHER INFORMATION: Description of Artificial Sequence:PCR Primer

<400> SEQUENCE: 161
ggcggaattc aagcttcggt tcatccgccg cccccatgc     39

<210> SEQ ID NO 162
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 162
ccccggggat ccgggggtgc tgggatgacg g     31

<210> SEQ ID NO 163
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 163
acgacggatc ctaagcttgc aggcgcgccg atacgcggc     39

<210> SEQ ID NO 164
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 164
tctccgggga tcccagatga atgtcgtcga catttc     36

<210> SEQ ID NO 165
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 165
gggtctccgg atcccccata ccgacatg     28

<210> SEQ ID NO 166
<211> LENGTH: 32
<212> TYPE: DNA
<213> ORGANISM: Artificial Sequence
<220> FEATURE:
<223> OTHER INFORMATION: Description of Artificial Sequence: PCR primer -continued

```
<400> SEQUENCE: 166
ccgactcgag cggcggcgca cacacaacgg tc                                   32

<210> SEQ ID NO 167
<211> LENGTH: 32
<212> TYPE: DNA
<213> ORGANISM: Artificial Sequence
<220> FEATURE:
<223> OTHER INFORMATION: Description of Artificial Sequence: PCR primer

<400> SEQUENCE: 167
aatcctcgag ccctgcggtc gccttccgag cg                                   32

<210> SEQ ID NO 168
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 168
atccggcccg aattcgctga ccgtggccag cgacga                               36

<210> SEQ ID NO 169
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 169
gatcggggag aattccgccg acttaagctt cagctgagct gg                        42
```